US011993794B2

(12) United States Patent
Amin

(10) Patent No.: US 11,993,794 B2
(45) Date of Patent: May 28, 2024

(54) METHODS TO CREATE CHEMICALLY-INDUCED DIMERIZING PROTEIN SYSTEMS FOR REGULATION OF CELLULAR EVENTS

(71) Applicant: Fred Hutchinson Cancer Center, Seattle, WA (US)

(72) Inventor: Rupesh Amin, Seattle, WA (US)

(73) Assignee: FRED HUTCHINSON CANCER CENTER, Seattle, WA (US)

( * ) Notice: Subject to any disclaimer, the term of this patent is extended or adjusted under 35 U.S.C. 154(b) by 409 days.

(21) Appl. No.: 17/203,473

(22) Filed: Mar. 16, 2021

(65) Prior Publication Data

US 2021/0198646 A1 Jul. 1, 2021

Related U.S. Application Data

(62) Division of application No. 15/770,433, filed as application No. PCT/US2016/058237 on Oct. 21, 2016, now Pat. No. 10,954,500.

(60) Provisional application No. 62/245,756, filed on Oct. 23, 2015.

(51) Int. Cl.
| | |
|---|---|
| *C12N 9/52* | (2006.01) |
| *C07K 14/705* | (2006.01) |
| *C07K 16/00* | (2006.01) |
| *C07K 16/44* | (2006.01) |
| *C07K 16/46* | (2006.01) |
| *C12N 9/50* | (2006.01) |
| *C12N 9/64* | (2006.01) |
| *C12N 9/96* | (2006.01) |
| *C12N 15/70* | (2006.01) |
| *C12N 15/81* | (2006.01) |

(52) U.S. Cl.
CPC .............. *C12N 9/52* (2013.01); *C07K 14/705* (2013.01); *C07K 16/005* (2013.01); *C07K 16/44* (2013.01); *C07K 16/468* (2013.01); *C12N 9/50* (2013.01); *C12N 9/6472* (2013.01); *C12N 9/96* (2013.01); *C07K 2317/22* (2013.01); *C07K 2317/32* (2013.01); *C07K 2317/569* (2013.01); *C07K 2317/622* (2013.01); *C07K 2317/92* (2013.01); *C07K 2317/94* (2013.01); *C07K 2319/61* (2013.01); *C07K 2319/70* (2013.01); *C07K 2319/71* (2013.01); *C07K 2319/715* (2013.01); *C07K 2319/80* (2013.01); *C12N 15/70* (2013.01); *C12N 15/81* (2013.01)

(58) Field of Classification Search
None
See application file for complete search history.

(56) References Cited

U.S. PATENT DOCUMENTS

| | | |
|---|---|---|
| 6,180,370 B1 | 1/2001 | Queen et al. |
| 2002/0004202 A1 | 1/2002 | Cornish |
| 2003/0162249 A1 | 8/2003 | Gray et al. |
| 2013/0059359 A1 | 3/2013 | Wagner |
| 2014/0286987 A1 | 9/2014 | Spencer et al. |
| 2015/0056159 A1 | 2/2015 | Kontermann et al. |
| 2015/0086576 A1 | 3/2015 | Ploegh et al. |

FOREIGN PATENT DOCUMENTS

| | | |
|---|---|---|
| WO | WO2004046733 A1 | 6/2004 |
| WO | WO2015150771 | 10/2015 |

OTHER PUBLICATIONS

Rossi et al., Nature 20: 389-393 (Year: 1998).*
Shah et al., Genesis 45(4): 194-199 (Year: 2007).*
Balciunas, et al., "Harnessing a High Cargo-Capacity Transposon for Genetic Applications in Vertebrates," PLoS Genetics, vol. 2, No. 11, 2006, 10 pages.
Balzi & Goffeau, "Yeast multidrug resistance: the PDR network," J. Bioenerg. Biomembr., vol. 27, No. 1, 1995, pp. 71-76.
Banaszynski, et al., "Characterizatoin of the FKBP.Rapamycin.FRB ternary complex," J. Am. Chem. Soc., vol. 127, No. 13, 2005, pp. 4715-4721.
Braselmann, et al., "A selective transcriptional induction system for mammalian cells based on Ga14-estrogen receptor fusion proteins", PNAS, vol. 90, No. 5, 1993, pp. 1657-1661.
Brown, et al., "lac repressor can regulate expression from a hybrid SV40 early promoter containing a lac operator in animal cells," Cell, vol. 49, No. 5, 1987, pp. 603-612.
Bruggemann, et al., "Human Antidoby Production in Transgenic Animals," Archivum immunologiae et therapiae experimentalis, vol. 63, No. 2, 2015, pp. 101-108.
Bruter, et al., "Regulated expression systems for gene therapy," Molekuliarnaia biologiia, vol. 47, No. 3, 2013, pp. 363-387.
Burcin, et al., "A Regulatory System for Target Gene Expression," Frontiers in Bioscience, vol. 3, 1998, pp. 1-7.
Choi, et al., "Structure of the FKBP12-rapamycin complex interacting with the binding domain of human FRAP," Science, vol. 273, No. 5272, 1996, pp. 239-242.
Clackson, et al., "Redesigning an FKBP-ligand interface to generate chemical dimerizers with novel specificity", PNAS, vol. 95, 1998, pp. 10437-10442.

(Continued)

*Primary Examiner* — Phuong Huynh
(74) *Attorney, Agent, or Firm* — Lee & Hayes P.C.

(57) ABSTRACT

Methods to create chemically-induced dimerizing (CID) protein systems and uses thereof are described. The methods utilize antibody binding domain dimerizing proteins. The created systems can be used to regulate cellular events such as gene expression, receptor signaling and cell death to effectuate a variety of clinically relevant treatment outcomes.

18 Claims, 22 Drawing Sheets

Specification includes a Sequence Listing.

(56) References Cited

OTHER PUBLICATIONS

Clemons, et al., "Synthesis of Calcineurin-Resistant Derivatives of FK506 and Selection of Compensatory Receptors," Chemistry & Biology, 2002, vol. 9, No. 1, pp. 49-61.
DeRose, et al., "Manipulating signaling at will: chemically-inducible dimerization (CID) techniques resolve problems in cell biology," Pflugers Arch., vol. 465, No. 3, 2013, pp. 409-417.
Di Stasi, et al., "Inducible Apoptosis as a Safety Switch for Adoptive Cell Therapy," The New England Journal of Medicine, vol. 365, No. 18, 2011, pp. 1673-1683.
Ding, et al., "Efficient Transposition of the piggyBac (PB) Transposon in Mammalian Cells and Mice," Cell, vol. 122, No. 3, 2005, pp. 269-277.
Edwards, et. al., "The Remarkable Flexibility of the Human Antibody Repertoire; Isolation of Over One Thousand Different Antibodies to a Single Protein, BLyS" J Mol Biol, vol. 334, 2003, pp. 103-118.
Office Action dated Mar. 19, 2020 for European Patent Application No. 16858357.3, 6 pages.
Extended European Search Report dated Apr. 1, 2019 for European Application No. 16858357.3, 9 pages.
Favre, et al., "Lack of an Immune Response against the Tetracycline-Dependent Transactivator Correlates with Long-Term Doxycycline-Regulated Transgene Expression in Nonhuman Primates after Intramuscular Injection of Recombinant Adeno-Associated Virus," J. of Virology, vol. 76, No. 22, 2002, pp. 11605-11611.
Fussenegger, et al., "Streptogramin-based gene regulation systems for mammalian cells," Nature biotechnology, vol. 18, No. 11, 2000, pp. 1203-1208.
Gallinari, et al., "A Functionally Orthogonal Estrogen Receptor-Based Transcription Switch Specifically Induced by a Nonsteroid Synthetic Ligand", Chemistry & Biology, vol. 12, No. 8, pp. 883-893.
Gossen, et al., "Tight control of gene expression in mammalian cells by tetracycline-responsive promoters," PNAS, vol. 89, 1992, pp. 5547-5551.
Gossen, et al., "Transcriptional activation by tetracyclines in mammalian cells," Science, vol. 268, No. 5218, 1995, pp. 1766-1769.
Hulme & Trevethick, "Ligand binding assays at equilibrium: validation and interpretation" Br. J. Pharmacol., vol. 161, No. 6, 2010, pp. 1219-1237.
Hwang & Foote, "Immunogenicity of engineered antibodies," Methods, vol. 36, No. 1, 2005, pp. 3-10.
Kay, et al., "High-throughput Bioinylation of Proteins," Methods Mol. Biol., vol. 498, 2009, pp. 185-196.
Komita, et al., "Conditional interleukin (IL)-12 gene therapy promotes safe and effective anti-tumor immunity", Cancer Gene Ther., vol. 16, No. 12, 2009, pp. 883-891.
Koybayashi, et al., "Antibody engineering towar high- sensitivity high-throughput immunosensing of small molecules," Analyst, vol. 136, 2011, pp. 642-651.
Kuramochi, et al., "Humanization and Simultaneous optimization of monoclonal antibody," Methods Mol. Biol., vol. 1060, 2014, pp. 123-137.
Le Guiner, et al., "Transgene Regulation Using the Tetracycline-Inducible TetR-KRAB System after AAV-Mediated Gene Transfer in Rodents and Nonhuman Primates", PLoS One, vol. 9, No. 9, 2014, 10 pages.
Liu, et al., "A bioorthogonal small-molecule-switch system for controlling protein function in live cells," Ang. Chem. Int. Ed. Engl., vol. 53, No. 38, 2014, pp. 10049-10055.
Liu, et al., "FKBP12 regulates the localization and processing of amyloid precursor protein in human cell lines," J. Biosci., vol. 39, No. 1, 2014, pp. 85-95.
Lloyd, et. al., "Modelling the human immune response: performance of a 10 11 human antibody repertoire against a broad panel of therapeutically relevant antigens", Protein Engineering, Design & Selection, vol. 22 Iss. 3, 2009, pp. 159-168.
Long, et al., "On-Demand Targeting: Investigating Biology with Proximity-Directed Chemistry," J. Am. Chem. Soc., vol. 138, No. 11, 2016, pp. 3610-3622.
Mack, et al. "Exact analysis of ligand-induced dimerization of monomeric receptors," Anal. Chem., vol. 80, No. 14, 2008, 5550-5555, 12 pages.
Magari, et al., "Pharmacologic Control of a Humanized Gene Therapy System Implanted into Nude Mice," J. Clin. Invest., vol. 100, No. 11, 1997, pp. 2865-2872.
Mata, "Solid-phase and combinatorial synthesis in beta-lactam chemistry," Curr. Pharm. Des., vol. 5, No. 11, 1999, pp. 955-964.
Miyazaki, et al., "Expression vector system based on the chicken beta-actin promoter directs efficient production of interleukin-5," Gene, vol. 79, No. 2, 1989, pp. 269-277.
Mullick, et al., "The cumate gene-switch: a system for regulated expression in mammalian cells", BMC Biotechnology, vol. 6, No. 43, 2006, 18 pages.
Naidoo and Young, "Gene Regulation Systems for Gene Therapy Applications in the Central Nervous System," Neurology Research International, vol. 2012, 2011, 10 pages.
No, et al., "Ecdysone-inducible gene expression in mammalian cells and transgenic mice," PNAS, vol. 93, No. 8, 1996, pp. 3346-3351.
Nor, et al., "Ablation of microvessels in vivo upon dimerization of Caspase-9," Gene Therapy, vol. 9, No. 7, 2002, pp. 444-451.
Nordstrom, "The antiprogestin-dependent GeneSwitch system for regulated gene therapy," Steroids, vol. 68, No. 10-13, 2003, pp. 1085-1094.
Office Action dated Nov. 12, 2019 for U.S. Appl. No. 15/770,433, 11 Pages.
Office Action dated Apr. 23, 2020 for U.S. Appl. No. 15/770,433, 13 pages.
Olichon, et al., "Selection of Genetically Encoded Fluorescent Single Domain Antibodies Engineered for Efficient Expression in *Escherichia coli*," J. Biol. Chem., vol. 282, No. 50, 2007, pp. 36314-3632.
Olimpieri, et al., "Tabhu: tools for antibody humanization," Bioinformatics, vol. 31, No. 3, 2015, pp. 434-435.
Palli, et al., "Improved ecdysone receptor-based inducible gene regulation system," Eur. J. Biochem., vol. 270, No. 6, 2003, pp. 1308-1315.
Parker, et. al., "An Antibody-Recruiting Small Molecule That Targets HIV gp120", J. Am. Chem. Soc., vol. 131, No. 45, 2009, pp. 16392-16394.
Pastor-Navarro, et al., "Synthesis of haptens and development of a sensitive immunoassay for tetracycline residues. Application to honey samples," Anal. Chim. Acta, vol. 594, No. 2, 2007, pp. 211-218.
Search Report and Written Opinion dated Feb. 15, 2017 for International Application No. PCT/US16/58237.
Office Action dated Dec. 1, 2022 for Canadian Patent Application No. 3,002,903, 6 pages.
Philibert, et al., "A focused antibody library for selecting scFvs expressed at high levels in the cytoplasm," BMC Biotechnology, vol. 7, 2007, 17 pages.
Pollock, et al., "Delivery of a stringent dimerizer-regulated gene expression system in a single retroviral vector", PNAS, vol. 94, No. 24, 2000, pp. 13221-13226.
Rivera, et al., "A humanized system for pharmacologic control of gene expression," Nat. Med., vol. 2, No. 9, 1996, pp. 1028-1032.
Rudikoff, et. al., "Single amino acid substitution altering antigen-binding specificity", Proc Natl Acad Sci USA, vol. 79, Mar. 1982, pp. 1979-1983.
Safdari, et al., "Antibody humanization methods—a review and update," Biotechnol. Genet. Eng. Rev., vol. 29, 2013, pp. 175-186.
Seeber, et. al., "A Robust High Throughput Platform to Generate Functional Recombinant Monoclonal Antibodies Using Rabbit B Cells from Peripheral Blood," PLoS One, vol. 9, No. 2, 2014, 26 pages.
Spencer, et al., "Controlling signal transduction with synthetic ligands," Science, vol. 262, No. 5136, 1993, pp. 1019-1024.
Straathof, et al., "An inducible caspase 9 safety switch for T-cell therapy," Blood, vol. 105, No. 11, 2005, pp. 4247-4254.

(56) References Cited

OTHER PUBLICATIONS

Suhr, et al., "High level transactivation by a modified Bombyx ecdysone receptor in mammalian cells without exogenous retinoid X receptor," PNAS, vol. 95, No. 14, 1998, pp. 7999-8004.

Thomis, et al., "A Fas-based suicide switch in human T cells for the treatment of graft-versus-host disease," Blood, vol. 97, No. 5, 2001, pp. 1249-1257.

Toleikis & Frenzel, "Cloning single-chain antibody fragments (ScFv) from hybridoma cells," Methods Mol. Biol., vol. 907, 2012, pp. 59-71.

Toromanoff, et al., "Lack of Immunotoxicity After Regional Intravenous (RI) Delivery of rAAV to Nonhuman Primate Skeletal Muscle," Molecular Therapy, vol. 18, No. 1, 2010, pp. 151-160.

Tsurushita, et al., "Design of humanized antibodies: from anti-Tac to Zenapax," Methods, vol. 36. No. 1, 2005, pp. 69-83.

Van Acker, et al., "The 12 kDa FK506-binding protein, FKBP12, modulates the Ca2+-flux properties of the type-3 ryanodine receptor," J. Cell Sci., vol. 117, No. 7, 2004, pp. 1129-11237.

Vincke, et al., "General Strategy to Humanize a Camelid Single-domain Antibody and Identification of a Universal Humanized Nanobody Scaffold," J. Biol. Chem., vol. 284, No. 5, 2009, pp. 3273-3284.

Voss, et al., "Inter-relationship between immunoglobulin idiotype and metatype," Mol. Immunol., vol. 26, No. 10, 1989, pp. 971-977.

Weber, et al., "Macrolide-based transgene control in mammalian cells and mice," Nature Biotechnology, vol. 20, No. 9, 2002, pp. 901-907.

Weidner, et al., "Molecular Stabilization Effects of Interactions between Anti-metatype Antibodies and Liganded Antibody," J. Biol. Chem., vol. 267, No. 15, 1992, pp. 10281-10288.

Wesolowski, et al., "Single domain antibodies: promising experimental and therapeutic tools in infection and immunity," Medical Microbiology and Immunology, vol. 198, No. 3, 2009, pp. 157-174.

Yang & Rader, "Cloning, expression, and purification of monoclonal antibodies in scFV-Fc format," Methods Mol. Biol., vol. 901, 2012, pp. 209-232.

* cited by examiner

FIG. 9, cont.
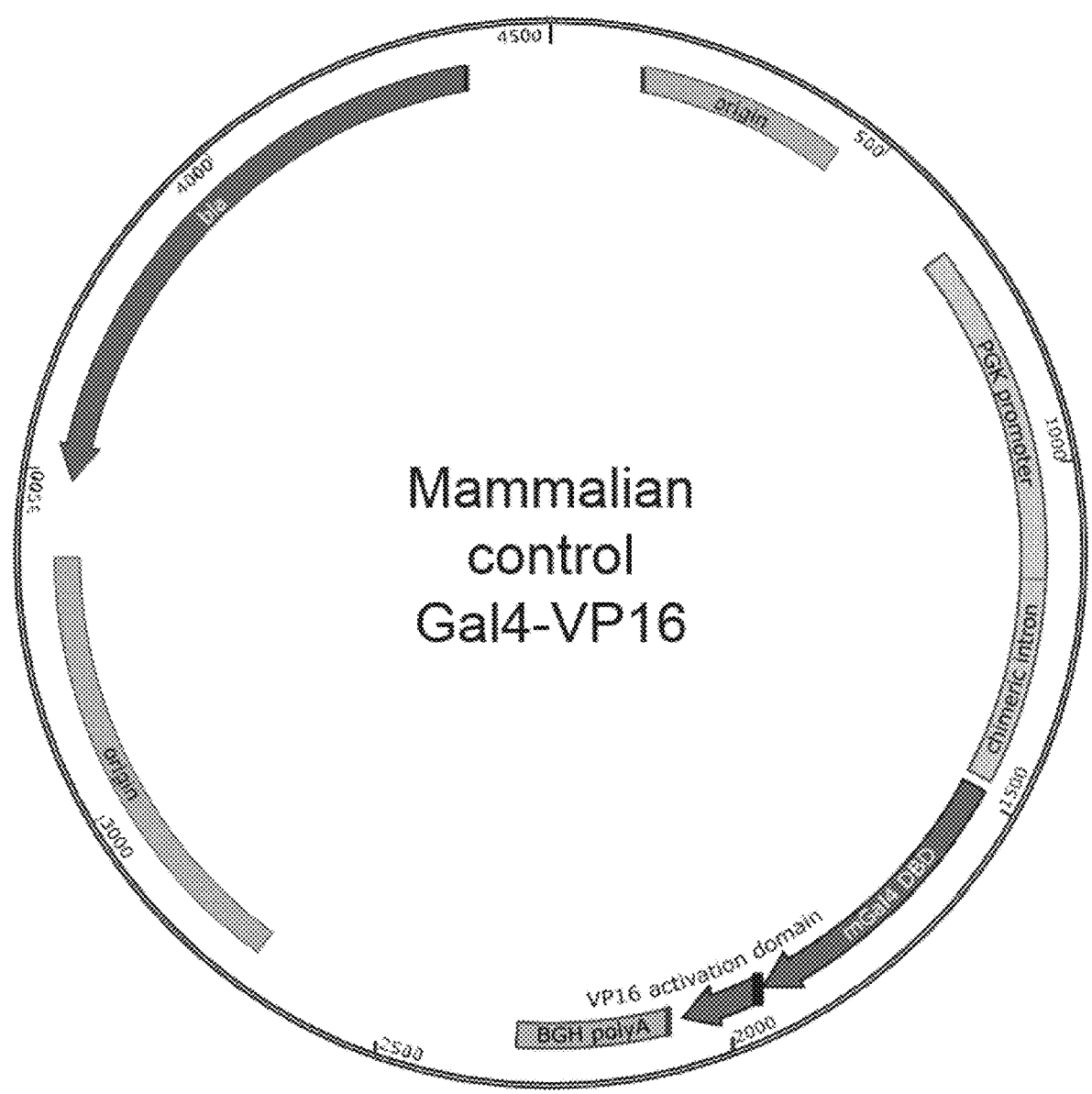

FIG. 10A

| Camel/Llama VHH | Primer Name | Sequence |
|---|---|---|
| 1st Round PCR | Forward | GTCCTGGCTGCTCTTCTACAAGG (SEQ ID NO: 30) |
| | Reverse | GGTACGTGCTGTTGAACTGTTCC (SEQ ID NO: 31) |
| 2nd Round PCR | Forward | NNNNNNNNNGCGGCCGCCACCATGGATGTGCAGCTGCAGGAGTCTGGRGGAGG (SEQ ID NO: 32) OR/ALTERNATIVE NNNNNNNNNGCGGCCGCCACCATGGCTSAKGTGCAGCTGGTGGAGTCTGG (SEQ ID NO: 33) |
| | Reverse | NNNNNNNNNCTGGAGACGGTGACCTGGGT (SEQ ID NO: 34) |

FIG. 10B

| Alpaca VHH | Primer Name | Sequence |
|---|---|---|
| 1st Round PCR | Forward | GGTGGTCCTGGCTGC (SEQ ID NO: 35) |
| | Reverse | GATCACTAGTGGGGTCTTCGCTGTGGTCG (SEQ ID NO: 36) |
| 2nd Round PCR | Forward | NNNNNNNNNGCGGCCGCCACCATGGCTCAGKTGCAGCTCGTGGAGTCNGGNGG (SEQ ID NO: 37) |
| | Reverse | NNNNNNNNNCTGGAGACGGTGACCTGGT (SEQ ID NO: 38) |

FIG. 10C

| Genomic DNA amplification primers | Primer Name | Sequence |
|---|---|---|
| | CAG promoter For (mammalian vector) | CTACAGCTCCTGGGCAACGTG (SEQ ID NO: 39) |
| | TdTomato Rev (mammalian and yeast vector) | TGATCACCTCCTCGCCCTTGCTCAC (SEQ ID NO: 40) |
| | TDH3 promoter For (yeast vector) | ACACCAGAACTTAGTTTCGACTCG (SEQ ID NO: 41) |
| | p65 AD Rev (mammalian vector) | GGCAGGTACTGGAACTCCATCG (SEQ ID NO: 42) |

FIG. 10D

| Bacterial expression vector sequencing | Primer Name | Sequence |
|---|---|---|
| | T7 promoter primer | TAATACGACTCACTATAGG (SEQ ID NO: 43) |
| | Reverse sequencing primer | GTGGTGGTGTTCATGCCATTC (SEQ ID NO: 44) |

FIG. 11

| Human scFV | Primer Name | Sequence |
|---|---|---|
| VH primers, 5' sense, long linker | | |
| | HSCVH1-FL | GGTGGTTCCTCTAGATCTTCCTCCTCTGGTGGCGGTGGCTCGGGCGGTGGTGGGCAGGTGCAGCTGGTGCAGTCTGG (SEQ ID NO: 45) |
| | HSCVH2-FL | GGTGGTTCCTCTAGATCTTCCTCCTCTGGTGGCGGTGGCTCGGGCGGTGGTGGGCAGATCACCTTGAAGGAGTCTGG (SEQ ID NO: 46) |
| | HSCVH35-FL | GGTGGTTCCTCTAGATCTTCCTCCTCTGGTGGCGGTGGCTCGGGCGGTGGTGGGGAGGTGCAGCTGGTGSAGTCTGG (SEQ ID NO: 47) |
| | HSCVH3a-FL | GGTGGTTCCTCTAGATCTTCCTCCTCTGGTGGCGGTGGCTCGGGCGGTGGTGGGGAGGTGCAGCTGKTGGAGTCTG (SEQ ID NO: 48) |
| | HSCVH4-FL | GGTGGTTCCTCTAGATCTTCCTCCTCTGGTGGCGGTGGCTCGGGCGGTGGTGGGCAGGTGCAGCTGCAGGAGTCGGG (SEQ ID NO: 49) |
| | HSCVH4a-FL | GGTGGTTCCTCTAGATCTTCCTCCTCTGGTGGCGGTGGCTCGGGCGGTGGTGGGCAGGTGCAGCTACAGCAGTGGGG (SEQ ID NO: 50) |
| VH primers, 3' reverse long linker | | |
| | HSCG1234-B (corresponding to IgG isotypes 1-4) | GCCACTAGTGAGTCGACACGACCGATGGGCCCTTGGTGGARGC (SEQ ID NO: 51) |
| | HSCM-B (corresponding to CH1 domain of human IgM) | GCCACTAGTGAGTCGACACAAGGGTTGGGGCGGATGCACTCCC (SEQ ID NO: 52) |
| | HSCA-B (corresponding to $C_H1$ domain of human IgA) | GCCACTAGTGAGTCGACACGACCTTGGGGCTGGTCGGGGATGC (SEQ ID NO: 53) |
| | HSCD-B (corresponding to $C_H1$ domain of human IgD) | GCCACTAGTGAGTCGACACCACATCCGGAGCCTTGGTGGGTGC (SEQ ID NO: 54) |
| | HSCE-B (corresponding to $C_H1$ domain of human IgE) | GCCACTAGTGAGTCGACACGACGGATGGGCTCTGTGTGGAGGC (SEQ ID NO: 55) |

FIG. 11, cont.

| | | |
|---|---|---|
| Vκ primers, 5' sense long linker | | |
| | HSCK1-F | AAGCGGCCGCCACCATGGTGCAGATGACCCAGTCTCC (SEQ ID NO: 56) |
| | HSCK24-F | AAGCGGCCGCCACCATGGTGGTGATGACYCAGTCTCC (SEQ ID NO: 57) |
| | HSCK3-F | AAGCGGCCGCCACCATGGTGGTGWTGACRCAGTCTCC (SEQ ID NO: 58) |
| | HSCK5-F | AAGCGGCCGCCACCATGGTGACACTCACGCAGTCTCC (SEQ ID NO: 59) |
| Vκ primers, 3' reverse, long linker | | |
| | HSCJK14o-B | GGAAGATCTAGAGGAACCACCTTTGATYTCCACCTTGGTCCC (SEQ ID NO: 60) |
| | HSCJK2o-B | GGAAGATCTAGAGGAACCACCTTTGATCTCCAGCTTGGTCCC (SEQ ID NO: 61) |
| | HSCJK3o-B | GGAAGATCTAGAGGAACCACCTTTGATATCCACTTTGGTCCC (SEQ ID NO: 62) |
| | HSCJK5o-B | GGAAGATCTAGAGGAACCACCTTTAATCTCCAGTCGTGTCCC (SEQ ID NO: 63) |
| Vλ primers, 5' sense, long linker | | |
| | HSCLam1a | AAGCGGCCGCCACCATGGTGGTGBTGACGCAGCCGCCCTC (SEQ ID NO: 64) |
| | HSCLam1b | AAGCGGCCGCCACCATGGTGGTGCTGACTCAGCCACCCTC (SEQ ID NO: 65) |
| | HSCLam2 | AAGCGGCCGCCACCATGGTGGCCCTGACTCAGCCTCCCTCCGT (SEQ ID NO: 66) |
| | HSCLam3 | AAGCGGCCGCCACCATGGTGCTGACTCAGCCACCCTCAGTGTC (SEQ ID NO: 67) |
| | HSCLam4 | AAGCGGCCGCCACCATGGTGGTGCTGACTCAATCGCCCTC (SEQ ID NO: 68) |
| | HSCLam6 | AAGCGGCCGCCACCATGGTGATGCTGACTCAGCCCCACTC (SEQ ID NO: 69) |
| | HSCLam78 | AAGCGGCCGCCACCATGGTGGTGGTGACYCAGGAGCCMTC (SEQ ID NO: 70) |
| | HSCLam9 | AAGCGGCCGCCACCATGGTGGTGCTGACTCAGCCACCTTC (SEQ ID NO: 71) |
| | HSCLam10 | AAGCGGCCGCCACCATGGTGGGGCAGACTCAGCAGCTCTC (SEQ ID NO: 72) |

FIG. 11, cont.

| Vλ primers, 3' reverse, long linker | | |
|---|---|---|
| | HSCJLam1236 | GGAAGATCTAGAGGAACCACCGCCTAGGACGGTCASCTTGGTSCC (SEQ ID NO: 73) |
| | HSCJLam4 | GGAAGATCTAGAGGAACCACCGCCTAAAATGATCAGCTGGGTTCC (SEQ ID NO: 74) |
| | HSCJLam57 | GGAAGATCTAGAGGAACCACCGCCGAGGACGGTCAGCTSGGTSCC (SEQ ID NO: 75) |
| Overlap extension primers | | |
| | RSC-F (sense) | NNNNNNNNNAAGCGGCCGCCACCATGGTG (SEQ ID NO: 76) |
| | RSC-B (reverse) | NNNNNNNNNGCCACTAGTGAGTCGACAC (SEQ ID NO: 77) |

FIG. 12

| Human Heavy Chain Only (VHH) | Primer Name | Sequence |
|---|---|---|
| VH primers, 1st Round For | | |
| | VH1.1b 1° | CAGGTKCAGCTGGTGCAGTCTGGGGC (SEQ ID NO: 78) |
| | VH1.2 1° | CAGGTCCAGCTTGTGCAGTCTGG (SEQ ID NO: 79) |
| | VH1.3 1° | CAGGTCCAGCTGGTACAGTCTGG (SEQ ID NO: 80) |
| | VH1.4 1° | CARATGCAGCTGGTGCAGTCTGG (SEQ ID NO: 81) |
| | VH1.5 1° | GAGGTCCAGCTGGTACAGTCTGG (SEQ ID NO: 82) |
| | VH2 1° | CAGRTCACCTTGAAGGAGTCTGG (SEQ ID NO: 83) |
| | VH3-1L 1° | GAGGTGCAGCTGGTGGAGTCTGGGGGAGGCTTGGTCCAG (SEQ ID NO: 84) |
| | VH3-2L 1° | CAGGTGCAGCTGGTGGAGTCTGGGGGAGGCTTGGTCAAG (SEQ ID NO: 85) |
| | VH3-3L 1° | GAGGTGCAGCTGGTGGAGTCTGGGGGAGGCTTGGTAAAG (SEQ ID NO: 86) |
| | VH3-4L 1° | GAGGTGCAGCTGGTGGAGTCTGGGGGAGGTGTGGTACGG (SEQ ID NO: 87) |
| | VH3-5L 1° | CAGGTGCAGCTGGTGGAGTCTGGGGGAGGCGTGGTCCAG (SEQ ID NO: 88) |
| | VH3-6L 1° | GAGGTGCAGCTGGTGGAGACTGGAGGAGGCTTGATCCAG (SEQ ID NO: 89) |
| | VH4-1L 1° | CAGGTGCAGCTGCAGGAGTCGGGCCCAGGACTGGTGAAG (SEQ ID NO: 90) |
| | VH4-2L 1° | CAGCTGCAGCTGCAGGAGTCGGGCCCAGGACTGGTGAAG (SEQ ID NO: 91) |
| | VH4-3L 1° | CAGGTGCAGCTACAGCAGTGGGGCGCAGGACTGTTGAAG (SEQ ID NO: 92) |
| | VH5.1b 1° | GAGGTGCAGCTGGTGCAGTCTGGAGCA (SEQ ID NO: 93) |
| | VH5.2b 1° | GAAGTGCAGCTGGTGCAGTCTGGAGCA (SEQ ID NO: 94) |
| | VH6 1° | CAGGTACAGCTGCAGCAGTCAGG (SEQ ID NO: 95) |

FIG. 12, cont.

| VH primers, 2nd Round For | | |
|---|---|---|
| | VH1.1b 2° | NNNNNNNNNAAGCGGCCGCCACCATGGCCCAGGTKCAGCTGGTGCAG (SEQ ID NO: 96) |
| | VH1.2 2° | NNNNNNNNNAAGCGGCCGCCACCATGGCCCAGGTCCAGCTTGTGCAG (SEQ ID NO: 97) |
| | VH1.3 2° | NNNNNNNNNAAGCGGCCGCCACCATGGCCCAGGTCCAGCTGGTACAG (SEQ ID NO: 98) |
| | VH1.4 2° | NNNNNNNNNAAGCGGCCGCCACCATGGCCCARATGCAGCTGGTGCAG (SEQ ID NO: 99) |
| | VH1.5 2° | NNNNNNNNNAAGCGGCCGCCACCATGGCGAGGTCCAGCTGGTACAG (SEQ ID NO: 100) |
| | VH2 2° | NNNNNNNNNAAGCGGCCGCCACCATGGCCCAGRTCACCTTGAAGGAG (SEQ ID NO: 101) |
| | VH3-1,3,4,6L 2° | NNNNNNNNNAAGCGGCCGCCACCATGGCCGAGGTGCAGCTGGTGGAG (SEQ ID NO: 102) |
| | VH3-2,5L 2° | NNNNNNNNNAAGCGGCCGCCACCATGGCCCAGGTGCAGCTGGTGGAG (SEQ ID NO: 103) |
| | VH4-1L 2° | NNNNNNNNNAAGCGGCCGCCACCATGGCCCAGGTGCAGCTGCAGGAG (SEQ ID NO: 104) |
| | VH4-2L 2° | NNNNNNNNNAAGCGGCCGCCACCATGGCCCAGCTGCAGCTGCAGGAG (SEQ ID NO: 105) |
| | VH4-3L 2° | NNNNNNNNNAAGCGGCCGCCACCATGGCCCAGGTGCAGCTACAGCAG (SEQ ID NO: 106) |
| | VH5.1b 2° | NNNNNNNNNAAGCGGCCGCCACCATGGCGAGGTGCAGCTGGTGCAG (SEQ ID NO: 107) |
| | VH5.2b 2° | NNNNNNNNNAAGCGGCCGCCACCATGGCCGAAGTGCAGCTGGTGCAG (SEQ ID NO: 108) |
| | VH6 2° | NNNNNNNNNAAGCGGCCGCCACCATGGCCCAGGTACAGCTGCAGCAG (SEQ ID NO: 109) |

FIG. 12, cont.

| VH primers, First Round Reverse | | |
|---|---|---|
| | JH1-2 1° | TGAGGAGACRGTGACCAGGGTG (SEQ ID NO: 110) |
| | JH3 1° | TGAAGAGACGGTGACCATTGT (SEQ ID NO: 111) |
| | JH4-5 1° | TGAGGAGACGGTGACCAGGGTT (SEQ ID NO: 112) |
| | JH6 1° | TGAGGAGACGGTGACCGTGGTCC (SEQ ID NO: 113) |
| VH primers, Second Round Reverse | | |
| | JH1 2° | GCCACTAGTGAGTCGACACTGAGGAGACRGTGACCAG (SEQ ID NO: 114) |
| | JH3 2° | GCCACTAGTGAGTCGACACTGAAGAGACGGTGACCAT (SEQ ID NO: 115) |
| | JH4-5 2° | GCCACTAGTGAGTCGACACTGAGGAGACGGTGACCAG (SEQ ID NO: 116) |
| | JH6 2° | GCCACTAGTGAGTCGACACTGAGGAGACGGTGACCGT (SEQ ID NO: 117) |

US 11,993,794 B2

METHODS TO CREATE CHEMICALLY-INDUCED DIMERIZING PROTEIN SYSTEMS FOR REGULATION OF CELLULAR EVENTS

CROSS REFERENCE TO RELATED APPLICATION

This application is a divisional of U.S. patent application Ser. No. 15/770,433, filed on Apr. 23, 2018, now U.S. Pat. No. 10,954,500, which is a national phase of International Patent Application No. PCT/US2016/058237, filed on Oct. 21, 2016, which claims priority to U.S. Provisional Patent Application No. 62/245,756, filed Oct. 23, 2015, the entire contents of each of which are incorporated by reference herein.

REFERENCE TO SEQUENCE LISTING

The Sequence Listing associated with this application is provided in text format in lieu of a paper copy, and is hereby incorporated by reference into the specification. The name of the text file containing the Sequence Listing is 2FO7778_ST25.txt. The text file is 27.7 KB, was created on Feb. 2, 2021, and is being submitted electronically via EFS-Web.

FIELD OF THE DISCLOSURE

The present disclosure provides methods to create chemically-induced dimerizing (CID) protein systems and uses thereof. The methods utilize antibody binding domain dimerizing proteins. The created systems can be used to regulate cellular events such as gene expression, receptor signaling and cell death to effectuate a variety of clinically relevant treatment outcomes.

BACKGROUND OF THE DISCLOSURE

The ability to precisely regulate cellular events (e.g., gene expression, intracellular signaling, cell migration, cell death, etc.) in living organisms has immense potential in a variety of contexts. For example, the ability to precisely regulate cellular events can be used in human medicine to treat innumerable conditions.

Many cellular events are regulated (e.g., initiated, modulated or terminated) when proteins interact or cease interaction with each other. For example, gene expression can be initiated when a DNA binding domain protein interacts with a transcription activation domain protein. Gene expression can terminate, for example, when the interaction ceases. Cell receptor signaling can also be initiated when intracellular protein domains of a receptor interact. Cell receptor signaling can terminate, for example, when the interaction ceases. Cellular signaling pathways can also be regulated by bringing enzymes and their substrates together (such as kinases and their downstream targets). Protein degradation can be initiated by recruiting ubiquitination machinery to a target protein. Further, cell death processes can be initiated when caspase proteins interact.

Chemically-induced protein interaction (e.g., chemically induced dimerization (CID) of proteins) refers to a process whereby two proteins which do not normally interact, pair (e.g., homo- or heterodimerize) in the presence of a small molecule (e.g., a small molecule drug) [20]. The most widely used example of this technology is the FKBP12/FRB dimerization system [21, 22]. FKBP12 and FRB are human derived proteins which dimerize in the presence of the immunosuppressive small molecule drug, rapamycin. Fusion of FKBP12 to a DNA binding domain and fusion of FRB to a transcriptional activation domain produces a system where addition of rapamycin activates gene expression by recruiting the transcriptional activation domain into proximity of the promoter DNA [21]. This system was further improved by creating mutants of both FKBP12 and FRB which exclusively bind to rapamycin analogs (rapalogs) with reduced immunosuppressive activity [23, 24].

A drawback of the FKBP12/FRB system, however, is the slow dissociation rate of FKBP12 and FRB after removal of excess small molecule, leading to a slow turn off of gene expression after small molecule withdrawal [25, 26].

In addition to heterodimerization with FRB, FKBP12 can be made to homodimerize with itself by use of a symmetrical ligand FK1012 or its derivatives [28, 29]. In one example of a use of this system, a fusion of FKBP12 with a fragment of human Fas or Caspase 9 proteins creates inducible caspase switches. Addition of the small molecule to cells expressing either fusion protein results in a caspase cascade and cell death [30, 31]. This system is currently in human trials as a method to control graft versus host disease in modified human T-cell therapies [32, 33].

In addition to FKB12 and FRB, CID systems have also been created with the proteins Calcineurin (which binds to the drug FK506) and DHFR (which binds to the drug trimethoprim) [27].

Limitations exist with current CID technologies. First, the small molecules used to control the systems often have undesirable characteristics. Rapamycin and FK506 are potent immunosuppressive drugs and are not suitable for use in gene therapy applications. Although modified small molecules without immunosuppressive activity can be synthesized (as with "rapalogs"), each drug still must be evaluated for safety by the U.S. Food & Drug Administration (FDA) approval process. Additionally, it is not clear from the outset that small molecules with an ideal set of characteristics can be found, potentially wasting time in costly drug development. Second, as the CID proteins in these systems are derived from human proteins with normal cellular functions, their overexpression may alter cell physiology. For example, overexpression of FKBP12 has been shown to alter calcium influx in muscle and processing of the Alzheimer's associated APP protein in neurons [34, 35]. These systems can also have poor ON/OFF kinetics and thus cannot be regulated with enough precision. Currently existing systems can also cause off target effects on endogenous gene expression.

SUMMARY OF THE DISCLOSURE

The present disclosure provides methods to create improved chemically induced dimerization (CID) systems. The disclosed CID systems are improved because they use one or more of 1) human derived or humanized proteins with low or no immunogenicity; 2) proteins with no known intracellular functions so that on-going cell physiology is minimally impacted; and 3) small molecule inducers that are already FDA approved for human use and have good pharmacological characteristics for the intended application. The present disclosure also provides uses of the created systems.

In particular embodiments, at least one of the proteins of the CID system is an antibody binding domain. In particular embodiments, both proteins of the CID system are antibody binding domains. The first protein binds a selected small molecule. The second protein binds the first protein, but only when it is bound to the small molecule. Thus, interaction between the proteins is controlled by administration and removal of the small molecule.

BRIEF DESCRIPTION OF THE FIGURES

FIG. 1A) Transcriptional control of gene expression using CID. One protein is fused to a DNA binding domain and the other to a transcriptional activation domain. Addition of the small molecule causes dimerization and recruits the activation domain into proximity of the DNA binding domain and results in transcription of target genes containing cognate DNA binding sites within the promoter. FIG. 1B) Control of cell signaling using CID. Cellular receptors which depend on dimerization for activation of downstream signaling can be fused to the dimerizing protein pair. Addition of the small molecule causes receptor dimerization and results in signaling. FIG. 1C) Control of cellular apoptosis using CID. Initiator caspases depend upon dimerization for cleavage and activation. These caspases can be fused to the dimerizing proteins such that addition of the small molecule results in caspase dimerization and activation, resulting in cell apoptosis.

FIG. 2A) Dimeric or heavy chain only antibodies are raised against a chosen small molecule hapten by immunization of a target animal. FIG. 2B) The binding domains of anti-hapten specific antibodies are isolated in the form of single chain antibodies (scFV) or heavy chain only VHH. These binding domains are then further screened and optimized to select for high specificity and affinity. FIG. 2C) VHH or scFV complexed with small molecule is used to immunize target animals to generate anti-metatype antibodies. FIG. 2D) The binding domains of specific anti-metatype antibodies are isolated and optimized to select for specificity and affinity. In particular embodiments, these antibody binding domain/anti-metatype antibody binding domain pairs form the two proteins of the CID system.

FIG. 4A) Selection scheme for anti-small molecule binding VHH or scFV. Individual VHH or scFV (represented by the differently shaded boxes) can be expressed intracellularly in a large cell library. The cells can be incubated with a small molecule-fluorophore conjugate to allow binding of the small molecule by specific VHH or scFV. The cells can be then washed to remove excess small molecule and sorted by flow cytometry, selecting cells that retain the small molecule-fluorophore due to VHH or scFV binding. FIG. 4B) Selection scheme for anti-metatype VHH or scFV using a two-hybrid approach. Individual VHH or scFV can be expressed as fusions with a transcriptional activation domain in a large cell library. These cells can also express an anti-small molecule binding VHH or scFV fused to a DNA binding domain and a TdTomato transcriptional reporter. In the presence of small molecule, specific anti-metatype VHH or scFV dimerize with the partner antibody and can cause transcription of the TdTomato reporter. Non-specific VHH or scFV do not dimerize and no transcription occurs.

FIG. 5A) Exemplary mammalian screening vector. FIG. 5B) Exemplary yeast screening vector.

FIG. 7A) Exemplary mammalian Gal4 DBD vector. FIG. 7B) Exemplary yeast Gal4 DBD vector.

FIG. 8A) Exemplary mammalian activation domain vector. FIG. 8B) Exemplary yeast activation domain receptor.

FIGS. 10A-10D. Exemplary primers. FIG. 10A) Exemplary camel/llama VHH primers. FIG. 10B) Exemplary alpaca VHH primers. FIG. 10C) Exemplary genomic DNA amplification primers. FIG. 10D) Exemplary bacterial expression vector sequencing primers.

FIG. 11. Exemplary human scFV primers.

FIG. 12. Exemplary human VHH primers.

Figure 1A:
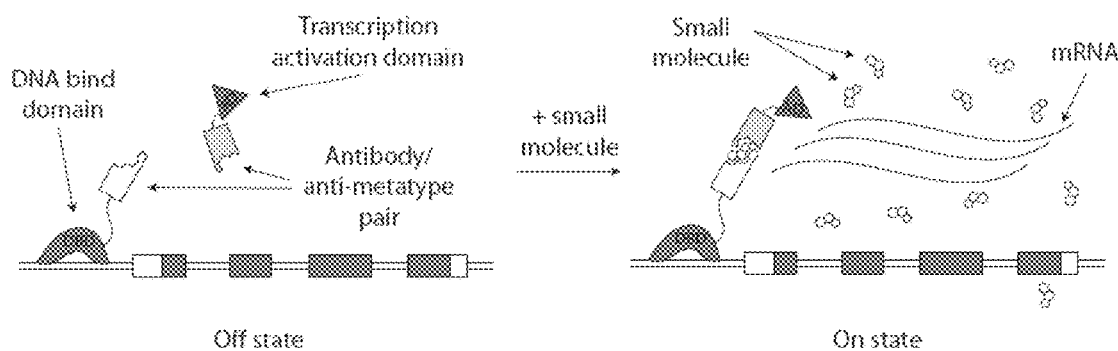
FIGS. 1A-1C. Gene and cellular control using chemically-induced dimerization (CID) of proteins.

In exemplary vector FIGs., salient features are labeled by shaded boxes and arrows. The DNA sequence of the multiple cloning site into which the VHH or scFV are ligated is shown along with the translated protein sequence of the resulting VHH or scFV fusion. Restriction enzyme cutting sites are labeled.

DETAILED DESCRIPTION

The ability to precisely regulate cellular events (e.g., gene expression, intracellular signaling, cell migration, cell death, etc.) in living organisms has immense potential in a variety of contexts. For example, the ability to precisely regulate cellular events can be used in human medicine to treat innumerable conditions.

Many cellular events are regulated (e.g., initiated, modulated or terminated) when proteins interact or cease interaction with each other. For example, gene expression can be initiated when a DNA binding domain protein interacts with a transcription activation domain protein. Gene expression can terminate, for example, when the interaction ceases. Cell receptor signaling can also be initiated when intracellular protein domains of a receptor interact. Cell receptor signaling can terminate, for example, when the interaction ceases. Cellular signaling pathways can also be regulated by bringing enzymes and their substrates together (such as kinases and their downstream targets). Protein degradation can be initiated by recruiting ubiquitination machinery to a target protein. Further, cell death processes can be initiated when caspase proteins interact.

Chemically-induced protein interaction (e.g., chemically induced dimerization (CID) of proteins) refers to a process whereby two proteins which do not normally interact, pair (e.g., homo- or heterodimerize) in the presence of a small molecule (e.g., a small molecule drug) [20]. The most widely used example of this technology is the FKBP12/FRB dimerization system [21, 22]. FKBP12 and FRB are human derived proteins which dimerize in the presence of the immunosuppressive small molecule drug, rapamycin. Fusion of FKBP12 to a DNA binding domain and fusion of FRB to a transcriptional activation domain produces a system where addition of rapamycin activates gene expression by recruiting the transcriptional activation domain into proximity of the promoter DNA [21]. The system was further improved by creating mutants of both FKBP12 and FRB which exclusively bind to rapamycin analogs (rapalogs) with reduced immunosuppressive activity [23, 24].

A drawback of the FKBP12/FRB system, however, is the slow dissociation rate of FKBP12 and FRB after removal of excess small molecule, leading to a slow turn off of gene expression after small molecule withdrawal [25, 26].

In addition to heterodimerization with FRB, FKBP12 can be made to homodimerize with itself by use of a symmetrical ligand FK1012 or its derivatives [28, 29]. In one example of a use of this system, a fusion of FKBP12 with a fragment of human Fas or Caspase 9 proteins creates inducible caspase switches. Addition of the small molecule to cells expressing either fusion protein results in a caspase cascade and cell death [30, 31]. This system is currently in human trials as a method to control graft versus host disease in modified human T-cell therapies [32, 33]. In addition to FKB12 and FRB, CID systems have also been created with the proteins Calcineurin (which binds to the drug FK506) and DHFR (which binds to the drug trimethoprim) [27].

Limitations exist with current CID technologies. First, the small molecules used to control the systems often have undesirable characteristics. Rapamycin and FK506 are potent immunosuppressive drugs and are not suitable for use in gene therapy applications. Although modified small molecules without immunosuppressive activity can be synthesized (as with "rapalogs"), each drug still must be evaluated for safety by the FDA approval process. Additionally, it is not clear from the outset that small molecules with an ideal set of characteristics can be found, potentially wasting time in costly drug development. Second, as the CID proteins in these systems are derived from human proteins with normal cellular functions, their overexpression may alter cell physiology. For example, overexpression of FKBP12 has been shown to alter calcium influx in muscle and processing of the Alzheimer's associated APP protein in neurons [34, 35]. These systems can also have poor ON/OFF kinetics and thus cannot be regulated with enough precision. Currently existing systems can also cause off target effects on endogenous gene expression.

The present disclosure provides methods to create improved chemically-induced dimerization (CID) systems. The disclosed CID systems are improved because they use one or more of 1) human derived or humanized proteins with no or low immunogenicity; 2) proteins with no known intracellular function so that on-going cell physiology is minimally impacted; and 3) small molecule inducers that are already FDA approved for human use and have good pharmacological characteristics for the intended application. The present disclosure also provides uses of the created CID systems.

The proteins used within the disclosed CID systems include antibody binding domains. When used in humans, the antibody binding domains can be human derived or humanized. Antibody binding domains have no known intracellular functions, and accordingly, can be used in CID systems without significantly impacting on-going cellular physiology. Moreover, antibody binding domains can bind with tight affinity to targets allowing more precise control of cellular events than that achieved with currently existing CID systems. In particular embodiments, without significantly impacting on-going cellular physiology means that (i) when analyzing the cellular transcriptome (using, e.g., RNA-Seq, also known as whole transcriptome shotgun sequencing (WTSS)), less than 0.1% of genes show a change in expression; (ii) the integrity of the cell membrane is not affected, and/or (iii) calcium influx in response to physiological stimuli is not affected. In particular embodiments, without significantly impacting on-going cellular physiology means that (i) when analyzing the cellular transcriptome (using, e.g., RNA-Seq, also known as whole transcriptome shotgun sequencing (WTSS)), less than 0.1% of genes show a change in expression; (ii) the integrity of the cell membrane is not affected, and (iii) calcium influx in response to physiological stimuli is not affected. In particular embodiments, more precise control can be confirmed in comparison to the regulation of gene expression using the described FKB12 and FRB dimerization system.

Small molecules that induce protein dimerization are selected to have low to no toxicity, are safe for use in humans and other animals and, preferably, have obtained FDA or other regulatory approval for use in other indications.

In particular embodiments, one binding domain is chosen that binds the selected small molecule with high affinity. This first binding domain is referred to as AB1. The second binding domain binds AB1, but only when AB1 is bound to the selected small molecule. This second binding domain, a "metatype" binding domain, is referred to as AB2.

Cells can include AB1 and AB2, for example, by being administered AB1 and AB2 and/or by being genetically modified to express AB1 and AB2. In the absence of the selected small molecule, AB1 and AB2 will not interact, and cellular events will not be significantly impacted. When the selected small molecule is administered, it will bind AB1. AB2 will then bind the AB1/small molecule complex, causing interaction between AB1 and AB2, and any other proteins that have been associated with them. For example, as shown in FIG. 1A, one binding domain (AB1 or AB2) can be associated with a DNA binding domain and the other binding domain can be associated with a transcription activation domain. When the selected small molecule is administered, it will bind AB1, leading to binding of the AB1/small molecule complex by AB2. AB1/small molecule complex binding with AB2 will lead to interaction between the DNA binding domain and the transcription activation domain and transcription will be initiated.

Figure 1B:
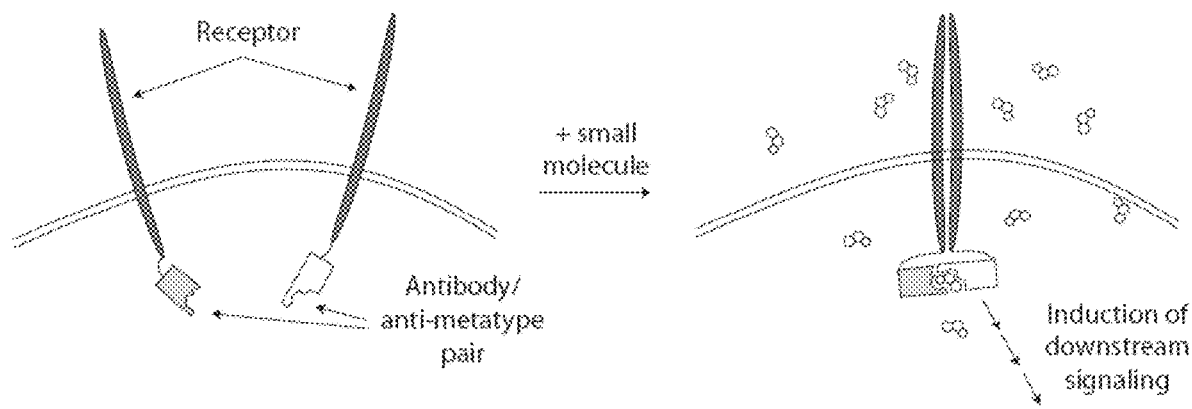

As another non-limiting example, and as shown in FIG. 1B, AB1 and AB2 can each be associated with the intracellular portion of a cellular receptor. In the absence of the selected small molecule, AB1 and AB2 will not interact, and receptor signaling will not be initiated based on the CID system. When the selected small molecule is administered, it will bind AB1 leading to binding of AB2 to the AB1/small molecule complex. Following this binding, the receptor portions will come together, resulting in initiation of receptor signaling.

Figure 1C:
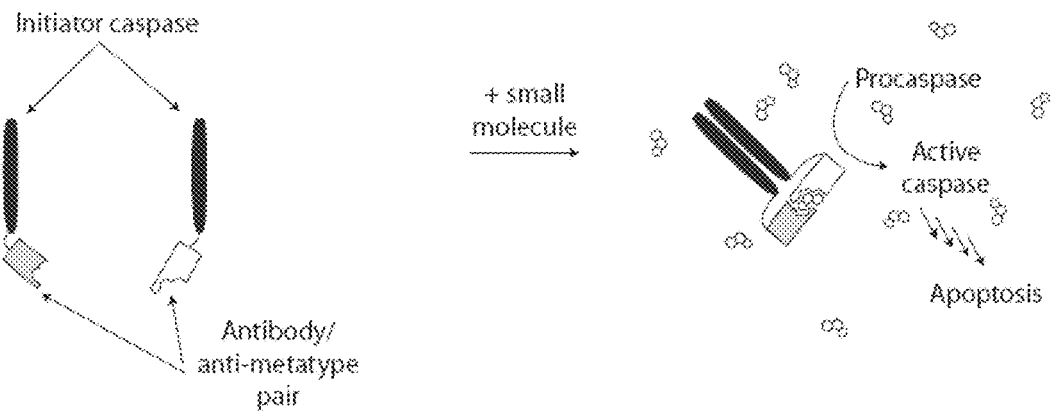
Figure 2A:
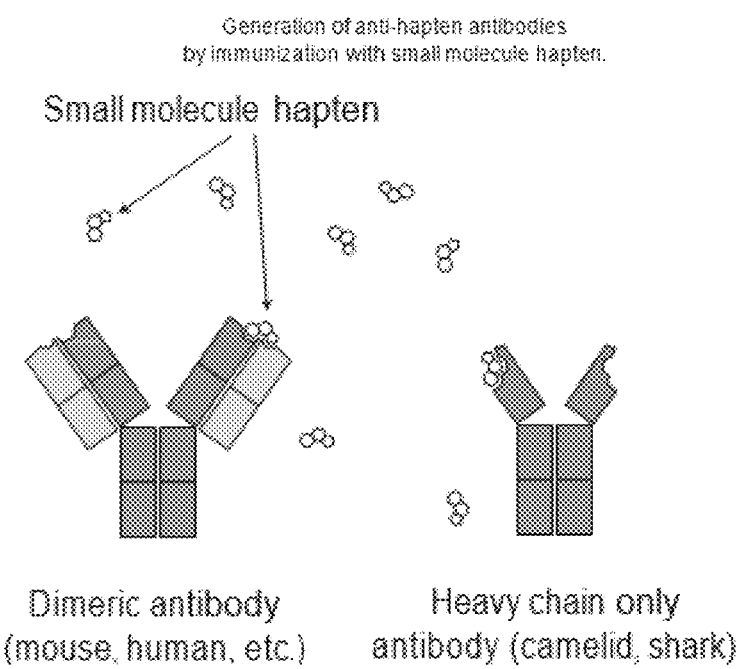
FIGS. 2A-2D. General outline of an exemplary method.
Figure 2B:
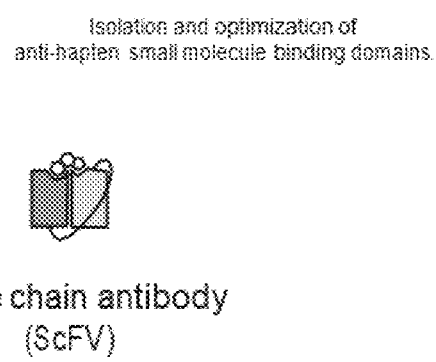
Figure 2C:
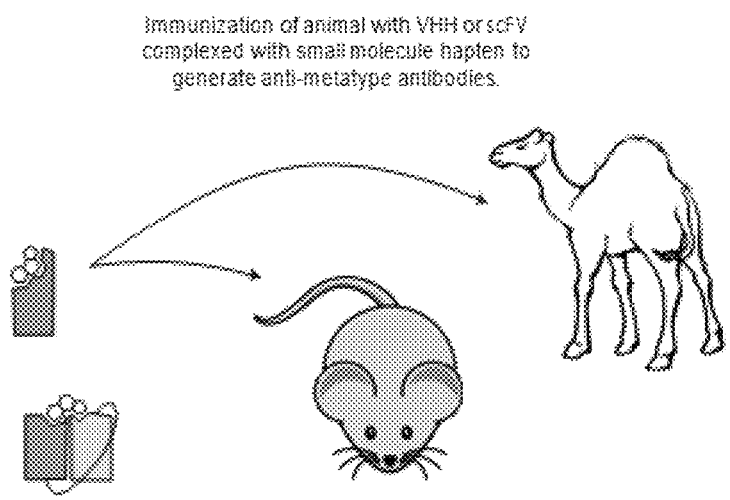
Figure 2D:
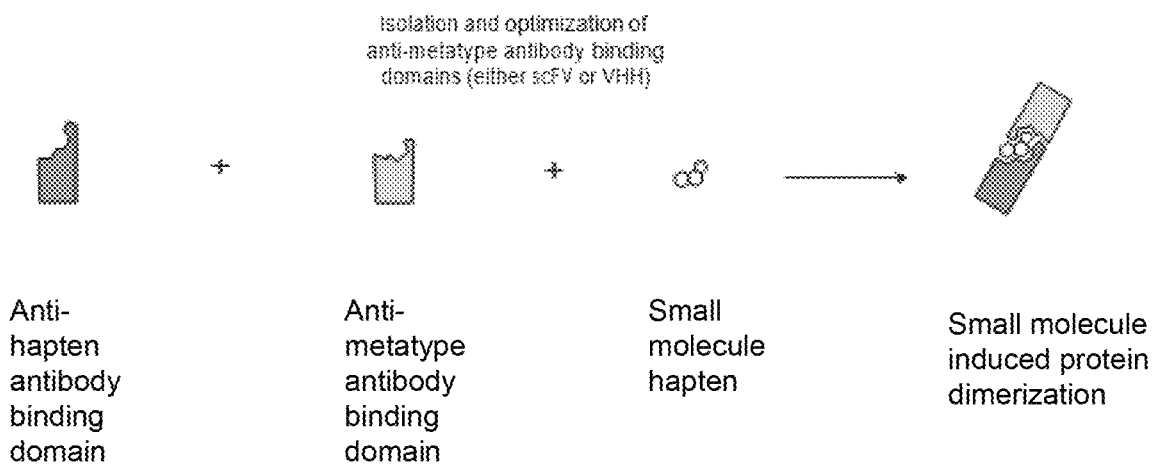

As a third non-limiting example, and as shown in FIG. 1C, AB1 and AB2 can each be associated with an initiator caspase. In the absence of the selected small molecule, AB1 and AB2 will not interact, and cell death processes will not be initiated based on the CID system. When the selected small molecule is administered, it will bind AB1 leading to binding of AB2 to the AB1/small molecule complex. Following this binding, the caspases will come together, resulting in initiation of cell death processes.

Having explained the general mechanisms of the systems, each of the components, uses, and methods to create the systems are now described in more detail.

AB1 and AB2 Binding Domains. At least one of the AB1 and AB2 binding domains include an antibody binding domain. An antibody binding domain refers to any portion of an antibody (e.g., whole antibody or fragment thereof) that retains the ability to bind to an intended epitope (e.g., a portion of the selected small molecule for AB1 and a portion of the AB1/small molecule complex for AB2). In particular embodiments, antibody fragments are utilized as binding domains. Examples of antibody fragments include Fv, scFv, Fab, Fab', Fab'-SH, F(ab')$_2$; diabodies; and linear antibodies.

A Fv fragment includes the VL and VH domains of a single arm of an antibody. Although the two domains of the Fv fragment, VL and VH, are coded by separate genes, they can be joined, using, for example, recombinant methods, by a synthetic linker that enables them to be made as a single protein chain in which the VL and VH regions pair to form monovalent molecules (single chain Fv (scFv)). For additional information regarding Fv and scFv, see e.g., Bird, et al., Science 242 (1988) 423-426; Huston, et al., Proc. Natl. Acad. Sci. USA 85 (1988) 5879-5883; Plueckthun, in The Pharmacology of Monoclonal Antibodies, vol. 113, Rosenburg and Moore (eds.), Springer-Verlag, New York), (1994) 269-315; WO1993/16185; U.S. Pat. Nos. 5,571,894; and 5,587,458.

A Fab fragment is a monovalent antibody fragment including VL, VH, CL and CH1 domains. A F(ab')$_2$ fragment is a bivalent fragment comprising two Fab fragments linked by a disulfide bridge at the hinge region. For discussion of Fab and F(ab')$_2$ fragments having increased in vivo half-life, see U.S. Pat. No. 5,869,046.

Diabodies include two epitope-binding sites that may be bivalent. See, for example, EP 0404097; WO1993/01161; and Holliger, et al., Proc. Natl. Acad. Sci. USA 90 (1993) 6444-6448. Antibody fragments can also include isolated complementary determining regions (CDRs). For a review of antibody fragments, see Hudson, et al., Nat. Med. 9 (2003) 129-134.

Antibody fragments can be made by various techniques, including proteolytic digestion of an intact antibody as well as production by recombinant host cells (e.g. *E. coli*). Antibody fragments can be screened for their binding properties in the same manner as intact antibodies.

As indicated, an epitope denotes the binding site of a target bound by a corresponding binding domain. The binding domain either binds to a linear epitope, (e.g., an epitope consisting of a stretch of 5 to 12 consecutive amino acids), or the binding domain binds to a three-dimensional structure formed by the spatial arrangement of the target. Three-dimensional epitopes recognized by a binding domain, e.g. by the epitope recognition site or paratope of an antibody or antibody fragment, can be thought of as three-dimensional surface features of an epitope molecule. These features fit precisely (in)to the corresponding binding site of the binding domain and thereby binding between the binding domain and its target protein is facilitated.

"Bind" means that the binding domain associates with its target epitope with a dissociation constant (1(D) of $10^{-5}$ M or less, in one embodiment of from $10^{-5}$ M to $10^{-13}$ M, or in one embodiment of from $10^{-5}$ M to $10^{-10}$ M. The term can be further used to indicate that the binding domain does not bind to other biomolecules present, (e.g., it binds to other biomolecules with a dissociation constant (KD) of $10^{-4}$ M or more, in one embodiment of from $10^{-4}$ M to 1 M.

Particular embodiments disclosed herein require high affinity binding between a binding domain and its epitope (e.g., AB1 and a selected small molecule as discussed elsewhere herein). In particular embodiments, high affinity binding requires a dissociation constant (1(D) of $10^{-7}$ M or less, or in one embodiment of from $10^{-7}$ M to $10^{-12}$ M, or in one embodiment of from $10^{-7}$ M to $10^{-15}$ M. In particular embodiments, high affinity binding is demonstrated by clones which maintain small molecule-dye binding for long time periods (e.g., 4 minutes or more after wash out) as described in Example 1.

Binding domains can be obtained using methods of obtaining monoclonal antibodies, methods of phage display, methods to generate human or humanized antibodies, or methods using a transgenic animal or plant engineered to produce antibodies as is known to those of ordinary skill in the art (see, for example, U.S. Pat. Nos. 6,291,161 and 6,291,158) and as described elsewhere herein. Phage display libraries of partially or fully synthetic antibodies are available and can be screened for an antibody or fragment thereof that can bind to a selected small molecule or AB1/small molecule complex. For example, binding domains may be identified by screening a Fab phage library for Fab fragments that specifically bind to a selected small molecule or AB1/small molecule complex (see Hoet et al., Nat. Biotechnol. 23:344, 2005). Phage display libraries of human antibodies are also available. Additionally, traditional strategies for hybridoma development using a selected small molecule or AB1/small molecule complex as an immunogen in convenient systems (e.g., mice, HuMAb mouse®, TC mouse™, KM-mouse®, llamas, chicken, rats, hamsters, rabbits, etc.) can be used to develop binding domains. Once identified, the amino acid sequence or polynucleotide sequence coding for the binding domain can be isolated and/or determined. FIG. 2 particularly depicts exemplary methods to obtain AB1 and AB2 binding domains to produce a CID as disclosed herein.

Supplementing disclosure elsewhere herein, methods for humanizing antibodies are described in, e.g., Jones et al., Nature 321:522-525 (1986); Riechmann et al, Nature 332: 323-327 (1988); Verhoeyen et al., Science 239:1534-1536 (1988), and U.S. Pat. No. 4,816,567. Generally, residues from the variable domain of a non-human antibody are "imported" into a human immunoglobulin molecule, resulting in antibodies in which some hypervariable region residues and possibly some FR residues of a human antibody are substituted by residues from analogous sites of non-human antibodies. In human applications, it is important to humanize a non-human binding domain while retaining high affinity for the selected small molecule or AB1/small molecule complex. To this end, three dimensional immunoglobulin models are available and suitable for use in analyzing proposed humanized sequences in comparison to the parental non-human antibodies. Such analysis permits identification of residues likely involved in recognition and binding of the selected small molecule or AB1/small molecule complex, and therefore rational design of humanized sequences that retain the specificity and affinity for the targeted epitopes.

Numerous small molecules can be selected for use with the CID systems disclosed herein. Preferably, the selected small molecule is approved for use in humans by a regulatory authority, such as the FDA. Administration of the small molecule should not cause adverse effects that outweigh the benefits of the CID within the judgment of a sound medical provider (physician or veterinarian) or research scientist.

Selected small molecules could be, for example, antibiotics. Exemplary antibiotics include aclarubicin, actinomycin D, actinoplanone, adriamycin, aeroplysinin derivative, aminoglycosides (e.g., gentamycin or neomycin), amoxicillin, ampicillin, amrubicin, anthracycline, azinomycin-A, azithromycin, aztreonam, bisucaberin, bleomycin sulfate, bryostatin-1, calichemycin, cefepime, cefixime, ceftriaxone, cephalosporin C, cephamandol, cephazolin, chloramphenicol, chromoximycin, ciprofloxacin, clindamycin, dactinomycin, daunorubicin, ditrisarubicin B, doxorubicin, doxorubicin-fibrinogen, doxycycline, elsamicin-A, epirubicin, erbstatin, erythromycin, esorubicin, esperamicin-Al, esperamicin-Alb, fostriecin, glidobactin, gregatin-A, grincamycin, herbimycin, idarubicin, illudins, imipenem, kazusamycin, kesarirhodins, menogaril, meropenem, metronidazole, mitomycin, neoenactin, netilmycin, oxalysine, oxaunomycin, penicillins (e.g., oxacillin or mezlocillin), peplomycin, pilatin, pirarubicin, porothramycin, pyrindanycin A, rifampicin, spectinomycin, streptomycin, tetracycline, tigecycline, tobramycin, and trimethoprim.

As previously stated, so long as administration of the small molecule does not cause adverse effects that outweigh the benefits of the CID within the judgment of a sound medical provider (physician or veterinarian) or research scientist, additional small molecules could be selected from alkylating agents, anesthetic agents, anti-fungal agents, anti-infective agents, anti-inflammatory agents, anti-metabolite agents, anti-microbials, anti-mitotics, anti-oxidants, anti-platelets, anti-proliferative agents, anti-secretory agents, anti-stenosis agents, anti-thrombins, anti-viral agents, antibodies, antiseptics, cytostatic agents, free radical scavengers, growth factor antagonists, labeling agents (e.g. contrast agents, fluorescent agents, luminescent agents, magnetic agents, radiolabeled agents, radiopaque agents), nucleotides, nutraceutical agents (e.g. vitamins minerals etc.), proteins, radiotherapeutic agents, ribonucleases, steroids, and vasodilators. As is understood by one of ordinary skill in the art, many small molecules can fall into more than one of these classes, and inclusion in one class does not foreclose inclusion in another. That being said, more particular examples of some of these small molecules are provided below.

Exemplary alkylating agents include aldo-phosphamide analogues, altretamine, anaxirone, bestrabucil, budotitane, carboplatin, carmustine, chlorambucil, cisplatin, cyclophosphamide, cyplatate, diphenylspiromustine, diplatinum cytostatic, elmustine, estramustine phosphate sodium, fotemustine, hepsul-fam, ifosfamide, iproplatin, lomustine, mafosfamide, mitolactol, oxaliplatin, prednimustine, ranimustine, semustine, spiromustine, tauromustine, temozolomide, teroxirone, tetraplatin, and trimelamol.

Exemplary anesthetic agents include amethocaine, amobarbital, barbiturates, benzodiazepines, bupivacaine, buprenorphine, butorphanol, cocaine, diacetyl morphine, diazepam, dibucaine, etomidate, fentanyl, hydromorphone, ketamine, levobupivacaine, levorphanol, lidocaine, lorazepam, meperidine, mepivacaine, methadone, methohexital, midazolam, morphine, nalbuphine, oxycodone, oxymorphone, pentazocine, prilocaine, procaine, propofol, remifentanil, ropivacaine, sufentanil, thiamylal, and thiopental.

Exemplary antifungal agents include polyene antifungals, such as amphotericin B, candicidin, filipin, hamycin, imidaxole, natamycin, nystatin, rimocidin, thiazole antifungals, and triazole. Imidazole antifungal agents include bifonazole, blotrimazole, butoconazole, econazole, fenticonazole, isoconazole, ketoconazole, miconazole, omoconazole, oxiconazole, sertaconazole, sulconazole, and tioconazole. Triazole based antifungal agents include albaconazole, fluconazole, isavuconazole, itraconazole, posaconazole, ravuconazole, terconazole, and voriconazole. Thiazole antifungal agents include abafungin. Examples of allylamine antifungal agents include amorolfin, butenafine, naftifine and terbinafine. Echinocandin anti-fungal agents include anidulafungin, caspofungin, and micafungin. Additional antifungal agents include benzoic acid, ciclopirox, crystal violet, flucytosine or 5-fluorocytosine, griseofulvin, haloprogin, polygodial, tolnaftate and undecylenic acid. Essential oils having antifungal properties include allicin, citronella oil, coconut oil, lemon myrtle, lugol's iodine, neem seed oil, olive leaf, orange oil, oregano, palmarosa oil, patchouli, selenium, and tea tree oil.

Exemplary anti-infective agents include pyrimidine analogs. A pyrimidine analog generally refers to a compound with a pyrimidine ring structure (1,3-diazine) substituted with one or more atoms or chemical groups or oxidized at one or more carbons in the pyrimidine ring structure. In particular embodiments, the pyrimidine analog contains a halogen substituent, such as F, Cl, Br, or I, at a carbon in the pyrimidine ring structure. Exemplary fluoropyrimidines include 5-fluorocytosine, 5-fluorothymidine, 5-FU, 5-FUdR (5-fluoro-deoxyuridine; floxuridine), capecitabine, fluorodeoxyuridine monophosphate (5-dFUMP), fluorouridine triphosphate (5-FUTP), trifluorothymidine, and trifluridine. Other halogenated pyrimidine analogs include 5-bromocytosine, 5-bromodeoxyuridine (5-BudR), 5-bromouracil, 5-chlorocytosine, 5-chlorodeoxyuridine, 5-chlorouracil, 5-iodocytosine, 5-iododeoxyuridine (5-IudR), and 5-iodouracil.

Uracil pyrimidine analogs refer to compounds that contain a uracil ring structure substituted with one or more atoms or chemical groups. The uracil analog contains a halogen substituent, such as F, Cl, Br, or I. In certain embodiments, the uracil analog contains an F substituent, and is referred to as a fluorouracil analog. Exemplary fluorouracil analogs include 5-FU, carmofur, doxifluridine, emitefur, floxuridine, and tegafur.

Other exemplary anti-infectives include chlorhexidine, silver compounds, silver ions, silver particles, or other metallic compounds, ions or particles (such as gold). Additional anti-infective agents include 2-p-sulfanilyanilinoethanol, 4-sulfanilamidosalicylic acid, 4,4'-sulfinyldianiline, acetosulfone, amifloxacin, amikacin, amoxicillin, amphotericin B, apalcillin, apicycline, apramycin, arbekacin, aspoxicillin, azaserine, azidamfenicol, azithromycin, aztreonam, bacitracin, bambermycin(s), biapenem, brodimoprim, butirosin, candicidin(s), capreomycin, carbenicillin, carbomycin, carumonam, cefadroxil, cefamandole, cefatrizine, cefbuperazone, cefclidine, cefdinir, cefditoren, cefepime, cefetamet, cefinenoxime, cefixime, cefminox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, chloramphenicol, chlorhexidine, chlorphenesin, chlortetracycline, ciprofloxacin, ciprofloxacin, clarithromycin, clinafloxacin, clindamycin, clomocycline, colistin, cyclacillin, dapsone, demeclocycline, dermostatin(s), diathymosulfone, dibekacin, dihydrostreptomycin, dirithromycin, enoxacin, enviomycin, epicillin, erythromycin, filipin, fleroxacin, flomoxef, fortimicin(s), fungichromin, gentamicin(s), glucosulfone solasulfone, gold compounds (such as gold chloride, auranofin), gold ions, gold particles, gramicidin S, gramicidin(s), grepafloxacin, guamecycline, hetacillin, imipenem, iodine, isepamicin, josamycin, kanamycin(s), leucomycin(s), lincomycin, lomefloxacin, lucensomycin, lymecycline, meclocycline, mepartricin, meropenem, methacycline, micronomicin, midecamycin(s), minocycline, moxalactam, mupirocin, nadifloxacin, natamycin, neomycin, netilmicin, norfloxacin, nystatin, ofloxacin, oleandomycin, oligomycin(s), oxytetracycline, panipenem, paromomycin, pazufloxacin, pefloxacin, penicillin N, perimycin A, pipacycline, pipemidic acid, polymyxin, povidone/iodine, primycin, p-sulfanilylbenzylamine, quinacillin, ribostamycin, rifamide, rifampin, rifamycin SV, rifapentine, rifaximin, ristocetin, ritipenem, rokitamycin, rolitetracycline, rosaramycin, rosoxacin, roxithromycin, salazosulfadimidine, sancycline, silver chloride, silver compounds (e.g. silver ions, silver nitrate, silver oxide), silver particles, sisomicin, sparfloxacin, spectinomycin, spiramycin, streptomycin, succisulfone, sulfachrysoidine, sulfaloxic acid, sulfamidochrysoidine, sulfanilic acid, sulfoxone, teicoplanin, temafloxacin, temocillin, tetracycline, tetroxoprim, thiamphenicol, thiazolsulfone, thiostrepton, ticarcillin, tigemonam, tobramycin, tosufloxacin, trimethoprim, trospectomycin, trovafloxacin, tuberactinomycin, tubercidin, and vancomycin.

Exemplary anti-metabolite agents include 5-fluorouracil, 5-FU-fibrinogen, acanthifolic acid, aminothiadiazole, brequinar sodium, carmofur, cyclopentyl cytosine, cytarabine conjugates, cytarabine phosphate stearate, dezaguanine, dideoxycytidine, dideoxyguanosine, didox, doxifluridine, fazarabine, floxuridine, fludarabine phosphate, inhibitors of essential amino acids, isopropyl pyrrolizine, methobenzaprim, methotrexate, N-(2'-furanidyl)-5-fluorouracil, norspermidine, ornithine decarboxylantion inhibitors, pentostatin, piritrexim, plicamycin, thioguanine, tiazofurin, trimetrexate, tyrosine kinase inhibitors, and uricytin.

Exemplary anti-microbials include antimicrobial peptides (AMPs), chlorhexidine diacetate, and silver carbonate.

Exemplary anti-platelets include, abciximab, adenosine diphosphate (ADP) receptor inhibitors, adenosine reuptake inhibitors, aspirin, cilostazol, clopidogrel, dipyridamole, elinogrel, eptifibatide, glycoprotein IIB/IIIA inhibitors (intravenous use only), GPVI antagonists, irreversible cyclooxygenase inhibitors, PAR-1 or PAR-4 antagonists, phosphodiesterase inhibitors, prasugrel, terutroban thromboxane inhibitors, thromboxane receptor antagonists, thromboxane synthase inhibitors, ticagrelor, ticlopidine, and tirofiban.

Exemplary anti-proliferative agents include acetylsalicylic acid, acitretin, alstonine, amonafide, amphethinile, amsacrine, angiopeptin, ankinomycin, anti-neoplaston, aphidicolin glycinate, asparaginase, baccharin, batracylin, benfluoron, benzotript, bromofosfamide, caracemide, carmethizole hydrochloride, chlorsulfaquinoxalone, clanfenur, claviridenone, crisnatol, curaderm, cytarabine, cytocytin, dacarbazine, datelliptinium, dihaematoporphirin ether, dihydrolenperone, dinaline, distamycin, docetaxel, elliprabin, elliptinium acetate, enoxaprin, epothilones, ergotamine, etoposide, etretinate, fenretinide, gallium nitrate, genkwadaphnin, HDAC inhibitors, hexadecylphosphocholine, hirudin, homoharringtonine, hydroxyurea, ilmofosine, isoglutamine, isotretinoin, leukoregulin, lonidamine, merbarone, merocyanlne derivatives, methylanilinoacridine, minactivin, mitonafide, mitoquidone, mitoxantrone, mopidamol, motretinide, N-(retinoyl)amino acids, N-acylated-dehydroalanines, nafazatrom, nocodazole derivative, octreotide, oquizanocine, paclitaxel, pancratistatin, pazelliptine, piroxantrone, polyhaematoporphyrin, polypreic acid, probimane, procarbazine, proglumide, razoxane, retelliptine, spatol, spirocyclopropane derivatives, spirogermanium, strypoldinone, superoxide dismutase, teniposide, thaliblastine, tocotrienol, topoisomerase inhibitors and agents, topotecan, tubulin interacting agents, ukrain, vinblastine sulfate, vincristine, vindesine, vinestramide, vinorelbine, vintriptol, vinzolidine, withanolides, and monoclonal antibodies capable of blocking smooth muscle cell proliferation.

Exemplary anti-septics include alcohols (e.g., ethanol, 1-propanol, 2-propanol), quaternary ammonium salts also known as quats or QAC's (e.g., benzalkonium chloride (BAC), cetyl trimethylammonium bromide (CTMB), cetylpyridinium chloride (Cetrim, CPC) and benzethonium chloride (BZT)), boric acid, brilliant green, calcium hypochlorite, chlorhexidine gluconate, hydrogen peroxide, iodine (e.g., providone-iodine and Lugol's iodine), Mercurochrome, octenidine dihydrochloride, phenol (carbolic acid) compounds, polyhexanide (polyhexamethylene biguanide, PHMB), sodium bicarbonate, sodium chloride, and sodium hyposhlorite.

Exemplary anti-thrombins include aspirin, cilostazol, dabigatran, enoxaparin, eptifibatide, heparin, hirudin, and urokinase.

Exemplary anti-viral agents include 5-bromouridine, acyclovir, alovudine, amantadine, antiviral proteins, arbidol, brivudine, cidofovir, daclatasvir, docosanol, double-stranded RNA (dsRNA) activated caspase oligomerizer (DRACO), famciclovir, FGI-104, fialuridine, fomivirsen, foscarnet, FV-100, ganciclovir, ibacitabine, idoxuridine, imiquimod, inosine, inosine pranobex, interferon, maribavir, methisazone, moroxydine, nucleotide antivirals, oragen, penciclovir, pleconaril, podophyllotoxin, prosetta, PSI-6130, reciGen, resiquimod, ribavirin, rintatolimod, semapimod, setrobuvir, simeprevir, sofosbuvir, sorivudine, taribavirin, tecovirimat, telbivudine, tenofovir alafenamide fumarate, theaflavin, tilorone, trifluridine, tromantadine, valaciclovir, valganciclovir, and vidarabine.

Exemplary vasodilators include hydralazine and minoxidil.

Once proteins (e.g., antibody binding domain fragments) and the small molecule are identified, selected and/or generated, the proteins can be expressed as fusion proteins with effector molecules. As indicated earlier, effector molecules are those that regulate a process in a cell when dimerized. Thus, effector molecules can be DNA binding domains, transcription activation domains, portions of receptors (e.g., intracellular receptors), caspases, enzymes, kinases, etc.

Exemplary DNA-binding domain proteins and transcription activation domain proteins include zinc fingers, helix-loop-helixes, helix-turn-helixes, leucine zippers, catabolite activator protein (CAP), activator protein-1 (AP-1), CCAAT/Enhancer Binding Protein (C/EBP), heat shock proteins, activating transcription factor (ATF), cAMP response element-binding protein (CREB), cMyc, and N-Myc.

The zinc fingers stabilize DNA binding by holding its phosphate backbone. The basic helix-loop-helix contains two a-helices connected by a loop. The helix-turn-helix motif is a common DNA recognition motif in prokaryotes. In some transcription factors, the dimer binding site with DNA forms the leucine zipper. The leucine zipper can mediate both homo- or heterodimer formation.

The catabolite activator protein (CAP) activates transcription at more than one hundred promoters. CAP is a dimer with two identical subunits and contains a helix-turn-helix DNA binding motif. CAP interacts with a 22 bp two-fold symmetric DNA site. The CAP-DNA complex is two-fold symmetric in that one subunit of CAP interacts with one half of the DNA site, while the other subunit of CAP interacts with the other half of the DNA site.

AP-1, C/EBP, and ATF/CREB are leucine zipper proteins that bind the DNA recognition sequence as a dimer. Heat shock proteins are also leucine zipper proteins, but bind as a trimer. cMyc and N-Myc are basic helix-loop-helix proteins that bind as a dimer.

As will be understood by one of ordinary skill in the art, transcription repressor proteins can also be used as effector proteins with the CID systems disclosed herein. Transcription repressor proteins inhibit, rather than initiate transcription. Examples of transcription repressor proteins include the methionine repressor (metJ) and the lacZYA repressor.

Exemplary intracellular receptors include nuclear receptors and cytoplasmic receptors. These types of receptors are soluble proteins. The ligand for these receptors (e.g., non-polar hormones, vitamin A, retinoic acid, vitamin D, and derivatives and metabolites) can pass through the plasma membrane by passive diffusion to initiate signal transduction. Upon binding, the complex can pass through the nuclear membrane into the nucleus, altering gene expression. For example, activated nuclear receptors attach to the DNA at hormone-specific hormone-responsive element (HRE) sequences, located in the promoter region of genes activated by the hormone-receptor complex. Nuclear receptors can also have DNA-binding domains containing zinc fingers and a ligand-binding domain.

Steroid hormone receptors particularly are located in the cytoplasm (Type I) or nucleus (Type II) and belong to a large family of transcription factors. Type I receptors have a heat shock protein (HSP) associated with the inactive receptor that will be released when the receptor interacts with the ligand. Type II nuclear receptors have no HSP, and in contrast to the classical type I receptor are located in the cell nucleus.

Steroid receptors have a single polypeptide chain comprising three distinct domains: an amino terminus which is involved in activating or stimulating transcription by interacting with other components of the transcriptional machinery; a DNA binding domain which is responsible for binding the receptor to the specific sequences of DNA; and a carboxy-terminus or ligand-binding domain which binds the natural ligand. Additionally, there are two other regions in these receptors: the nuclear localization sequence which targets the protein to the nucleus; and the dimerization domain, which latches the two receptors together in a form capable of binding the DNA.

The retinoic acid receptor (RAR) is another example of a Type II nuclear receptor that can also act as a transcription factor. There are three retinoic acid receptors (RAR), RAR-alpha, RAR-beta, and RAR-gamma, encoded by the RARA, RARB, RARG genes, respectively.

Caspases are a family of cysteine aspartic proteases or cysteine-dependent aspartate-directed proteases that play an important role in apoptosis, necrosis, and inflammation. Caspases are essential in cellular processes including apoptosis, in development and in stages of adult life. Some caspases are also required in the immune system for the maturation of lymphocytes. Failure of apoptosis has been shown to contribute to tumor development, chemo-resistance and autoimmune diseases.

Caspases are grouped as either initiators or effectors of apoptosis, depending on where they enter the cell death process. The initiator caspases cleave inactive pro-forms of effector caspases, thereby activating them. The effector caspases subsequently cleave other protein substrates within the cell to trigger the apoptotic process. The initiation of this caspase cascade is regulated by caspase inhibitors.

Prior to activation, initiator caspases are present as monomers that must dimerize for full activation whereas effector caspases are present as dimeric zymogens that must be processed for full activation. The stability of the dimer may be due predominately to the interactions in the dimer interface as each caspase has unique properties in this region that lend to its specific mode of activation. Moreover, dimerization is responsible for active site formation because both monomers contribute residues that enable the formation of a fully functional active site. Overall, dimerization plays a key role in the ability of caspases to form fully functional proteases.

Examples of initiator caspases include Caspase-2 (CASP2), Caspase-8 (CASP8), Caspase-9 (CASP9), and Caspase-10 (CASP10). Examples of effector caspases include Caspase-3 (CASP3), Caspase-6 (CASP6), and Caspase-7 (CASP7). Other caspases that are not classified as an initiator or effector caspases include Caspase-4 (CASP4), Caspase-5 (CASP5), and Caspase-1 (CASP1). CASP4 and CASP5 are inflammatory enzymes and together with CASP1 are involved in T-cell maturation. Other names for these exemplary caspases include the following: "ICE" for CASP1; "ICH-1" for CASP2; "CPP32," "Yama," and "apopain" for CASP3; "ICE(rel)II," "TX," and "ICH-2" for CASP4; "ICE(rel)III," and "TY" for CASP5; "Mch2" for CASP6; "Mch3," "ICE-LAP3," and "CMH-1" for CASP7; "FLICE," "MACH," and "Mch5" for CASP8; "ICE-LAP6," and "Mch6" for CASP9; and "Mch4," and "FLICE-2" for CASP10.

As will be understood by one of ordinary skill in the art, effector proteins can also include, for example, other various enzymes, kinases and proteases.

As described in more detail elsewhere herein, effector proteins can be expressed as fusions with the CID proteins of systems disclosed herein. Expression of fusion proteins is well known, and fusion proteins can include any appropriate linkers or spacers to facilitate appropriate interaction among various domains. Effector proteins and CID proteins can also be linked through any other mechanism known or available to those of ordinary skill in the art.

Particular embodiments include methods of creating the CID systems described herein. In particular embodiments, the methods include selecting, identifying and/or generating a metatype antibody binding domain that binds the first protein only when the first protein is bound to the selected small molecule.

Particular embodiments include selecting, identifying and/or generating a first antibody binding domain that binds the selected small molecule and selecting, identifying and/or generating a metatype antibody binding domain that binds the first antibody binding domain only when the first binding domain is bound to the selected small molecule.

Particular embodiments include selecting, identifying and/or generating a small molecule.

Particular embodiments include selecting, identifying and/or generating a small molecule, selecting, identifying and/or generating a first antibody binding domain that binds the selected small molecule, and selecting, identifying and/or generating a metatype antibody binding domain that binds the first antibody binding domain only when the first binding domain is bound to the selected small molecule.

Particular embodiments of the methods include one or more of the following steps: selecting, identifying and/or generating a small molecule; selecting, identifying and/or generating a binding domain that binds the small molecule with high affinity (AB1); and selecting, identifying and/or generating a binding domain that binds the AB1/small molecule complex (AB2) but not AB1 alone.

Particular embodiments of the methods include one or more of the following steps: selecting a small molecule; attaching the selected small molecule to a protein carrier to form an immunogen or to a solid substrate; selecting, identifying and/or generating a binding domain that binds the small molecule with high affinity (AB1); and selecting, identifying and/or generating a binding domain that binds the AB1/small molecule complex (AB2) but not AB1 alone.

Particular embodiments of the methods include one or more of the following steps: selecting a small molecule; attaching the small molecule to a solid support; selecting, identifying and/or generating a binding domain (AB1) that binds the selected small molecule (rather than the solid substrate) with high affinity; humanizing the AB1 binding domains, if necessary; confirming continued high affinity binding between the AB1 binding domains and the selected small molecule; binding AB1 to the selected small molecule; selecting, identifying and/or generating a binding domain (AB2) that binds the AB1/small molecule complex in manner that is dependent on the presence of the small molecule; optimizing the AB1/small molecule/AB2 binding complex; and using the formed CID system to regulate cellular events.

Particular embodiments of the methods include one or more of the following steps: selecting a small molecule; attaching the small molecule to a carrier protein to produce an immunogen; immunizing an animal against the immunogen; collecting and isolating white blood cells/B cells and reverse transcribing RNA into cDNA; amplifying cDNA of immunogen binding domains; digesting resulting PCR products and ligating the products into a screening vector; transfecting screening vectors into cells of growth colonies (e.g., electrocompetent E. coli); expanding and selecting transfected cells; extracting plasmids from expanded and selected transfected cells; integrating plasmids into a host cell genome and selecting expressing cells; selecting cells expressing binding domains (AB1) that bind the selected small molecule (rather than the attached carrier protein) with high affinity; recovering sequences encoding AB1 binding domains expressed by selected cells and amplifying the sequences; humanizing the AB1 binding domains, if necessary; confirming continued high affinity binding between the AB1 binding domains and the selected small molecule; expressing humanized AB1 binding domains in host cells; isolating and purifying the expressed human or humanized AB1 binding domains; confirming binding affinity of the isolated and purified AB1 binding domains and the selected small molecule; immunizing an animal with the AB1/small molecule complex to form anti-metatype antibodies against the complex; collecting and isolating white blood cells/B cells and reverse transcribing RNA into cDNA; amplifying cDNA of AB1/small molecule complex binding domains; digesting resulting PCR products and ligating the products into a screening vector; selecting binding domains (AB2) that bind the AB1/small molecule complex in manner that is dependent on the presence of the small molecule; recovering sequences encoding AB2 binding domains; humanizing the AB2 binding domains, if necessary; optimizing the AB1/small molecule/AB2 binding complex; and using the formed CID system to regulate cellular events.

Methods disclosed herein include treating subjects (humans, veterinary animals (dogs, cats, reptiles, birds, etc.), livestock (horses, cattle, goats, pigs, chickens, etc.), and research animals (monkeys, rats, mice, fish, etc.) with AB1, AB2 and a small molecule of a CID. Treating subjects includes delivering therapeutically effective amounts. Therapeutically effective amounts include those that provide effective amounts and/or therapeutic treatments.

An "effective amount" is the amount of the AB1, AB2 and small molecule necessary to result in a desired physiological change in a subject. Effective amounts are often administered for research purposes. Effective amounts disclosed herein regulate a cellular event. That is, e.g., they affect gene expression, intracellular receptor signaling and/or cell death in an intended manner.

A "therapeutic treatment" includes a treatment administered to a subject who would benefit from regulation of a cellular event. Any condition that can be improved by such cellular regulation can be treated using a CID developed according to the methods disclosed herein. Exemplary conditions include cancer, graft vs. host disease, Alzheimer's disease, Parkinson's disease, AIDs, sensory disturbances or deficits, paralysis, numbness, demyelinating diseases, metabolic diseases, autoimmune diseases, neurological diseases, heart conditions, diabetes, organ or tissue rejection, burns, skin disorders, bone disorders, etc.

The effectiveness of a therapeutically effective amount can be confirmed by observing the cellular regulation (e.g., an increase in protein expression or cell death) through known assays or by observing a clinical improvement in a treated condition.

The actual dose of AB1, AB2 and small molecule amount administered to a particular subject can be determined by a physician, veterinarian, or researcher taking into account parameters such as physical and physiological factors including target; body weight; severity of condition; type of cell requiring regulation; previous or concurrent therapeutic interventions; idiopathy of the subject; and route of administration.

Exemplary doses of AB1, AB2 and small molecule can often range from 0.1 to 5 µg/kg or from 0.5 to 1 µg/kg. In other examples, a dose can include 1 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 1000 µg/kg, 0.1 to 5 mg/kg, or from 0.5 to 1 mg/kg. In other examples, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, or more.

As is understood by one of ordinary skill in the art, when AB1 and AB2 will be expressed intracellularly by the subject, these exemplary dose amounts refer to administered compositions including nucleic acid molecules as a genetic therapy that will effectively deliver encoding nucleotide sequences intracellularly. Accordingly, as the context indicates, AB1 and AB2 can refer to a protein or a nucleic acid encoding the protein.

Any method of delivering a therapeutically effective amount of nucleic acids (e.g., RNA, DNA) encoding AB1, AB2 and/or AB1-effector or AB2-effector fusion proteins may be used. The most common ways involve the use of naked DNA, DNA complexes, vectors, viral vectors (e.g., recombinant viruses), plasmids, and transposons/transposases.

In particular embodiments, when administered as naked DNA or DNA complexes, the nucleic acids can incorporate chemical groups that alter the physical characteristics of the nucleic acid. As an example, the internucleotide phosphate ester can be optionally substituted with sulfur so as to retard the degradation of the nucleic acid molecule. The nucleic acid molecule can be introduced into the target cell by any means known to those of ordinary skill in the art, including several examples described below.

Any vector suitable for administering nucleic acid molecules encoding fusion proteins to a cell or to a subject, such that the cell or cells in the subject express the fusion proteins may be employed in methods using CID systems created according to the methods disclosed herein. In particular embodiments, the nucleic acid molecule is incorporated into a viral particle to mediate gene transfer to a cell. In particular embodiments, the virus simply can be exposed to the appropriate host cell under physiologic conditions, permitting uptake of the virus. Examples of viral vectors include those derived from adenovirus, adeno-associated virus, retrovirus, lentivirus, herpes simplex virus, vaccinia virus, etc.

In particular embodiments, the nucleic acids or the vectors comprising the nucleic acids can be transfected into cells by ex vivo transformation; injection, such as subcutaneous, intradermal, intramuscular, intravenous, intraperitoneal injection; liposome mediated transfection; receptor mediated transfection; etc.

Vectors can comprise regulatory sequences to control the expression of the nucleic acid molecules. These regulatory sequences can be eukaryotic or prokaryotic in nature. In particular embodiments, the regulatory sequence can be a tissue specific promoter such that the expression of the fusion proteins will be substantially greater in the target tissue type compared to other types of tissue. In particular embodiments, the regulatory sequence can result in the constitutive expression of the fusion proteins upon entry of the vector into the cell. Alternatively, the regulatory sequences can include inducible sequences. Inducible regulatory sequences are well known to those skilled in the art and are those sequences that require the presence of an additional inducing factor to result in expression of the fusion proteins. Examples of suitable regulatory sequences include binding sites corresponding to tissue-specific transcription factors based on endogenous nuclear proteins, sequences that direct expression in a specific cell type, the lac operator, the tetracycline operator and the steroid hormone operator. Any inducible regulatory sequence known to those of skill in the art may be used in conjunction with uses of CID systems disclosed herein.

In particular embodiments, the nucleic acid is stably integrated into the genome of a subset of the subject's cells. In particular embodiments, the nucleic acid is stably maintained in a subset of the subject's cells as a separate, episomal segment.

In particular embodiments, the efficiency of integration, the size of the DNA sequence that can be integrated, and the number of copies of a DNA sequence that can be integrated into a genome can be improved by using transposons. Transposons or transposable elements include a short nucleic acid sequence with terminal repeat sequences upstream and downstream. Active transposons can encode enzymes that facilitate the excision and insertion of nucleic acid into a target DNA sequence.

A number of transposable elements have been described in the art that facilitate insertion of nucleic acids into the genome of vertebrates, including humans. Examples include sleeping beauty (e.g., derived from the genome of salmonid fish); piggyback (e.g., derived from lepidopteran cells and/or the *Myotis lucifugus*); mariner (e.g., derived from *Drosophila*); frog prince (e.g., derived from *Rana pipiens*); Tol2 (e.g., derived from medaka fish); TcBuster (e.g., derived from the red flour beetle *Tribolium castaneum*) and spinON.

Each of the described doses of active ingredients (AB1, AB2 and small molecule) can be each component alone, AB1 and AB2 in combination, or AB1, AB2 and the small molecule in combination. In particular embodiments, when included in combinations to produce a dose, such as a dose stated herein, the substituents in the combination can be provided in exemplary ratios such as: 1:1:1; 1:2:1; 1:3:1; 1:4:1; 1:5:1; 1:10:1; 1:2:2; 1:2:3; 1:3:4; 1:4:2; 1:5:3; 1:10: 20; 1:1:2; 1:4:3; 1:100:1; 1:25:30; 1:4:16; 1:1000:15; 1:3: 10; 1:5:15; 1:50:90; 1:18:3; 1:10:100 (wherein AB1, AB2 and the small molecule, in particular individual embodiments, can occur at each ratio position of each provided ratio to provide a significant number of beneficial ratios). The substituents in a combination can be provided within the same composition or within different compositions.

Therapeutically effective amounts can be achieved by administering single or multiple doses of AB1, AB2 of the small molecule during the course of a treatment regimen (e.g., QID, TID, BID, daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months, or yearly).

"Controllably administering" a selected small molecule means that the presence of the small molecule within the cells of a subject occurs following establishment of a therapeutically effective amount of AB1 and AB2 and that the selected small molecule generally will be metabolized by the cell while therapeutically effective amounts of AB1 and AB2 remain. Of course, when cell death is initiated, the cell may cease to exist before the small molecule is fully metabolized.

The Exemplary Embodiments and Example provided below describe exemplary and detailed steps to create a CID as disclosed herein. The disclosure encompasses various combinations of these steps.

EXEMPLARY EMBODIMENTS

1. A method of creating a chemically-induced dimerizing protein system comprising: selecting a metatype antibody binding domain (AB2) that binds a portion of a first binding domain (AB1), but only when AB1 is bound to a small molecule to form an AB1/small molecule complex.
2. A method of embodiment 1 wherein the AB1 is an antibody binding domain.
3. A method of embodiment 1 or 2 wherein AB1 and/or AB2 are fragments of antibody binding domains.
4. A method of embodiment 3 wherein the fragments of antibody binding domains are heavy chain only (VHH) fragments or a single chain antibody fragment (scFV).
5. A method of embodiment 4 wherein the scFV consists essentially of a variable heavy chain and a variable light chain.
6. A method of any of embodiments 1-5 further comprising selecting AB1.
7. A method of any of embodiments 1-6 further comprising selecting the small molecule.
8. A method of any of embodiments 1-5 wherein the selecting is based on confirming AB2 binding to the AB1/small molecule complex and/or AB1 binding to the small molecule.
9. A method of any of embodiments 1-8 wherein AB1 and the small molecule bind with high affinity to form the AB1/small molecule complex.
10. A method of any of embodiments 1-10 further comprising generating AB2 and/or AB1.
11. A method of embodiment 10 wherein the generating comprises immunizing an animal.
12. A method of embodiment 11 wherein the generating comprises identifying AB2 and/or AB1 antibody binding domains formed by the animal in response to the immunization.

13. A method of any of embodiments 1-12 further comprising humanizing AB2 and/or AB1.
14. A method of embodiment 13 wherein the humanizing reduces immunogenicity of AB2 and/or AB1 in a human subject.
15. A method of any of embodiments 1-14 further comprising optimizing AB2 and/or AB1.
16. A method of embodiment 15 wherein the optimizing increases binding affinity between AB1 and the small molecule and/or increases binding affinity between AB2 and the AB1/small molecule complex.
17. A method of embodiments 15 or 16 wherein the optimizing increases the in vivo half-life of AB2 and/or AB1.
18. A method of embodiments 13 or 15 further comprising confirming that binding affinity between AB2 and the AB1/small molecule complex and AB1 and the small molecule has not been reduced by the humanizing or optimizing.
19. A method of any of embodiments 1-18 further comprising attaching the small molecule to a protein or solid substrate.
20. A method of any of embodiment 19 further comprising confirming that AB1 does not bind the protein or solid substrate.
21. A method of any of any of embodiments 10-20 wherein the generating comprises isolating B cells from the animal.
22. A method of any of embodiments 10-21 comprising reverse transcribing RNA from B cells isolated from the animal into cDNA.
23. A method of any of embodiments 10-22 comprising amplifying cDNA reverse transcribed from RNA from B cells isolated from the animal.
24. A method of any of embodiments 10-23 comprising ligating cDNA encoding AB1 or AB2 into a screening vector.
25. A method of embodiment 24 comprising transfecting the screening vector into cells of a growth colony.
26. A method of embodiment 25 wherein the cells of the growth colony are electrocompetent *E. coli*.
27. A method of embodiment 9 wherein the identifying AB1 antibody binding domains formed by the animal in response to the immunization includes screening the transfected cells of embodiment 18 for binding domains that specifically bind the small molecule with high affinity.
28. A method of regulating cellular events comprising administering therapeutically effective amounts of AB1 and AB2 of a chemically-induced dimerizing protein system created according to any of embodiments 1-20 to a subject and controllably administering a therapeutically effective amount of the small molecule of the system to the subject thereby regulating cellular events.
29. A method of embodiment 28 wherein AB1 and AB2 are expressed as fusion proteins with an effector.
30. A method of embodiment 29 wherein the effector is a DNA binding domain protein, a transcription activation domain protein, a transcription repressor domain protein, an intracellular portion of a receptor, an intracellular receptor, a caspase, a kinase, an enzyme or a protease.
31. A method of any of embodiments 28-30 wherein the regulated cellular event is gene expression, intracellular receptor signaling and/or cell death.

Figure 3:
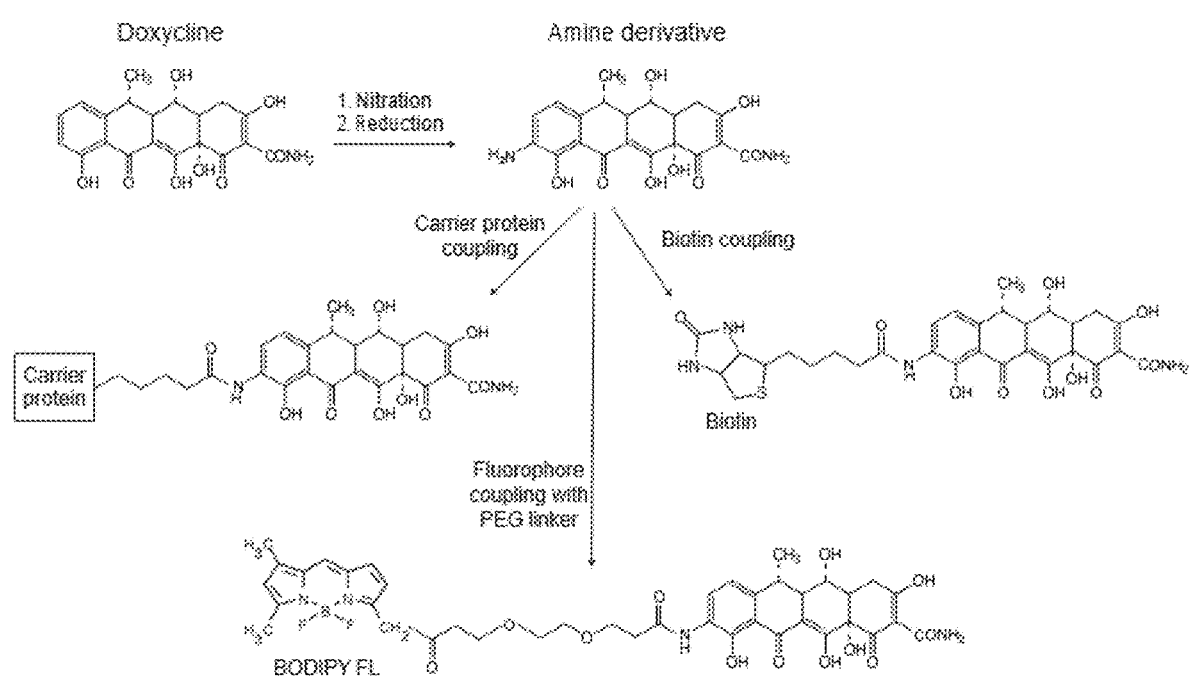
FIG. 3. Example of chemical modification of a small molecule to allow conjugation. The model small molecule doxycycline can be modified by nitration and subsequent reduction, resulting in attachment of a primary amine at the $9^{th}$ carbon. This primary amine can then be used to couple doxycycline to fluorophores, carrier protein, biotin, etc. using known chemistry.

Example 1. Step 1. Small molecule haptens with reactive functional groups (e.g. primary amines, carboxylic acids, aldehydes, sulfhydryls) can be chemically conjugated to protein carriers or solid support by known procedures [44, 45]. Small molecule haptens which do not possess reactive functional groups for conjugation, or where alternate conjugation sites are desired, can be modified to include such reactive groups by known chemical synthesis methods such as the diazonium procedure or the Mannich reaction [44, 45]. For example Pastor-Navarro et al. [46] details methods to chemically modify the prototypical small molecule doxycycline (a small molecule antibacterial drug) for subsequent coupling to a carrier protein. Similarly, Mata [47] describes methods to modify small molecule β-lactams (such as penicillin) for coupling to a solid support. As shown in FIG. 3, doxycycline modified by nitration followed by reduction to contain a primary amine reactive group can be coupled to a carrier protein by reaction with NHS ester, imidoester, or a number of different chemical groups [44]. The carrier protein used maybe any number of proteins used for immunization against haptens, including, for example, keyhole limpet hemocyanin (KLH), bovine serum albumin (BSA), blue carrier protein (BIP), etc. These proteins are commercially available (Thermo Fischer, Sigma Aldrich, etc.) in a number of formats which allow direct chemical conjugation using a variety of chemistries. The particular carrier protein used for coupling, the ratio of hapten to carrier, and other attributes such as length and type of spacer arm can be adjusted to optimize high affinity antibody production.

In particular embodiments, a single reactive functional group of the small molecule is used for coupling to the carrier protein or solid support (FIG. 3). This ensures that each molecule of the hapten is conjugated to the carrier protein or solid support in a single stereotypical orientation. Further, the same reaction group used for coupling to the carrier protein can be used at a later step in the methods for screening purposes. For small molecules with multiple reactive functional groups, the conjugation can be performed in a manner to ensure that only a single reactive group of the small molecule is coupled to the protein.

Step 2. In particular embodiments, a member of the Camelidae family (camels, llamas, alpacas, vicunas, and guanacos) is immunized against the selected small molecule/carrier protein conjugate (also known as the immunogen) using known immunization methods (FIG. 2) [48]. In particular embodiments, a transgenic animal which contains the human antibody heavy chain locus and is devoid of functional antibody light chains is immunized against the immunogen [49]. In particular embodiments, a mammal with native heavy and light chain antibody loci, or alternatively a transgenic mammal with human heavy and light chain loci is immunized against the immunogen [49]. Immunization should be carried out in the presence of an adjuvant to enhance antibody production [48, 50]. In most instances Complete Freund's adjuvant is effective, however any number of adjuvants can be tried if Freund's fails to give an adequate antibody response or if Freund's adjuvant causes severe side effects in the animals [51, 52]. The amount of hapten/carrier protein conjugate and adjuvant administered, and the timing of booster immunizations varies depending on the animal, but general guidelines can be found in Leenaars M et al and in Pardon E et al [51, 53]. Two to three booster immunizations can be done to increase antibody affinity. Serum samples can be taken and tested by ELISA or similar assays to confirm generation of anti-small molecule/carrier protein conjugate antibodies. For ELISA, the small molecule hapten is conjugated to biotin using the same reactive group as used for carrier protein coupling in Step 1 (FIG. 3). This biotinylated small molecule is then be bound to streptavidin or neutravidin on plates or beads for use in ELISA assays [54]. Biotin covalently attached to various types of flexible linkers and reactive functional groups suitable for chemical conjugation are available from numerous companies such as Thermo Fischer or Sigma Aldrich. Attachment chemistries other than biotin-avidin can also be used.

Step 3. At the end of the immunization period, a blood draw, bone marrow aspiration, spleen collection (in the case of small animals such as mice and rats), or lymph node dissection is done to isolate white blood cells or B-cells [48, 53]. Between 10 and 50 million white blood cells generally are sufficient for subsequent steps. Red blood cells can be depleted by lysis or ficoll gradient separation and RNA extracted from the remaining white cells using any number of methods such as guanidinium thiocyanate-phenol-chloroform extraction (Trizol) or column based kits (Qiagen RNeasy) [55]. Alternatively, after red cell depletion, B-cells can be enriched by flow cytometric sorting or magnetic separation using B-cell specific antibodies, and RNA extracted from this enriched material [55]. Isolated RNA (5 µg) can be reverse transcribed by random primer or oligo-dT based synthesis into cDNA using Invitrogen SuperScript III reverse transcriptase (or another similar enzyme) according to the manufacturer's protocol [56]. Following cDNA synthesis, $E.$ $coli$ RNase H (Invitrogen or other supplier) can be added to the reaction to degrade RNA and increase PCR efficiency in the subsequent steps (specific reaction conditions given by the manufacturer). The cDNA can be used as a template for PCR amplification of heavy chain only (VHH) or single chain antibody (scFV, composed of VH and VL) antigen binding domains. The amplification strategy differs depending on the animal used for immunization.

Figure 5A:
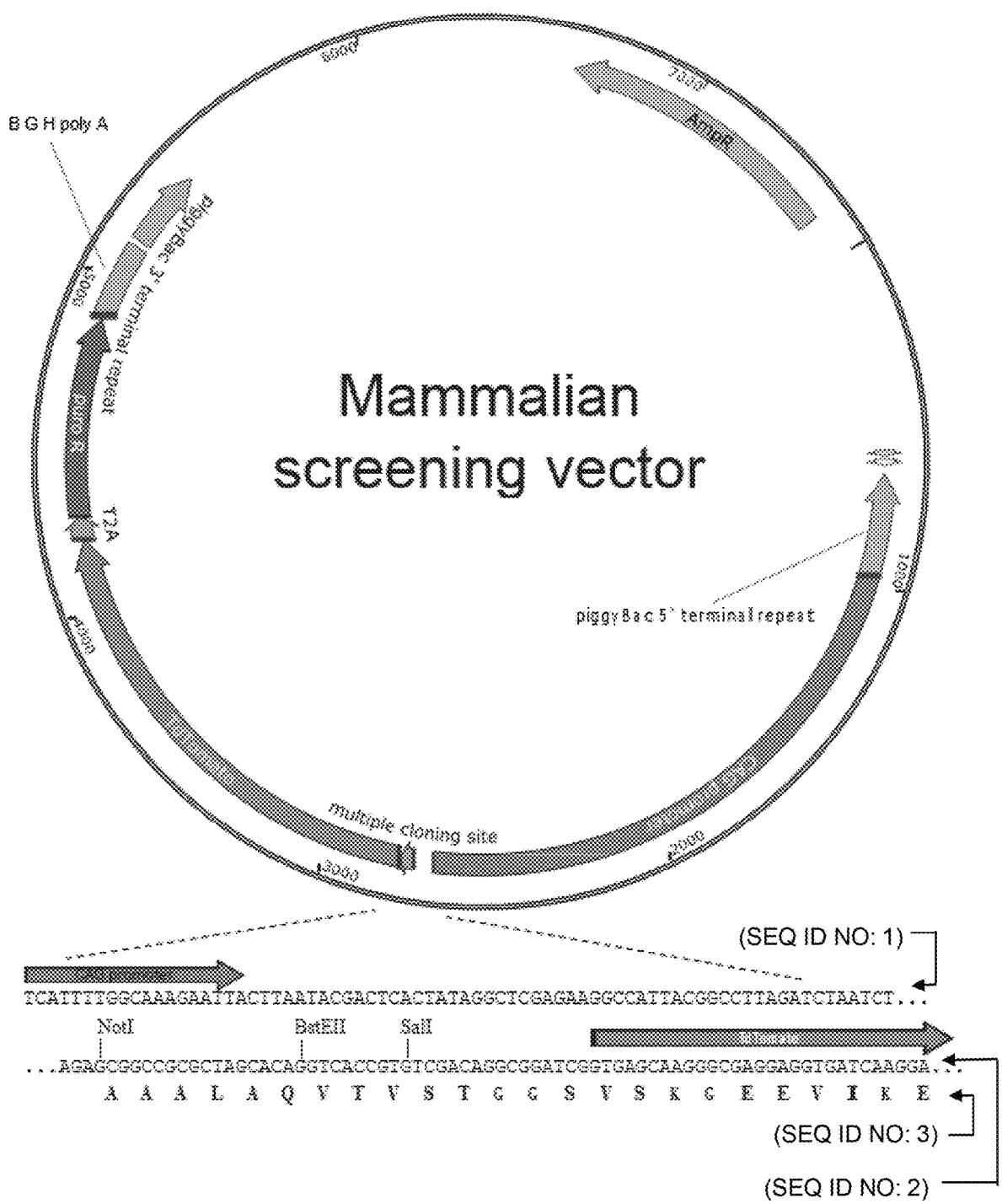
FIGS. 5A-5B. Exemplary screening vectors.
Figure 5B:
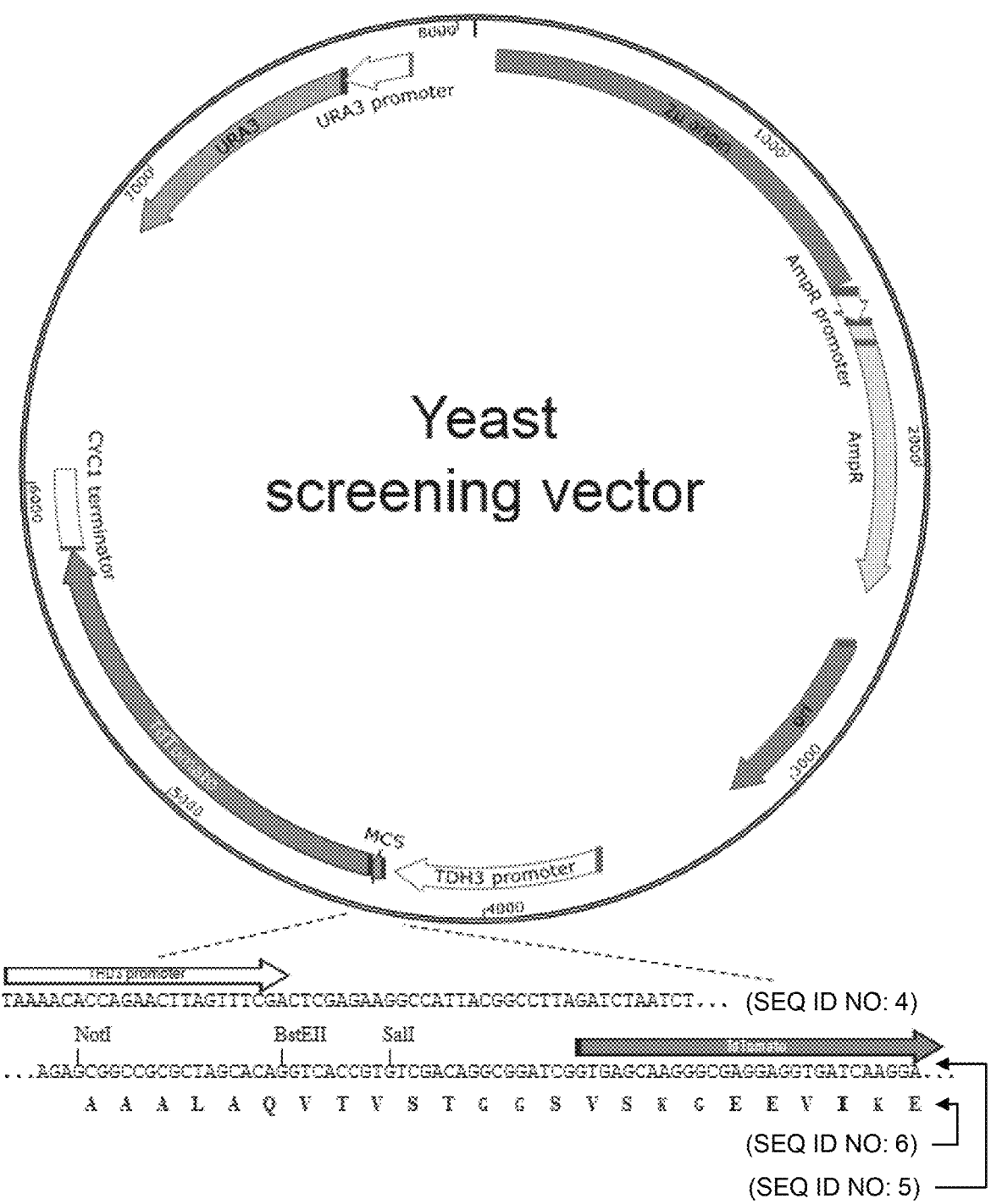

Step 4. For Camelid species, as an example, (or antibody loci derived from Camelid species) two rounds of PCR in a nested format can be used to specifically amplify the rearranged VHH repertoire. The first round PCR can be done with $1^{st}$ round primers (FIGS. 10A-10B) and between 0.5 and 4 µL of cDNA as template. New England Biolabs Q5 polymerase can be used for amplification with reaction conditions given by the manufacturer (other high fidelity polymerases are also suitable). Amplification conditions can be as follows: initial denaturation at 98° C. for 1 min, 30 cycles of 10 seconds 98° C.-30 seconds 55° C.-1 minute 72° C., followed by a 5 minute final extension at 72° C. The number of cycles and the primer annealing temperature may be adjusted to increase product yield. The resulting PCR product can be size separated on an agarose gel and the DNA fragments between 600 and 700 base pairs (corresponding to VHH) can be cut from the gel and purified [56]. Several nanograms (1 to 5 µL) of this product can be then used as a template for a second nested PCR with $2^{nd}$ round primers (FIGS. 10A-10B), again using the Q5 polymerase from New England Biolabs according to manufacturer protocol. PCR amplification conditions can be identical to those of the first round of the PCR. The exact number of PCR cycles may be adjusted to increase product yield or reduce non-specific amplification (general number of cycles in this step can range from 15 to 20). The resulting PCR product (300 to 450 base pairs in length) can be then digested with restriction enzymes NotI and BstEII and ligated into either mammalian or yeast screening vector (FIGS. 5a and 5b) cut with the same enzymes [56].

For transgenic animals with both heavy and light chains derived from humans, the research article by Andris-Widhopf et al., describes a general strategy for cloning rearranged VH and VL antibody repertoires from cDNA and subsequent fusion into a single chain antibody (scFV) format using a long 18 amino acid linker [57]. The protocol as outlined in Andris-Widhopf et al. can be followed but with the following modifications. First, the primer sequences are altered to those listed in FIG. 11. The primer sequences have been altered to allow cloning into the chosen screening vector with compatible restriction enzyme sites (the names of the primers are unchanged from the original protocol). Second, all PCR steps are carried out using New England Biolabs Q5 polymerase or a similar high fidelity polymerase according to the manufacturer instructions, replacing the Taq polymerase used in the original protocol. Third, after final PCR amplification of the scFV library, the PCR product is digested with NotI and SalI restriction enzymes (instead of SfiI) and ligated into either the mammalian or yeast screening vector cut with the same enzymes [56]. Articles by Little et al., and Pansri et al. [58, 59] describe alternate strategies for cloning human based scFV from cDNA. These protocols and associated primer sequences can be altered to be compatible with the methods described herein.

Transgenic animals with only a human heavy chain locus and no functional light chain produce human heavy chain only antibodies (HCAb). FIG. 12 provides primer sequences to amplify the human variable region exons (VHH) of these HCAb from cDNA. In the first PCR, each of the first round forward primers can be paired with one of the first round reverse primers in separate PCR reactions. PCR reactions conditions can be the same as for the Camelid first round VHH amplification (given above). Each of these PCR products (between 0.1 µL and 1 µL) can be then used as a template for a second nested PCR using the corresponding second round forward and reverse primers. Again, PCR conditions can be the same as for the Camelid second round VHH amplification. PCR conditions should be optimized to avoid over-amplification and skewing of the antibody repertoire. The resulting PCR products can be pooled, digested with NotI and SalI restriction enzymes, and ligated into either mammalian or yeast screening vector (FIGS. 5A and 5B) cut with the same enzymes [56].

VHH and scFV libraries may be derived from other species following the basic protocols outlined above, but with alternate species specific primer sequences. VHH and scFV libraries may also be derived from naïve non-immune animals or from synthetic non-natural sequences. Other antibody formats such as light chain only binding domains (VL) can also be adapted for this protocol. However, the number of small molecule/carrier protein conjugate antibodies with sufficient affinity in such libraries is expected to be small, and thus screening such libraries is laborious and not the best method. Additionally, restriction enzyme sites in the primer sequences and corresponding sites in the screening vector can be altered so that other restriction enzymes can be used for the cloning step. Alternately, the VHH or scFV DNA fragments can be inserted into the vector by other cloning methods such as Gibson cloning or SLiCE [60]. For these alternate methods, the primer sequences and corresponding site in the vector can be changed to be made compatible. Any alteration to the primers or screening vector must be made such that the codon reading frame of the VHH or scFV gene remains the same as the TdTomato gene in the screening vector so that a single fusion protein is produced upon translation (VHH-TdTomato or scFV-TdTomato).

Step 5. Following ligation of VHH or scFV amplified sequences into the screening vector, the plasmids can be transformed into MegaX DH10B electrocompetent $E.$ $coli$ from Invitrogen (or similar highly competent bacteria with an efficiency greater than $10^9$ cfu/µg DNA) according to the manufacturer's instructions. Bacteria can be then grown with ampicillin drug selection (100 µg/mL) in a manner that maintains representation of the plasmid library—either on agar plates as described by Hanahan et al. [61] or in semi-solid media as described by Elsaesser and Paysan [62]. Plasmid can be extracted from the bacteria using a Qiagen Plasmid kit according to the manufacturer instructions (or other similar plasmid isolation methods which yield purified plasmid DNA with low endotoxin levels).

Figure 4A:
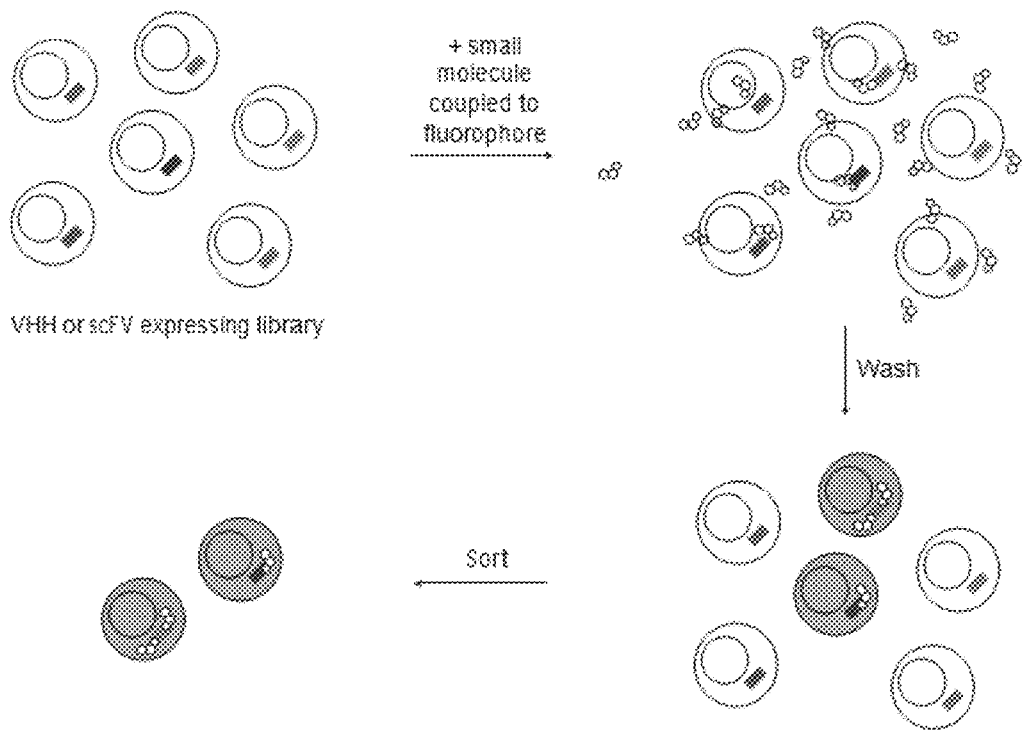
FIGS. 4A-4B. Exemplary screening scheme for antibodies.
Figure 4B:
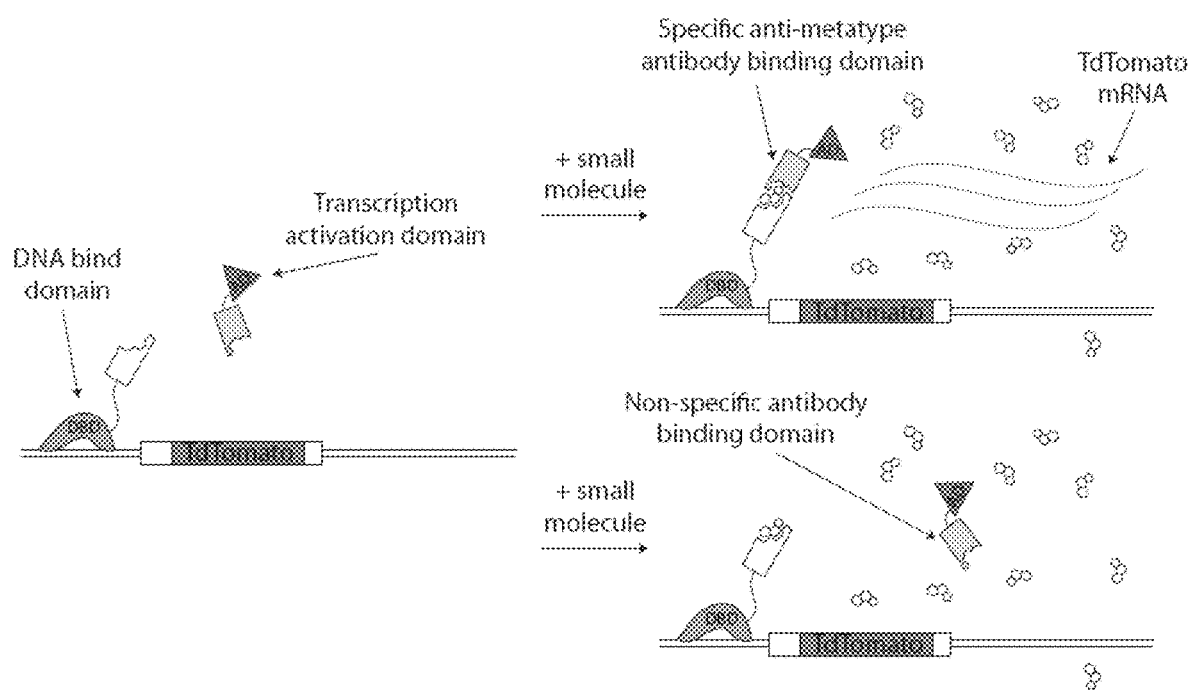

Step 6. In the screening vector, the VHH or scFV cDNA is cloned in frame with the gene for red fluorescent protein TdTomato, creating a fusion gene. Because the VHH or scFV are cloned without a leader peptide, the resulting protein is maintained intracellularly in the cytoplasm (FIG. 4). In the mammalian screening vector the antibody-TdTomato fusion gene can be driven by the strong, ubiquitously expressed, CAGG composite promoter (other strong promoters such as the Eif1α promoter can be substituted) [63]. This promoter also drives the drug selection marker, puromycin N-acetyl-transferase, which is co-cistronic with the antibody-TdTomato gene by inclusion of the 2A peptide. The mammalian screening vector (FIG. 5A) can be a Piggybac based transposon [64]. Co-transfection of this transposon plasmid and the corresponding Piggybac transposase protein into target cells results in integration of the gene construct into the host cell genome and stable expression of the VHH-TdTomato or scFV-TdTomato from the CAGG promoter. Alternate transposon systems (Sleeping Beauty, Tol2, etc.), or viral vectors (retroviral, lentiviral, etc.) can also be used to deliver the antibody-TdTomato fusion gene into mammalian cells (with cloning of the appropriate vectors). In the yeast (S. cerevisiae) screening vector (FIG. 5B), the antibody-TdTomato fusion gene can be driven by the strong TDH3 promoter (weaker promoters such as the ADH1 promoter can be substituted). Plasmid maintenance and propagation can be provided by the 2 micron based origin of replication and the auxotrophic marker URA3 can be used for selection of expressing cells. Alternate promoters or selection genes maybe be substituted into these vectors.

Step 7. To introduce the antibody-TdTomato fusion protein into cells, mammalian cells can be co-transfected with the VHH or scFV library screening plasmids and a plasmid expressing the Piggybac transposase. Any number of mammalian cell lines can be used for screening, such as HeLa, CHO, HEK293, COS7, etc. (in particular embodiments cell lines are non-adherent and easily transfected with DNA or infected by recombinant viruses). Transfection can be done using Invitrogen Lipofectamine 2000 according to the manufacturer protocol, with modifications to ensure single copy integration of the screening vector (that is, each cell has at most one copy of the integrated VHH or scFV transgene). Southern blot, real-time PCR, or similar methods can be used to assess transgene copy number in transfected cells and the amount of vector, transposase, and Lipofectamine (or virus) can be titrated to find the appropriate amount of each to ensure single copy integration. Alternate methods of transfection or cell infection by viruses (if using retroviral or lentiviral delivery) can also be used with similar caveats.

Two days after transfection, the efficiency can be monitored by flow cytometry, using the percent of cells expressing TdTomato as a metric. Two days after transfection cells expressing the VHH or scFV-TdTomato fusion can be selected with 100 ng/mL to 1 µg/mL puromycin (or other antibiotic if another selection marker was used in the screening vector). Selection can be continued until the majority of cells are expressing the transgene (TdTomato positive). The cells can be then screened by flow cytometric sorting as described in Step 8.

For S. cerevisiae, the VHH or scFV screening plasmids can be introduced by high efficiency electroporation as described by Benatuil et al. or by LiAc transformation as described by Gietz and Schiestl [65, 66]. After transformation, yeast can be directly plated onto synthetic media agar plates lacking uracil (or other amino acid if another auxotrophic marker was used in the screening plasmid). Any number of different S. cerevisiae strains may be used, such as the common laboratory S288c strain BY4741 (additional deletion of the ABC transporter gene PDR5, or deletion of the transcriptional regulators PDR1 and PDR3, may aid in the screen described in Step 8 by decreasing efflux of the small molecule [67]). Yeast can be grown under standard conditions for 3-7 days as described in [66], the plates can be then scraped and the yeast resuspended in liquid media for subsequent flow cytometric sorting as described in Step 8.

The number of cells (e.g., mammalian or yeast) used in the protocol depends on the size of the VHH or scFV library. The number of mammalian or yeast cells transfected or transformed should be approximately ten times (or more) the number of unique plasmid sequences in the library. If the library contains $1\times10^6$ unique plasmids (as determined by counting dilutions of the bacteria after transformation), then at least $10\times10^6$ mammalian or yeast cells should be initially transfected or transformed with the library plasmid. This ensures that all members of the antibody library are represented in the cell population and that screening is complete. This can be done iteratively in smaller more manageable pools.

Step 8. To screen the VHH or scFV library for efficient binders of the small molecule/carrier protein conjugate, a flow cytometric assay can be employed which screens for VHH or scFV that are functional (bind antigen, fold properly, and have good stability) in the cytoplasm (FIG. 4A). The small molecule hapten used for immunization in Steps 1 and 2 can be modified by attachment of a fluorescent dye such as BODIPY FL or fluorescein. Both of these dyes are excited efficiently by a 488 nm laser (excitation maxima between 490 and 500 nm) and emit light near 520 nm. The spectra of these dyes are well separated from TdTomato (exmax 554 nm, emmax 581 nm), and thus are suitable for multi-color flow cytometric sorting. Further, both passively diffuse across cell membranes and are ideal for the screening method described here (though both can diffuse across cell membranes, BODIPY FL is less polar than fluorescein and diffuses more quickly).

The small molecule can be coupled to either dye using the same reactive group on the small molecule as was used for coupling to a carrier protein in Step 1 (FIG. 3). The position on the small molecule where the fluorophore is attached is critical. The small molecule-dye coupling is done with a spacer arm (such as polyethylene glycol based linkers) to further minimize steric interference in the binding assay. BODIPY FL and fluorescein are commercially available in multiple formats (including with different spacer arms) which allow direct chemical conjugation using a variety of chemistries (Thermo Fischer, Sigma-Aldrich, etc.). Coupling can be done according to manufacturer instructions and the small molecule-dye conjugate can be purified by column chromatography. Identity and structure of the small molecule-dye conjugate can be confirmed by mass spectrometry or nuclear magnetic resonance spectroscopy based methods. All small molecule-dye conjugates can be then tested for cell permeability.

Ideally, the small molecule chosen in Step 1 is a drug with excellent cell permeability (various tetracyclines or β-Lactam antibiotics such as doxycycline or penicillin are examples). Conjugation of the dye to the small molecule should not overtly affect its permeability. As a simple qualitative test, the small molecule-dye conjugate can be added to mammalian or yeast cells in culture at concentrations ranging from 1 nM to 1 mM for 1 hour. Subsequently, the cells can be immediately examined under a fluorescent microscope with a standard FITC filter set. Cells should be labeled uniformly by the dye, indicating that the small molecule-dye is membrane permeable. If the small molecule-dye conjugate is non-permeable cells will remain unlabeled or alternatively will have focal points of fluorescence corresponding to endosomes (indicating small molecule-dye uptake by pinocytosis rather than simple diffusion). Different spacer arms or dye modifications (such as sulfonation) can be substituted in the conjugate to increase membrane permeability. Alternatively, other dyes with better cell permeability may be tried. After the 1 hour incubation with the small molecule-dye, cells can be twice washed in PBS and resuspended in fresh media (without the small molecule-dye), then analyzed by microscopy or flow cytometry at one to five minute intervals. Depending on the membrane permeability of the small molecule-dye, cell fluorescence will slowly return to background levels—the time at which cell fluorescence has returned to background levels is the "time to background". The rate of small molecule-dye flux out of the cells and the "time to background" can be parameters used in the subsequent screen of the VHH or scFV library.

The cells expressing the VHH or scFV library created in Step 7 can be incubated with the small molecule-dye conjugate for 1 hour, washed twice with PBS, and subsequently placed back into culture conditions. The length of time the cells are cultured before analysis depends on the rate of small molecule-dye flux out of the cells. Cells should be analyzed at or after the "time to background" time point. Cells can be then sorted by a flow cytometer using the appropriate excitation and emission filters, selecting on cells that are TdTomato positive and small molecule-dye positive (BODIPY-FL or fluorescein positive). These sorted cells can be either cultured further or processed to isolate DNA (described in Step 9).

The conceptual framework for this assay is that binding of small molecule by VHH or scFV (which are intracellular) prevents diffusion of the small molecule-dye conjugate out of the cell (FIG. 4A). The result is that cells expressing VHH or scFV which bind the small molecule remain fluorescent by sequestering the small molecule-dye in the cytoplasm, whereas cells expressing non-binding VHH or scFV lose the small molecule-dye conjugate as it is diluted out. VHH or scFV which have small dissociation constants (tighter binding) with the small molecule are expected to retain the small molecule longer in the cytoplasm. Hence cells can also be sorted after longer time periods to specifically select for cells which express high affinity binding VHH or scFV. Alternatively cells can be sorted based on the ratio of TdTomato to small molecule-dye, selecting for cells which are brighter on the small molecule-dye axis relative to TdTomato.

Although the described assay uses TdTomato and BODIPY FL/fluorescein, other combinations of fluorescent protein and fluorescent dye can be used if the excitation and emission spectra of the two species can be resolved by flow cytometry, the fluorescent protein does not interfere with VHH or scFV binding, and the fluorescent dye is cell permeable and does not interfere with small molecule binding.

Alternative methods of VHH or scFV screening, such as phage display or yeast surface display can also be employed (as described in detail in [68]). However, because these methods do not screen for VHH or scFV which are functional (i.e. bind antigen, fold properly, stable) in the intracellular space, they are not the best method and the recovered VHH or scFV must still be further screened for cytoplasmic function [69]. ScFV antibody libraries in particular may benefit from first using a surface display screen as many scFV do not fold properly in the intracellular space. The scFV recovered in such a screen can then be tested in the intracellular small molecule-dye binding assay described above; those which do not function intracellularly can be mutated or grafted onto stable scFV frameworks known to promote folding and re-tested for binding ability [70, 71]. These surface display methods may require attachment of the small molecule to a solid surface. Again, the small molecule is attached using the same reactive group as was used for coupling to a carrier protein in Step 1.

Step 9. The specificity of the VHH or scFV expressed by the sorted cells can be determined by flow cytometry using the unlabeled small molecule as a competitor. These tests can ensure that selected VHH or scFV bind to the small molecule alone and not to the attached linker or fluorophore; in addition they can provide data about VHH or scFV affinity and binding kinetics. The advantage of these cell based assays is that binding by the VHH or scFV is measured in a cellular context.

The sorted cell population from Step 8 can be single cell cloned (e.g., by flow cytometric sorting or limiting dilution). Individual clones can be expanded and re-tested individually for small molecule binding using the assay from Step 8 and high affinity binding cell clones can be selected (clones which maintain small molecule-dye binding for long time periods (e.g., 4 minutes or more after wash out). Cell expansion can also be done in bulk culture followed by additional rounds of cell sorting to further enrich for cells expressing high affinity binding VHH or scFV; followed by single cell cloning and expansion.

Each cell clone (expressing a single VHH or scFV) can be incubated with a set concentration of the small molecule-dye and increasing amounts of the unlabeled small molecule in a series of wells. For example the concentration of dye labeled to unlabeled species might vary such: 1 to 0, 1 to 0.1, 1 to 0.25, 1 to 0.5, 1 to 1, 1 to 2, 1 to 4, 1 to 10, 1 to 100. After several hours incubation to allow equilibration, cells can be washed thoroughly and analyzed by flow cytometry. In this assay, the unlabeled small molecule acts as a competitor to the dye labeled species for VHH or scFV binding. For VHH or scFV which bind the small molecule specifically (and not to linker or fluorophore), as the concentration of unlabeled small molecule increases, the fluorescence of the cells decreases in direct proportion because both small molecule species bind the antibody with equal affinity. Alternatively, for VHH or scFV whose binding is wholly or partially dependent on the linker or fluorophore, unlabeled small molecule does not compete effectively for antibody binding and cell fluorescence does not decrease proportionally.

Cell clones expressing VHH or scFV which bind specifically to the small molecule can be further tested to determine the dissociation rate of the small molecule from the antibody. Each cell clone can be incubated in culture with either vehicle alone or saturating amounts (1 nM to 1 mM) of the small molecule-dye conjugate for several hours to achieve saturation binding of the VHH or scFV. A 100 fold excess of unlabeled small molecule can be then added to the culture; subsequently, at regular time intervals (1 to 5 minutes) cells can be quickly washed and analyzed by flow cytometry for retention of the small molecule-dye conjugate. In this assay, the excess of unlabeled small molecule effectively prevents re-binding of the dye labeled molecule and diminishes cell fluorescence over time. This time series data can be then used to estimate the off rate of the small molecule from the VHH or scFV [72]. Cell clones expressing VHH or scFV which bind to the small molecule tightly and selectively can be chosen for subsequent steps. Alternatively, if no such VHH or scFV are recovered, the best performing clones can be isolated and systematically mutated as described in Steps 10 and 11 to generate variants with desired properties.

Chemical variants of the small molecule can also be tested as described above to determine the specificity of the VHH or scFV for families of molecules. For example if doxycycline is used as the small molecule hapten, other tetracyclines (such as tetracycline, minocycline, tigecycline, etc.) can be tested for their ability to bind the VHH or scFV in competition against a doxycycline-dye conjugate. Similarly, if penicillin is used as the small molecule hapten, other β-lactam molecules can be tested for binding to the binding domains.

An alternative method is to use high throughput DNA sequencing technologies such as the Illumina HiSeq or Roche 454 (or other similar technologies) to sequence entire populations of VHH or scFV in cell pools rather than single cell cloning. VHH or scFV sequences can be recovered from cells using the PCR protocol as described in Step 10. The VHH or scFV PCR products can be cut with NotI and SalI restriction enzymes, purified by agarose gel size selection, and appropriate DNA adapter sequences are ligated on (specific for each sequencing platform). The adaptor sequences and sequencing protocols differ for each sequencing technology and can be obtained from the particular manufacturer. Because of the size of VHH and scFV, sequencing technologies which are capable of long DNA reads (paired end reads of >250 bp and single end reads of >500 bp) are preferable. Cells expressing VHH or scFV are sorted by flow cytometry for small molecule-dye conjugate binding as described in step 8; or sorted for specificity as described in step 9 (sorting for cells whose binding of the dye conjugate is disrupted by excess unlabeled small molecule). VHH or scFV DNA sequences which are highly enriched in the target sorted population compared with the initial parent cell population can be uniquely amplified with sequence specific primers or synthesized de novo (by DNA synthesis) and cloned into the appropriate mammalian or yeast screening vector. These VHH or scFV clones are then introduced into cells by transposition (as described in step 7) and re-tested for specificity and affinity as in step 9.

Step 10. VHH or scFV sequences can be recovered from selected cell clones by PCR using 50-200 ng genomic DNA and the genomic DNA amplification primers given in FIG. 10C. PCR can be done with Q5 polymerase from New England Biolabs (or a similar robust high fidelity polymerase) according to manufacturer instructions. Amplification conditions can be as follows: initial denaturation at 98° C. for 1 min, 25 to 35 cycles of 10 seconds 98° C.-30 seconds 60° C.-1 minute 72° C., followed by a 5 minute final extension at 72° C. Amplified DNA can be digested with NotI and SalI restriction enzymes and ligated to the mammalian or yeast screening vector cut with the same enzymes.

Ligated plasmids can be transformed into *E. coli* strain DH5a or DH10B (or other similar strains used for routine cloning). Plasmid DNA from individual bacterial clones can be checked by diagnostic restriction digest and sequenced by standard Sanger sequencing using the genomic DNA amplification primers in FIG. 10C.

Step 11. If the VHH or scFV are derived from non-human antibody sequences, they can be "humanized" using procedures outlined in, for example, Vincke et al. [73] for VHH from Camelid species, or Philibert et al. [71], Kuramochi et al. [74], and/or Olimpieri et al. [75] for example, for scFV derived from mouse or other species. Although not absolutely necessary, humanization of the antibodies is the best method if the proteins are to be used in human gene therapy applications. Generally humaniazation procedures include grafting the CDRs or the specificity-determining residues (SDR) of the non-human antibody onto a human antibody framework; reducing the immunogenicity of the foreign antibodies in human hosts. Using the VHH or scFV sequences from Step 10, an appropriate human antibody framework can be selected for CDR or SDR grafting.

One consequence of grafting is often the loss of binding affinity for the target antigen. To recover antigen specificity and affinity after grafting, grafted VHH or scFV clones can be mutated either by point mutagenesis or DNA shuffling using known techniques [68, 76]; subsequently these mutants can be screened (either individually or in a library format) as described in Steps 8 and 9 to select for antibodies with specificity and binding affinity similar to the original VHH or scFV. That is, binding affinity should not be reduced in a statistically-significant manner. Iterative rounds of mutagenesis and selection can be done to obtain VHH or scFV with the desired specificity and binding affinity. In addition to recovering or improving specificity and binding affinity after humanization, VHH or scFV clones can be mutated to generate antibodies with altered properties such as better folding and stability or altered specificity for chemical variants of the small molecule (other characteristics may also be selected for).

Figure 6:
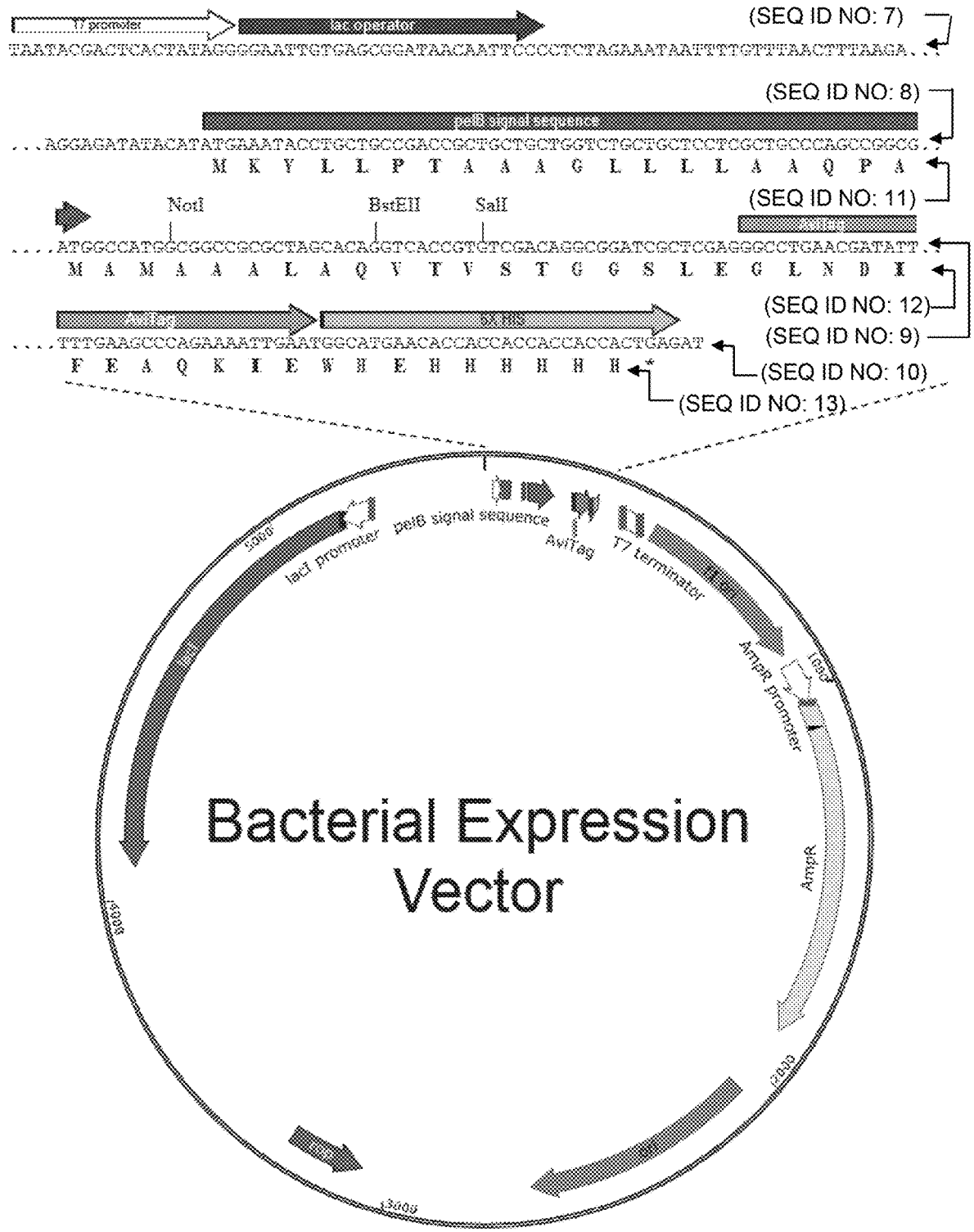
FIG. 6. Exemplary bacterial expression vector.

Step 12. Once cells expressing VHH or scFV with very high binding affinity for the small molecule are identified, DNA from these individual cell clones can be isolated using standard methods [56]. Using this DNA as a template VHH or scFV sequences can be recovered by PCR with genomic DNA amplification primers as described in Step 9. Amplified DNA can be digested with NotI (or NcoI) and SalI restriction enzymes and ligated to the bacterial expression vector (e.g., FIG. 6) cut with the same enzymes. Alternatively VHH or scFV sequences in the screening vectors can be directly transferred to the bacterial expression vector by standard molecular cloning [56].

Ligated plasmids can be transformed into the *E. coli* strain BL21(DE3) (or similar strains designed for IPTG inducible T7 promoter driven protein expression) by standard methods [56]. These bacteria can be used to produce purified VHH or scFV protein for subsequent steps. The bacterial expression vector (e.g., FIG. 6) can be designed such that cloned VHH or scFV are tagged on the C-terminal end with two purification tags: e.g., the biotin targeting AviTag and a 6× polyhistidine tag. The AviTag is a target for the bacterial BirA biotin ligase enzyme, which can covalently attach a biotin group to the lysine in the AviTag either in vivo or in vitro [77]. The biotin moiety can then be used for streptavidin or avidin based protein purification. The 6× histidine binds tightly to nickel or cobalt affinity resins and allows for protein purification using gentle conditions. Either or both tags may be used in the affinity purification of VHH or scFV.

Many manufacturers and vendors, e.g. Novagen, Thermo Scientific, Sigma-Aldrich, provide reagents and detailed protocols for protein expression using the IPTG inducible T7 promoter system. Similarly, these companies also provide reagents and protocols for both AviTag (biotin) and polyhistidine tag based protein purification.

Step 13. The binding affinity of purified VHH or scFV proteins for the small molecule can be confirmed by, for example, surface plasmon resonance (SPR) [78]. SPR chips which bind biotin or the 6× histidine tag are available from numerous manufacturers such as Biorad and GE Healthcare. Moreover, these companies have specialized SPR chips and protocols designed for detection of small molecule binding. These specialized protocols can be necessary because of the low mass of the small molecule. Determination of binding affinity and binding kinetics can be done according to the manufacturer's protocol.

Step 14. For clarity, the small molecule binding VHH or scFV clone isolated as described above and chosen for use in subsequent steps is called antibody binder 1 (AB1). The purified AB1/small molecule complex is used to immunize animals to generate antibodies directed against the AB1 protein/small molecule complex—so called anti-metatype antibodies. For effective generation of anti-metatype antibodies, it is important that the small molecule remains bound to AB1 while in the animal during immunization. Thus one critical aspect is that the selected AB1 has high affinity binding to the small molecule (determined, for example, as described in Steps 9 and 13). Although it is possible to fix the small molecule to AB1 by chemical crosslinking, such modification alters the three dimensional conformation of the protein and thus is not the best method for generation of anti-metatype antibodies.

Purified AB1/small molecule complex can be used to immunize an animal. In particular embodiments, a member of the Camelidae family (camels, llamas, alpacas, vicunas, and guanacos) can be immunized against the AB1/small molecule complex using known immunization methods [48]. In particular embodiments, a transgenic animal which contains the human antibody heavy chain locus and is devoid of functional antibody light chains can be immunized against the AB1/small molecule complex [49]. In another embodiment a mammal with native heavy and light chain antibody loci, or alternatively a transgenic mammal with human heavy and light chain loci can be immunized against the AB1/small molecule complex [49]. In all cases, immunization can be carried out in the presence of adjuvant to enhance antibody production [48, 50]. In most instances Complete Freund's adjuvant is effective, however any number of adjuvants can be tried if Freund's fails to give an adequate antibody response or if Freund's adjuvant causes severe side effects in the animals [51, 52].

To ensure that AB1 remains substantially bound to the small molecule, concentration of the small molecule in the animals can be maintained by repeated dosing of the small molecule, delivered either orally or by injection. For example, doxycycline can be given to mice, rats, and rabbits by inclusion in the drinking water at 2 mg/Ml [79], while camelid animals can be given doxycycline by subcutaneous injection at 20 mg/kg animal weight every 2-3 days[79]. The dosing of other small molecules and the administration route can be different for various molecules and animals, and depends on the bioavailability of the molecule, its clearance rate from the body, gut absorption, and many other parameters. The Merck Veterinary Manual [79], Plumb's Veterinary Drug Handbook [80], and other similar resources contain dosing information about common generic small molecule drugs such as antibiotics. For other classes of small molecules, empirical testing may be needed to determine the correct dosing. Dosing should be done at the highest possible level that does not cause harm to the animal. For small molecules which are not well tolerated or are toxic, an in vitro screening method can be adopted to find anti-metatype antibodies (step 15).

Administration of the small molecule to the animal can begin 1-2 days prior to immunization. AB1 can be mixed with a saturating amount of the small molecule and adjuvant and injected into the recipient animal. The amount of AB1/small molecule complex and adjuvant administered, and the timing of booster immunizations varies depending on the animal, but general guidelines can be found in Leenaars M et al. and in Pardon et al. [51, 53]. Two to three booster immunizations can be done to increase antibody affinity. Dosing of the small molecule can continue throughout the immunization period.

Serum samples can be taken and tested by ELISA or similar assays to confirm generation of anti-metatype antibodies. For ELISA, purified AB1 protein can be biotinylated by BirA in vitro and then bound to streptavidin or neutravidin on plates or beads for use in ELISA assays [54, 77]. ELISA can be done in the presence of a saturating amount of the small molecule. Attachment chemistries other than biotin-avidin can also be used.

Figure 8A:
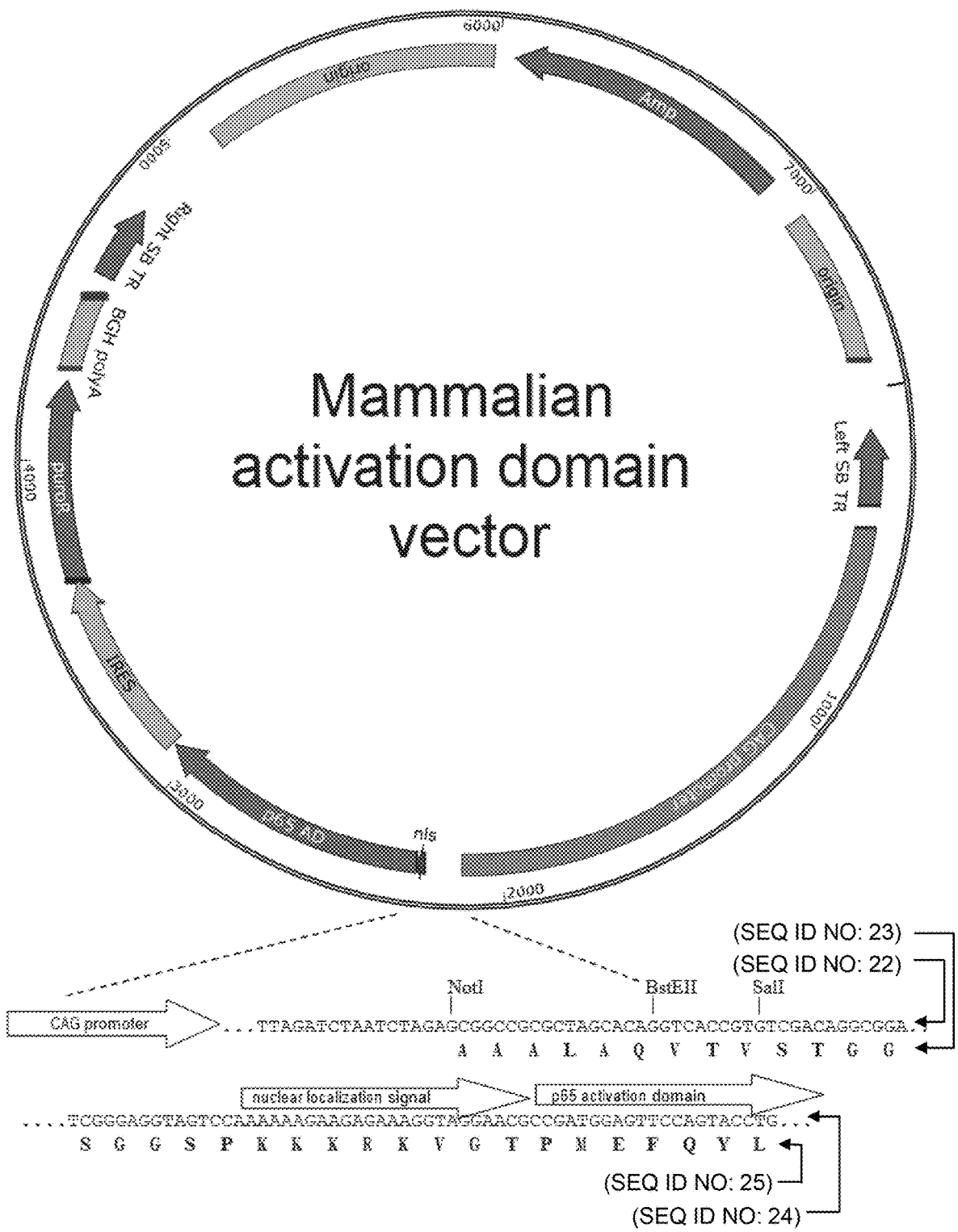
FIGS. 8A-8B. Exemplary activation domain vectors.
Figure 8B:
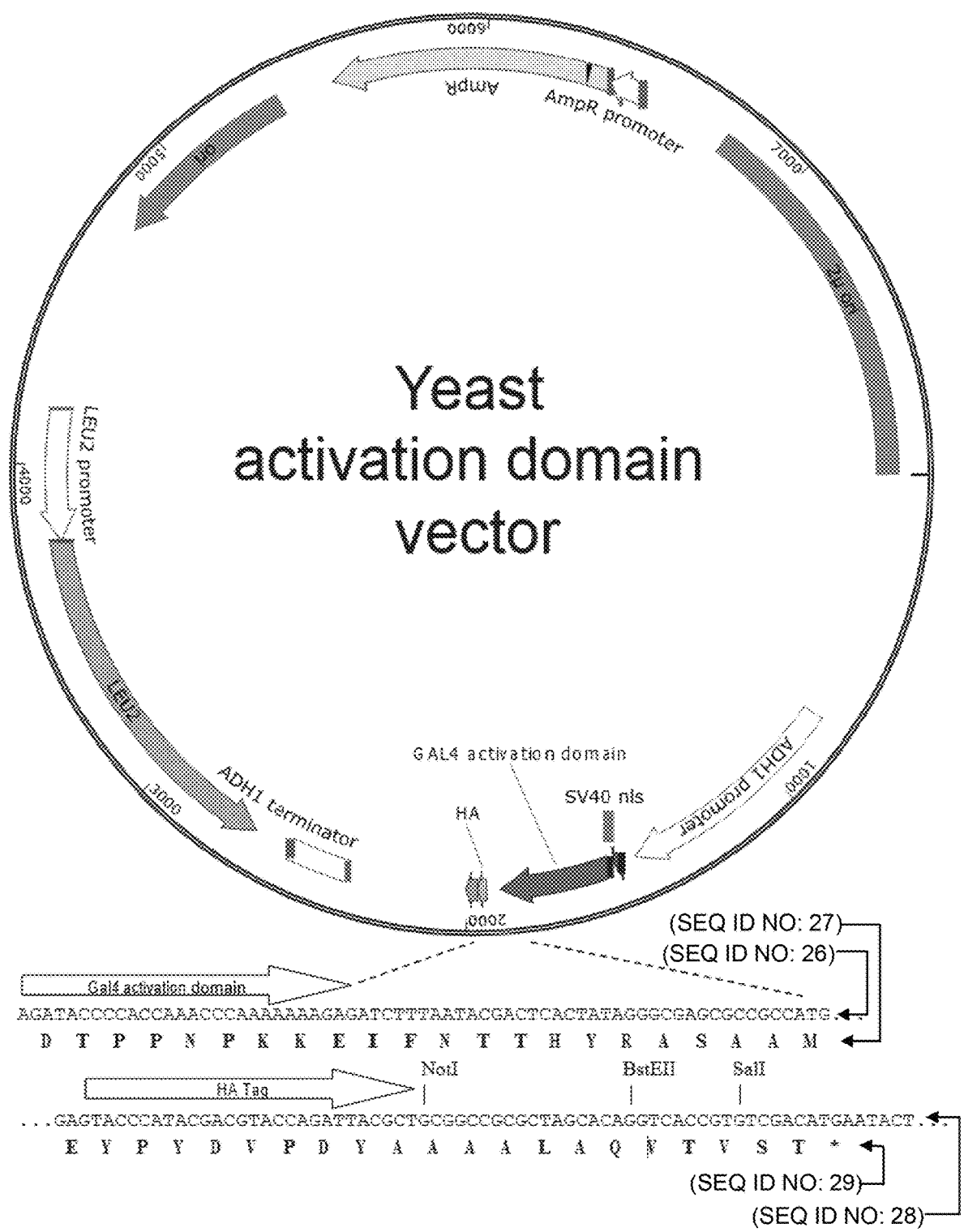

Step 15. At the end of the immunization period, steps 3 and 4 are repeated as described above, except that the PCR amplified cDNA is digested with restriction enzymes NotI and BstEII (Camelid based VHH), or NotI and SalI (human scFV or VHH), and ligated to either the mammalian or yeast activation domain vector cut with the same enzymes (FIGS. 8a and 8b). These vectors are designed such that the cloned VHH or scFV is in frame with a C-terminal transcriptional activation domain (AD): p65 AD in the mammalian vector, and Gal4 AD in the yeast vector. The ligated plasmids are then transformed into E. coli for library expansion and subsequent plasmid purification as outlined in step 5.

VHH or scFV activation domain libraries can also be created from the antibody repertoires of naïve animals using the methods described here. Such libraries should be used in instances where the chosen small molecule is not well tolerated by animals and as such immune antibody libraries cannot be created. However, because the number of VHH or scFV which will bind to AB1/small molecule in such libraries is expected to be very small, a much greater number of clones must be screened. The time and cost associated with such large screens makes this option non-ideal.

Step 16. In order to conduct a screen for VHH or scFV which bind the AB1/small molecule complex, a modified two hybrid screen can be conducted [81]. For example, in one exemplary assay, one dimerizing protein of the CID is fused with the DNA binding domain of the yeast Gal4 gene and the dimerizing protein of the CID is fused to a transcriptional activation domain. Binding of the dimerizing proteins to each another brings the activation domain into proximity of the DNA binding domain and activates transcription of reporter genes driven by Gal4 response element (GRE) dependent promoters. In this screen, a third element can be introduced—namely the small molecule. The screen can be conducted to find antibody pairs (AB1 and the anti-metatype antibody) whose interaction is dependent on the presence of the small molecule (in the absence of the small molecule the AB1 protein and the anti-metatype antibody do not bind to each other). As outlined by Stynen et al. [81], many similar interaction assays are possible and these alternate methods can be adapted to screen for AB1/AB2 dimerizing protein pairs as described herein.

Figure 7A:
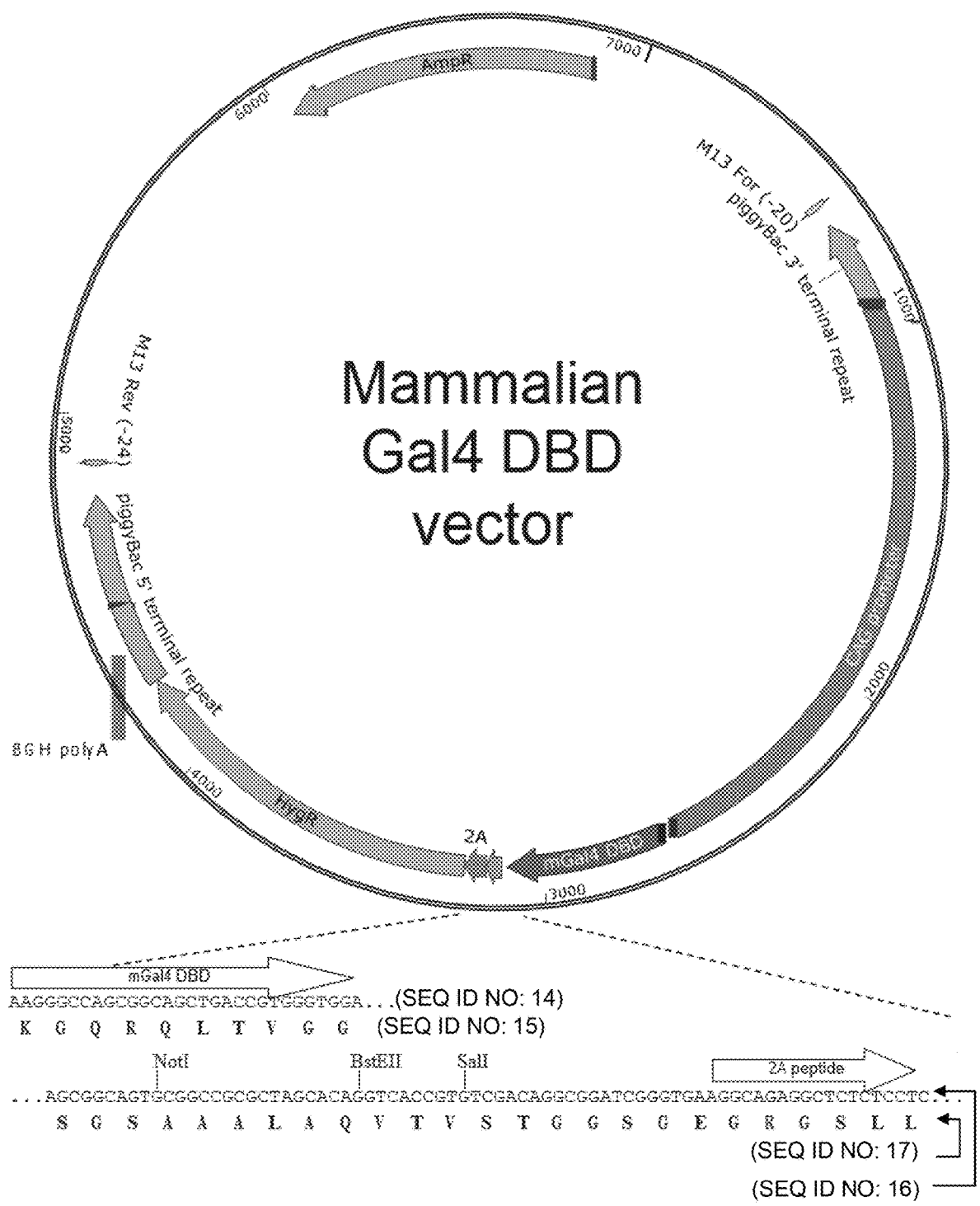
FIGS. 7A-7B. Exemplary Gal4 DBD vectors.
Figure 9:
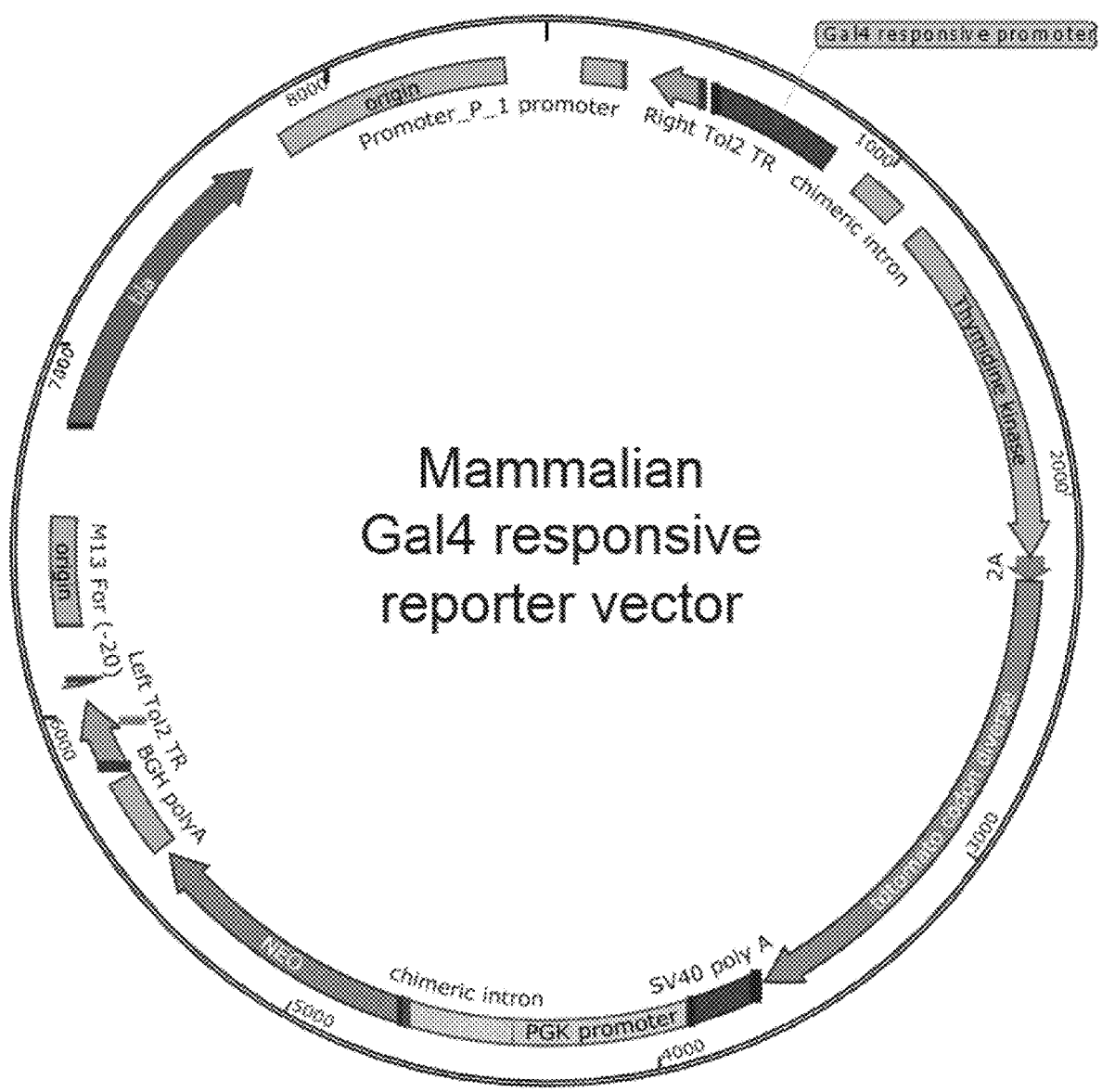
FIG. 9. Exemplary mammalian Gal4 responsive reporter vector and mammalian control Gal4-VP16 vector.

For mammalian cells, the mammalian Gal4 responder plasmid (FIG. 9) can be co-transfected with a plasmid expressing Tol2 transposase [82] into target cells. As with previous steps, any number of mammalian cell lines can be used for screening, such as HeLa, CHO, HEK293, COS7, etc. (in particular embodiments cell lines are non-adherent and easily transfected with DNA or infected by recombinant viruses). Transfection is done using Invitrogen Lipofectamine 2000 according to the manufacturer's protocol. Alternate methods of transfection or cell infection by viruses (if using retroviral or lentiviral delivery) can also be used. Cells with integrated copies of the Gal4 responder construct can be selected by addition of the drug G418 to growth media (between 50 μg/mL and 500 μg/mL depending on the sensitivity of the particular cell type). Cells can be single cell cloned by flow cytometric sorting or limiting dilution and individual clones can be screened for absence of TdTomato fluorescence (to ensure absence of background transcription). Clones without TdTomato fluorescence can be further screened for response to a Gal4 DNA binding domain-VP16 activation domain fusion protein control (delivered by transient transfection of a control plasmid, FIG. 9). Cell clones which become TdTomato positive upon transfection of the control plasmid (as judged by flow cytometry), and thus are responsive to Gal4 based activation can be used as the reporter cell lines. The open reading frame of AB1 can be transferred by standard cloning procedures into the empty mammalian Gal4 DBD vector (FIG. 7a). The AB1-Gal4 DBD plasmid can be then introduced into the reporter cell line by co-transfection with a plasmid expressing the Piggybac transposase [64]. Cells with the AB1-Gal4 DBD construct integrated into the genome can be selected by addition of Hygromycin B to the culture media (between 50 μg/mL and 500 μg/mL depending on the sensitivity of the particular cell type). These cells are single cell cloned and individual clones assayed for AB1-Gal4 DBD expression by either realtime PCR, immunoblot using an anti-Gal4 antibody, or staining with the small molecule-dye conjugate (step 8)[56]. Clones that have a high level of AB1-Gal4 DBD protein can be selected for library screening as described below.

The VHH or scFV library cloned into the mammalian activation domain vector (Step 15) can be introduced into the cell line by co-transfection of the library plasmid with a plasmid expressing, for example, the Sleeping Beauty transposase [83]. Transfection can be done using Invitrogen Lipofectamine 2000 according to the manufacturer's protocol, with modifications as necessary to ensure single copy integration of the activation domain vector (that is, each cell has at most one copy of the integrated VHH or scFV transgene). Southern blot, real-time PCR, or similar methods can be used to assess transgene copy number in transfected cells and the amount of vector, transposase, and Lipofectamine (or virus) can be titrated to find the appropriate amount of each to ensure single copy integration. Alternate methods of transfection or cell infection by viruses (if using retroviral or lentiviral delivery) can also be used with similar caveats. Two days after transfection cells expressing the VHH or scFV-p65 AD fusion can be selected with 100 ng/mL to 1 μg/mL puromycin.

The majority of antibodies raised against the AB1/small molecule complex are expected to be directed against the framework regions or the variable regions of AB1 and not specific for the bound conformation. Such antibodies form a complex with AB1 independent of the small molecule; thus VHH or scFV-p65 AD which bind to AB1-Gal4 DBD in the absence of small molecule constitutively drive expression of the Gal4 reporter in cells. To screen out these small molecule independent binders, counter selection can be employed. The Gal4 reporter transcribes both TdTomato and the viral protein thymidine kinase (FIG. 7A). The thymidine kinase enzyme coverts the drug Ganciclovir into a toxic nucleoside analog, killing cells which express the enzyme (either Ganciclovir alone or thymidine kinase alone are innocuous). The reporter cells with the VHH or scFV-p65 AD fusion library can be treated with Ganciclovir (0.5 μM-10 μM) for several days until flow cytometric analysis determines that all TdTomato positive cells have been eliminated from the culture. The cells can be then washed free of Ganciclovir and placed back into culture. Other similar drug inducible suicide genes can used in place of thymidine kinase, such as an inducible caspase 9 [31]. Alternatively, the cell population can be sorted by flow cytometry to remove TdTomato positive cells, selecting on the non-fluorescent population.

After elimination of these small molecule independent antibodies from the cell population, a positive selection step can be employed to enrich for cells in which VHH or scFV binding to AB1 requires the small molecule. Small molecule can be added at saturating concentrations (as determined in Step 9) to the cells in culture. Cells can be cultured for 2-3 days and then sorted by flow cytometry, selecting on cells that are TdTomato positive. These cells can be either single cell cloned by flow sorting or limiting dilution. Individual cell clones can be exposed to the small molecule at increasing concentrations (1 nM-1 mM) to determine the sensitivity of TdTomato expression to levels of the small molecule (ideal clones are non-fluorescent in the absence of the small molecule, but whose fluorescence increases with increasing small molecule concentration). VHH or scFV sequences can be recovered from selected cell clones by PCR using 50-200 ng genomic DNA and the genomic DNA amplification primers given in FIG. 10C. PCR products can be sequenced directly using the T7 promoter primer or can be cloned into mammalian activation domain vector (FIG. 8A, using the compatible restriction enzyme sites) and then sequenced. These VHH or scFV can be re-introduced into cells as described above for re-testing and confirmation. Clones which retest positive are anti-metatype VHH or scFV specific for the AB1/small molecule complex.

Figure 7B:
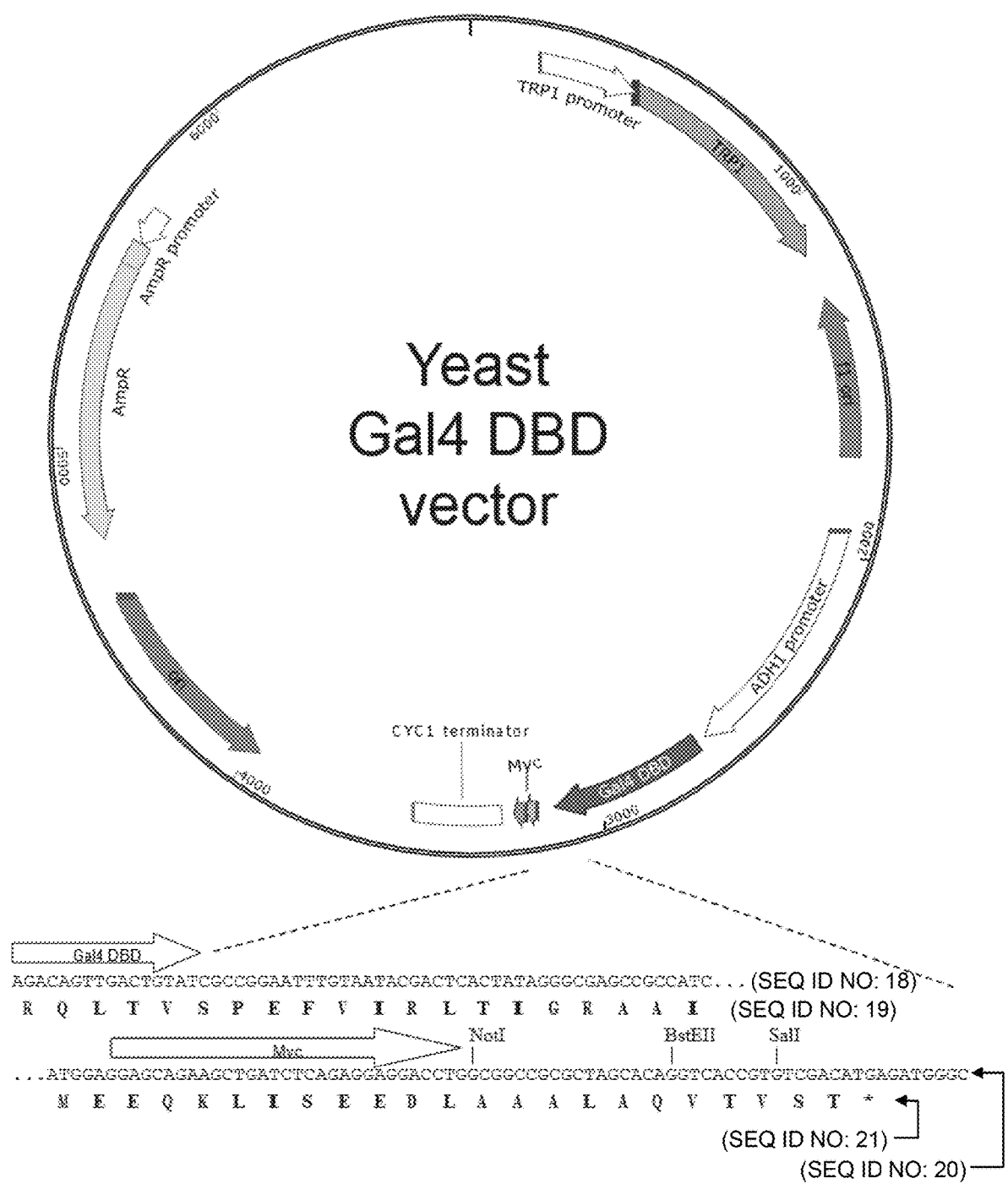

For S. cerevisiae, the screen can be done in, for example, either MaV103 (MATa) or MaV203 (MATa) strains [84]. These strains contain three Gal4 reporter genes: HIS3, which provides growth in media lacking histidine, LacZ, for colorimetric detection of Gal4 transcription, and URA3, which provides growth in media lacking uracil as well as sensitivity to the drug 5-fluoroorotic acid (5-FOA) for counter selection. This strain can be further modified by deletion of the ABC transporter gene PDR5, or deletion of the transcriptional regulators PDR1 and PDR3, which may aid in the screen by decreasing efflux of the small molecule [67]. The open reading frame of AB1 can be transferred by standard cloning procedures into the empty yeast Gal4 DBD integrating vector (FIG. 7B). This AB1-Gal4 DBD vector can be linearized by restriction digest with the enzyme AscI, and then introduced into the screening strain by standard LiAc transformation [85]. Transformed cells can be selected by plating onto synthetic media agar plates lacking tryptophan. Expression of AB1-Gal4 DBD in transformed cells can be confirmed by realtime PCR, immunoblot using an anti-Gal4 or anti-myc antibody, or staining with the small molecule-dye conjugate (Step 8) [56]. This AB1-Gal4 DBD expressing strain can be then used for library screening. The VHH or scFV library cloned into the yeast activation domain library (FIG. 8B) can be introduced into the screening strain by high efficiency LiAc transformation or electroporation [65, 66]. Cells can be plated onto synthetic media agar plates lacking tryptophan and leucine to select for cells with the VHH or scFV activation domain plasmid. After 5-7 days growth, cell colonies (now containing the entire VHH or scFV activation domain library) can be replica plated onto synthetic media agar plates containing the small molecule, and lacking the amino acids leucine, histidine, and uracil (the small molecule can be added to the agar plates at saturating concentrations). For small molecules which are not stable on agar plates, the cells can be selected in liquid culture with the small molecule. Cells in which the VHH or scFV binds to AB1 and activates transcription of the reporter genes will be able to grow on these selection plates.

Subsequently, the cells can be subjected to counter selection to screen against small molecule independent VHH or scFV binders. The surviving yeast can be replica plated onto complete synthetic media agar plates without the small molecule and containing 5-FOA (0.05%-0.2%). VHH or scFV which bind to AB1 in the absence of small molecule will continuously transcribe the URA3 selection marker. Cells expressing URA3 are killed by 5-FOA, while cells lacking URA3 survive [86].

The surviving cells represent those in which VHH or scFV binds to the AB1/small molecule complex, but not AB1 alone. As with mammalian cells, these cells can be further screened to identify cells with stronger binding interactions. Individual clones can be grown on appropriate selection plates or in liquid culture (-trp, -leu) containing X-gal and increasing concentrations of the small molecule. As the concentration of the small molecule is increased the interaction between the VHH or scFV AD and AB1 Gal4 DBD should also increase, giving rise to more β-galactosidase enzyme (due to the Gal4 driven LacZ gene) and more X-gal cleavage and colonies of deeper blue. This assay can also be made quantitative as described by Mockli and Auerbach [87]. A similar assay can be performed by plating the cells in increasing concentrations of 3-amino-1,2,4-triazole (3-AT, 1 mM-100 mM). 3-AT is a competitive inhibitor of the HIS3 gene. As such, greater levels of HIS3 are required to overcome increasing concentrations of 3-AT [88]. Those cells which survive the highest concentrations of 3-AT at a given concentration of small molecule represent cells with greater amounts of HIS3 transcription driven by the VHH or scFV interaction with the AB1/small molecule complex. VHH or scFV sequences can be recovered from selected clones by PCR using 50-200 ng genomic DNA and the genomic DNA amplification primers given in FIG. 10C. PCR products can be sequenced directly using the T7 promoter primer or can be cloned into yeast activation domain vector (FIG. 8B, using the compatible restriction enzyme sites) and then sequenced. These VHH or scFV can be re-introduced into cells as described above for re-testing and confirmation. Clones which retest positive are anti-metatype VHH or scFV specific for the AB1/small molecule complex.

Step 17. If non-human antibody sequences were used to derive the anti-metatype VHH or scFV, these can be humanized as described in Step 11. After humanization, iterative rounds of mutagenesis and reselection using, for example, the two hybrid screen described in Step 16 can be done to recover binding affinity and specificity. In addition to recovering or improving specificity and affinity after humanization, anti-metatype VHH or scFV clones can be mutated to generate antibodies with altered properties such as better folding and stability or altered specificity (other characteristics may also be selected for).

Step 18. For clarity, the anti-metatype VHH or scFV clones isolated as described above are called antibody binder 2 (AB2). Once satisfactory AB1/AB2 pairs are isolated, either member may be mutated to alter the kinetics, binding affinities, or small molecule specificity of the complex. The two hybrid screening methods described above can be employed to find mutant AB1/AB2 pairs with desired properties.

To adapt the two hybrid assays for measurement of kinetics or stability of the complex, Gal4 reporter genes with shorter half-lives (such as destabilized fluorescent proteins or luciferase) can be used. The short half-life of such proteins allows for assessment of complex stability after wash out of the dimerizing small molecule. Thus screens can be conducted for mutant AB1 or AB2 proteins which either prolong or shorten the half-life of the complex.

The specificity of the AB1/AB2 pairs for the particular small molecule can be tested by using chemically related compounds as dimerizers in the two hybrid assays described in Step 17. For example if doxycycline is used as the small molecule hapten, other tetracyclines (such as tetracycline, minocycline, tigecycline, etc.) can be tested for their ability to dimerize AB1 and AB2. Similarly, if penicillin is used as the small molecule hapten, other β-lactam molecules can be tested. Further, AB1 or AB2 proteins can be mutated and subsequently screened for mutants with altered specificity for these other related compounds.

Other compounds which are chemically related to the small molecule can be screened for those which destabilize the AB1/AB2/small molecule complex. Some related chemical variants may bind with equal or tighter affinity to either AB1 or AB2, but have decreased or no affinity for the other protein. Addition of such a destabilizing compound to a preformed AB1/AB2/small molecule complex is expected to disrupt the complex by competing for binding to either AB1 or AB2. To screen for such compounds, the two hybrid assay can be employed using a destabilized fluorescent protein as a Gal4 reporter. Cells with the short half-life fluorescent protein Gal4 reporter and expressing AB1 and AB2 can be incubated in the selected small molecule at a set concentration for 1-2 days. Subsequently a second test compound can be added at an equal or greater concentration and the cells can be analyzed by flow cytometry at 2-3 hour intervals. Compounds which disrupt the AB1/AB2/small molecule complex will decrease transcription of the Gal4 reporter resulting in decreased cell fluorescence over time.

Step 19. AB1/AB2 protein pairs can be used to make small molecule inducible cellular control systems.

Numerous proteins, encoding sequences, and vectors are referenced herein. Particular supporting sequences can be obtained from publicly available databases well known to those of ordinary skill in the art. Reference to numerical steps does not require that each step be carried out or that necessarily be practiced in the stated order in every embodiment disclosed herein. Rather, the numbered steps are provided for convenience and reference.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically-significant reduction in ability to induce gene expression in a cell using a CID system created according to the methods disclosed herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of ordinary skill in the art, such as the Oxford Dictionary of Biochemistry and Molecular Biology (Ed. Anthony Smith, Oxford University Press, Oxford, 2004).

REFERENCES

1. Bruter et al., Molekuliarnaia biologiia. 2013; 47(3): 363-87. PubMed PMID: 23888768.
2. Naidoo et al., Neurology research international. 2012; 2012:595410.

3. Gossen et al., PNAS. 1992; 89(12):5547-51.
4. Gossen et al., Science. 1995; 268(5218):1766-9. PubMed PMID: 7792603.
5. Le et al., PloS one. 2014; 9(9):e102538.
6. Favre et al., Journal of virology. 2002; 76(22):11605-11.
7. Toromanoff et al., Molecular therapy: the journal of the American Society of Gene Therapy. 2010; 18(1):151-60.
8. Mullick et al., BMC biotechnology. 2006; 6:43.
9. Fussenegger et al., Nature biotechnology. 2000; 18(11):1203-8.
10. Weber et al., Nature biotechnology. 2002; 20(9):901-7.
11. Brown et al., Cell. 1987; 49(5):603-12.
12. Braselmann et al., PNAS. 1993; 90(5):1657-61.
13. Burcin et al., Frontiers in bioscience: a journal and virtual library. 1998; 3:c1-7.
14. Gallinari et al., Chemistry & biology. 2005; 12(8):883-93.
15. Nordstrom, Steroids. 2003; 68(10-13):1085-94.
16. No et al., PNAS. 1996; 93(8):3346-51.
17. Suhr et al., PNAS. 1998; 95(14):7999-8004. PubMed PMID: 9653129;
18. Palli et al., European journal of biochemistry/FEBS. 2003; 270(6):1308-15.
19. Komita et al., Cancer gene therapy. 2009; 16(12):883-91.
20. DeRose et al., Pflugers Archiv: European journal of physiology. 2013; 465(3):409-17.
21. Rivera et al., Nature medicine. 1996; 2(9):1028-32.
22. Choi et al., Science. 1996; 273(5272):239-42.
23. Clemons et al., Chemistry & biology. 2002; 9(1):49-61.
24. Pollock et al., PNAS. 2000; 97(24):13221-6.
25. Magari et al., The Journal of clinical investigation. 1997; 100(11):2865-72.
26. Banaszynski et al., Journal of the American Chemical Society. 2005; 127(13):4715-21.
27. Liu et al., Angewandte Chemie. 2014; 53(38):10049-55.
28. Spencer et al., Science. 1993; 262(5136):1019-24.
29. Clackson et al., PNAS. 1998; 95(18):10437-42.
30. Nor et al., Gene therapy. 2002; 9(7):444-51.
31. Straathof et al., Blood. 2005; 105(11):4247-54.
32. Thomis et al., Blood. 2001; 97(5):1249-57. PubMed PMID: 11222367.
33. Di Stasi et al., The New England journal of medicine. 2011; 365(18):1673-83.
34. Liu et al., Journal of biosciences. 2014; 39(1):85-95.
35. Van Acker et al., Journal of cell science. 2004; 117(Pt 7):1129-37.
36. Voss et al., Molecular immunology. 1989; 26(10):971-7.
37. Weidner et al., The Journal of biological chemistry. 1992; 267(15):10281-8.
38. Hwang & Foote, et al., Methods. 2005; 36(1):3-10.
39. Tsurushita et al., Methods. 2005; 36(1):69-83.
40. Safdari et al., Biotechnology & genetic engineering reviews. 2013; 29:175-86.
41. Wesolowski et al., Medical microbiology and immunology. 2009; 198(3):157-74.
42. Yang & RadeR, et al., Methods in molecular biology. 2012; 901:209-32.
43. Toleikis & Frenzel, Methods in molecular biology. 2012; 907:59-71.
44. Hermanson, Bioconjugate techniques. Third edition. ed. xvii, 1146 pages p.
45. Niemeyer, Bioconjugation protocols: strategies and methods. 2nd ed. Totowa, N.J.: Humana Press; 2011. xvi, 605 p. p.
46. Pastor-Navarro et al., Analytica chimica acta. 2007; 594(2):211-8.
47. Mata, Current pharmaceutical design. 1999; 5(11):955-64.
48. Greenfield, Antibodies: a laboratory manual. Second edition. ed. xxi, 847 pages p.
49. Bruggemann et al., Archivum immunologiae et therapiae experimentalis. 2015; 63(2):101-8.
50. Proetzel & Ebersbach, Antibody methods and protocols. New York: Humana Press; 2012. x, 325 p. p.
51. Leenaars et al., ILAR journal/National Research Council, Institute of Laboratory Animal Resources. 2005; 46(3):269-79.
52. Animal Care and Use Committee. Guidelines for the Use of Adjuvants in Research. Intramural Animal Care and Use (ACU) program of the National Institutes of Health (NIH). 2013.
53. Pardon et al., Nature protocols. 2014; 9(3):674-93.
54. Hornbeck, Current protocols in immunology/edited by John E Coligan [et al]. 2001; Chapter 2:Unit 2 1.
55. Coligan, Current protocols in immunology. New York: John Wiley and Sons. p. v. (loose leaf).
56. Green et al., Molecular cloning: a laboratory manual. 4th ed. Cold Spring Harbor, N.Y.: Cold Spring Harbor Laboratory Press; 2012.
57. Andris-Widhopf et al., 3rd. Generation of human scFv antibody libraries: PCR amplification and assembly of light- and heavy-chain coding sequences. Cold Spring Harbor protocols. 2011; 2011(9).
58. Little et al., Journal of immunological methods. 1999; 231(1-2):3-9.
59. Pansri et al., BMC biotechnology. 2009; 9:6.
60. Casini et al., Nature reviews Molecular cell biology. 2015.
61. Hanahan et al., Methods in enzymology. 1991; 204:63-113.
62. Elsaesser & Paysan, BioTechniques. 2004; 37(2):200, 2.
63. Miyazaki et al., Gene. 1989; 79(2):269-77.
64. Ding et al., Cell. 2005; 122(3):473-83.
65. Benatuil et al., Protein engineering, design & selection: PEDS. 2010; 23(4):155-9.
66. Gietz & Schiestl, Nature protocols. 2007; 2(1):38-41.
67. Balzi & Goffeau, Journal of bioenergetics and biomembranes. 1995; 27(1):71-6.
68. Kontermann & Dübel, Antibody engineering. 2nd ed. Heidelburg: Springer; 2010.
69. Visintin et al., Journal of molecular biology. 2002; 317(1):73-83.
70. Ewert et al., Methods. 2004; 34(2):184-99.
71. Philibert et al., BMC biotechnology. 2007; 7:81.
72. Hulme & Trevethick, British journal of pharmacology. 2010; 161(6):1219-37.
73. Vincke et al., The Journal of biological chemistry. 2009; 284(5):3273-84.
74. Kuramochi et al., Methods in molecular biology. 2014; 1060:123-37.
75. Olimpieri et al., Bioinformatics. 2015; 31(3):434-5.
76. Kim et al., Methods in molecular biology. 2014; 1131:407-20.
77. Kay et al., Methods in molecular biology. 2009; 498:185-96.

78. Mol & Fischer, Surface plasmon resonance: methods and protocols. New York: Humana Press; 2010. x, 286 p. p.
79. Merck & Co. The Merck veterinary manual. Rahway, N.J. Whitehouse Station, N.J.: Merck and Co. Merck & Co; 1955. p. v.
80. Plumb D C. Plumb's veterinary drug handbook. Eighth edition. ed. 11 unnumbered pages, 1279 pages p.
81. Stynen et al., Microbiology and molecular biology reviews: MMBR. 2012; 76(2):331-82.
82. Balciunas et al., PLoS genetics. 2006; 2(11):e169.
83. Mates et al., Nature genetics. 2009; 41(6):753-61.
84. Vidal et al., PNAS. 1996; 93(19):10315-20. PubMed PMID: 8816797.
85. Gietz & Schiestl, Nature protocols. 2007; 2(1):31-4.
86. Boeke et al., Methods in enzymology. 1987; 154:164-75.
87. Mockli & Auerbach, BioTechniques. 2004; 36(5):872-6.
88. Bartel & Fields, The yeast two-hybrid system. New York: Oxford University Press; 1997. xi, 344 p. p.

What is claimed is:

1. A method of regulating cellular events within a cell, comprising:
   administering a cell-permeable small molecule to the cell, wherein the cell has internalized genetic constructs encoding:
   a first fusion protein comprising an antibody binding domain (AB1) and a first effector molecule, wherein AB1 binds the small molecule to form an AB1/small molecule complex, and
   a second fusion protein comprising a metatype antibody binding domain (AB2) and a second effector molecule, wherein AB2 binds a portion of AB1 and a portion of the small molecule, but only when AB1 is bound to the small molecule to form an AB1/small molecule complex;
   wherein upon the administering of the cell-permeable small molecule, the first fusion protein and the second fusion protein dimerize to regulate cellular events within the cell.

2. The method of claim 1, wherein the AB1 and/or AB2 are heavy chain only (VHH) or a single chain variable fragment (scFV) of an antibody.

3. The method of claim 2, wherein the scFV consists essentially of a variable heavy chain linked to a variable light chain.

4. The method of claim 1, wherein AB1 binds to the small molecule with high affinity.

5. The method of claim 1, wherein AB2 and/or AB1 are obtained by immunization of a target animal with the small molecule.

6. The method of claim 1, wherein AB2 and/or AB1 is humanized.

7. The method of claim 1, wherein binding affinity between AB1 and the small molecule is optimized.

8. The method of claim 1, wherein binding affinity between AB2 and the AB1/small molecule complex is optimized.

9. The method of claim 1, wherein in vivo half-life of AB2 and/or AB1 is optimized.

10. The method of claim 1, wherein the first or second effector molecule is a DNA binding domain, a transcription activation domain, a transcription repressor domain, an intracellular portion of a receptor, an intracellular receptor, a caspase, a kinase, an enzyme, or a protease.

11. The method of claim 1, wherein the cellular events comprise gene expression, receptor signaling, intracellular signaling, cell migration, or cell death.

12. The method of claim 1, wherein the cell is in vitro or in vivo.

13. The method of claim 1, wherein the cell permeable small molecule is an antibiotic.

14. The method of claim 1, wherein the genetic constructs were internalized by transfection, electroporation, or transformation.

15. The method of claim 1, wherein the cell is a mammalian cell or a yeast cell.

16. The method of claim 1, wherein the first effector molecule is a DNA binding protein and the second effector molecule is a transcriptional activator, or wherein the first effector molecule is a transcriptional activator and the second effector molecule is a DNA binding protein.

17. The method of claim 1, wherein the first effector molecule and the second effector molecule are cellular receptors.

18. The method of claim 1, wherein the first effector molecule and the second effector molecule are initiator caspases.

* * * * *

SEQUENCE LISTING

```
<160> NUMBER OF SEQ ID NOS: 117

<210> SEQ ID NO 1
<211> LENGTH: 74
<212> TYPE: DNA
<213> ORGANISM: Artificial sequence
<220> FEATURE:
<223> OTHER INFORMATION: Mammalian screening vector sequence

<400> SEQUENCE: 1
tcattttggc aaagaattac ttaatacgac tcactatagg ctcgagaagg ccattacggc    60
cttagatcta atct                                                      74

<210> SEQ ID NO 2
<211> LENGTH: 74
<212> TYPE: DNA
<213> ORGANISM: Artificial sequence
<220> FEATURE:
<223> OTHER INFORMATION: Mammalian screening vector sequence

<400> SEQUENCE: 2
agagcggccg cgctagcaca ggtcaccgtg tcgacaggcg gatcggtgag caagggcgag    60
gaggtgatca agga                                                      74

<210> SEQ ID NO 3
<211> LENGTH: 24
<212> TYPE: PRT
<213> ORGANISM: Artificial sequence
<220> FEATURE:
<223> OTHER INFORMATION: Mammalian screening vector sequence

<400> SEQUENCE: 3

Ala Ala Ala Leu Ala Gln Val Thr Val Ser Thr Gly Gly Ser Val Ser
1               5                   10                  15

Lys Gly Glu Glu Val Ile Lys Glu
            20

<210> SEQ ID NO 4
<211> LENGTH: 58
<212> TYPE: DNA
<213> ORGANISM: Artificial sequence
<220> FEATURE:
<223> OTHER INFORMATION: Yeast screening vector sequence

<400> SEQUENCE: 4
taaaacacca gaacttagtt tcgactcgag aaggccatta cggccttaga tctaatct     58

<210> SEQ ID NO 5
<211> LENGTH: 74
<212> TYPE: DNA
<213> ORGANISM: Artificial sequence
<220> FEATURE:
<223> OTHER INFORMATION: Yeast screening vector sequence
```

<400> SEQUENCE: 5
agagcggccg cgctagcaca ggtcaccgtg tcgacaggcg atcggtgag caagggcgag   60 gaggtgatca agga   74

<210> SEQ ID NO 6
<211> LENGTH: 24
<212> TYPE: PRT
<213> ORGANISM: Artificial sequence
<220> FEATURE:
<223> OTHER INFORMATION: Yeast screening vector sequence

<400> SEQUENCE: 6

Ala Ala Ala Leu Ala Gln Val Thr Val Ser Thr Gly Gly Ser Val Ser
1               5                   10                  15

Lys Gly Glu Glu Val Ile Lys Glu
            20

<210> SEQ ID NO 7
<211> LENGTH: 75
<212> TYPE: DNA
<213> ORGANISM: Artificial sequence
<220> FEATURE:
<223> OTHER INFORMATION: Bacterial expression vector sequence

<400> SEQUENCE: 7
taatacgact cactataggg gaattgtgag cggataacaa ttcccctcta gaaataattt   60
tgtttaactt taaga   75

<210> SEQ ID NO 8
<211> LENGTH: 73
<212> TYPE: DNA
<213> ORGANISM: Artificial sequence
<220> FEATURE:
<223> OTHER INFORMATION: Bacterial expression vector sequence

<400> SEQUENCE: 8
aggagatata catatgaaat acctgctgcc gaccgctgct gctggtctgc tgctcctcgc   60
tgcccagccg gcg   73

<210> SEQ ID NO 9
<211> LENGTH: 72
<212> TYPE: DNA
<213> ORGANISM: Artificial sequence
<220> FEATURE:
<223> OTHER INFORMATION: Bacterial expression vector sequence

<400> SEQUENCE: 9
atggccatgg cggccgcgct agcacaggtc accgtgtcga caggcggatc gctcgagggc   60
ctgaacgata tt   72

<210> SEQ ID NO 10
<211> LENGTH: 54
<212> TYPE: DNA
<213> ORGANISM: Artificial sequence
<220> FEATURE:
<223> OTHER INFORMATION: Bacterial expression vector sequence

<400> SEQUENCE: 10
tttgaagccc agaaaattga atggcatgaa caccaccacc accaccactg agat   54

<210> SEQ ID NO 11

```
<211> LENGTH: 20
<212> TYPE: PRT
<213> ORGANISM: Artificial sequence
<220> FEATURE:
<223> OTHER INFORMATION: Bacterial expression vector sequence

<400> SEQUENCE: 11

Met Lys Tyr Leu Leu Pro Thr Ala Ala Ala Gly Leu Leu Leu Leu Ala
1               5                   10                  15

Ala Gln Pro Ala
            20

<210> SEQ ID NO 12
<211> LENGTH: 24
<212> TYPE: PRT
<213> ORGANISM: Artificial sequence
<220> FEATURE:
<223> OTHER INFORMATION: Bacterial expression vector sequence

<400> SEQUENCE: 12

Met Ala Met Ala Ala Ala Leu Ala Gln Val Thr Val Ser Thr Gly Gly
1               5                   10                  15

Ser Leu Glu Gly Leu Asn Asp Ile
            20

<210> SEQ ID NO 13
<211> LENGTH: 16
<212> TYPE: PRT
<213> ORGANISM: Artificial sequence
<220> FEATURE:
<223> OTHER INFORMATION: Bacterial expression vector sequence

<400> SEQUENCE: 13

Phe Glu Ala Gln Lys Ile Glu Trp His Glu His His His His His
1               5                   10                  15

<210> SEQ ID NO 14
<211> LENGTH: 30
<212> TYPE: DNA
<213> ORGANISM: Artificial sequence
<220> FEATURE:
<223> OTHER INFORMATION: Mammalian Gal4 DBD vector sequence

<400> SEQUENCE: 14
aagggccagc ggcagctgac cgtgggtgga                                      30

<210> SEQ ID NO 15
<211> LENGTH: 10
<212> TYPE: PRT
<213> ORGANISM: Artificial sequence
<220> FEATURE:
<223> OTHER INFORMATION: Mammalian Gal4 DBD vector sequence

<400> SEQUENCE: 15

Lys Gly Gln Arg Gln Leu Thr Val Gly Gly
1               5                   10

<210> SEQ ID NO 16
<211> LENGTH: 75
<212> TYPE: DNA
<213> ORGANISM: Artificial sequence
<220> FEATURE:
<223> OTHER INFORMATION: Mammalian Gal4 DBD vector sequence

<400> SEQUENCE: 16
agcggcagtg cggccgcgct agcacaggtc accgtgtcga caggcggatc gggtgaaggc    60
```
agaggctctc tcctc								75

<210> SEQ ID NO 17
<211> LENGTH: 25
<212> TYPE: PRT
<213> ORGANISM: Artificial sequence
<220> FEATURE:
<223> OTHER INFORMATION: Mammalian Gal4 DBD vector sequence

<400> SEQUENCE: 17

Ser Gly Ser Ala Ala Ala Leu Ala Gln Val Thr Val Ser Thr Gly Gly
1               5                   10                  15

Ser Gly Glu Gly Arg Gly Ser Leu Leu
            20                  25

<210> SEQ ID NO 18
<211> LENGTH: 60
<212> TYPE: DNA
<213> ORGANISM: Artificial sequence
<220> FEATURE:
<223> OTHER INFORMATION: Yeast Gal4 DBD vector sequence

<400> SEQUENCE: 18
agacagttga ctgtatcgcc ggaatttgta atacgactca ctatagggcg agccgccatc		60

<210> SEQ ID NO 19
<211> LENGTH: 20
<212> TYPE: PRT
<213> ORGANISM: Artificial sequence
<220> FEATURE:
<223> OTHER INFORMATION: Yeast Gal4 DBD vector sequence

<400> SEQUENCE: 19

Arg Gln Leu Thr Val Ser Pro Glu Phe Val Ile Arg Leu Thr Ile Gly
1               5                   10                  15

Arg Ala Ala Ile
            20

<210> SEQ ID NO 20
<211> LENGTH: 79
<212> TYPE: DNA
<213> ORGANISM: Artificial sequence
<220> FEATURE:
<223> OTHER INFORMATION: Yeast Gal4 DBD vector sequence

<400> SEQUENCE: 20
atggaggagc agaagctgat ctcagaggag gacctggcgg ccgcgctagc acaggtcacc		60 gtgtcgacat gagatgggc								79

<210> SEQ ID NO 21
<211> LENGTH: 23
<212> TYPE: PRT
<213> ORGANISM: Artificial sequence
<220> FEATURE:
<223> OTHER INFORMATION: Yeast Gal4 DBD vector sequence

<400> SEQUENCE: 21

Met Glu Glu Gln Lys Leu Ile Ser Glu Glu Asp Leu Ala Ala Ala Leu
1               5                   10                  15

Ala Gln Val Thr Val Ser Thr
            20

<210> SEQ ID NO 22

-continued

```
<211> LENGTH: 55
<212> TYPE: DNA
<213> ORGANISM: Artificial sequence
<220> FEATURE:
<223> OTHER INFORMATION: Mammalian activation domain vector sequence

<400> SEQUENCE: 22
ttagatctaa tctagagcgg ccgcgctagc acaggtcacc gtgtcgacag gcgga       55

<210> SEQ ID NO 23
<211> LENGTH: 13
<212> TYPE: PRT
<213> ORGANISM: Artificial sequence
<220> FEATURE:
<223> OTHER INFORMATION: Mammalian activation domain vector sequence

<400> SEQUENCE: 23

Ala Ala Ala Leu Ala Gln Val Thr Val Ser Thr Gly Gly
1               5                   10

<210> SEQ ID NO 24
<211> LENGTH: 60
<212> TYPE: DNA
<213> ORGANISM: Artificial sequence
<220> FEATURE:
<223> OTHER INFORMATION: Mammalian activation domain vector sequence

<400> SEQUENCE: 24
tcgggaggta gtccaaaaaa gaagagaaag gtaggaacgc cgatggagtt ccagtacctg    60

<210> SEQ ID NO 25
<211> LENGTH: 20
<212> TYPE: PRT
<213> ORGANISM: Artificial sequence
<220> FEATURE:
<223> OTHER INFORMATION: Mammalian activation domain vector sequence

<400> SEQUENCE: 25

Ser Gly Gly Ser Pro Lys Lys Lys Arg Lys Val Gly Thr Pro Met Glu
1               5                   10                  15

Phe Gln Tyr Leu
            20

<210> SEQ ID NO 26
<211> LENGTH: 67
<212> TYPE: DNA
<213> ORGANISM: Artificial sequence
<220> FEATURE:
<223> OTHER INFORMATION: Yeast activation domain vector sequence

<400> SEQUENCE: 26 agataccccca ccaaacccaa aaaagagat ctttaatacg actcactata gggcgagcgc    60
cgccatg                                                              67

<210> SEQ ID NO 27
<211> LENGTH: 22
<212> TYPE: PRT
<213> ORGANISM: Artificial sequence
<220> FEATURE:
<223> OTHER INFORMATION: Yeast activation domain vector sequence

<400> SEQUENCE: 27

Asp Thr Pro Pro Asn Pro Lys Lys Glu Ile Phe Asn Thr Thr His Tyr
1               5                   10                  15

Arg Ala Ser Ala Ala Met
```

<210> SEQ ID NO 28
<211> LENGTH: 71
<212> TYPE: DNA
<213> ORGANISM: Artificial sequence
<220> FEATURE:
<223> OTHER INFORMATION: Yeast activation domain vector sequence

<400> SEQUENCE: 28
gagtacccat acgacgtacc agattacgct gcggccgcgc tagcacaggt caccgtgtcg    60
acatgaatac t                                                        71

<210> SEQ ID NO 29
<211> LENGTH: 21
<212> TYPE: PRT
<213> ORGANISM: Artificial sequence
<220> FEATURE:
<223> OTHER INFORMATION: Yeast activation domain vector sequence

<400> SEQUENCE: 29

Glu Tyr Pro Tyr Asp Val Pro Asp Tyr Ala Ala Ala Ala Leu Ala Gln
1               5                   10                  15

Val Thr Val Ser Thr
            20

<210> SEQ ID NO 30
<211> LENGTH: 23
<212> TYPE: DNA
<213> ORGANISM: Artificial sequence
<220> FEATURE:
<223> OTHER INFORMATION: Camel/llama VHH primer for

<400> SEQUENCE: 30
gtcctggctg ctcttctaca agg                                           23

<210> SEQ ID NO 31
<211> LENGTH: 23
<212> TYPE: DNA
<213> ORGANISM: Artificial sequence
<220> FEATURE:
<223> OTHER INFORMATION: Camel/llama VHH primer rev

<400> SEQUENCE: 31
ggtacgtgct gttgaactgt tcc                                           23

<210> SEQ ID NO 32
<211> LENGTH: 53
<212> TYPE: DNA
<213> ORGANISM: Artificial sequence
<220> FEATURE:
<223> OTHER INFORMATION: Camel/llama VHH primer for
<220> FEATURE:
<221> NAME/KEY: misc_feature
<222> LOCATION: (1)..(9)
<223> OTHER INFORMATION: n is a, c, g, or t

<400> SEQUENCE: 32
nnnnnnnnng cggccgccac catggatgtg cagctgcagg agtctggrgg agg          53

<210> SEQ ID NO 33
<211> LENGTH: 50
<212> TYPE: DNA
<213> ORGANISM: Artificial sequence
<220> FEATURE:
<223> OTHER INFORMATION: Camel/llama VHH primer for
<220> FEATURE:
<221> NAME/KEY: misc_feature
<222> LOCATION: (1)..(9)
<223> OTHER INFORMATION: n is a, c, g, or t

<400> SEQUENCE: 33
nnnnnnnnng cggccgccac catggctsak gtgcagctgg tggagtctgg    50

<210> SEQ ID NO 34
<211> LENGTH: 29
<212> TYPE: DNA
<213> ORGANISM: Artificial sequence
<220> FEATURE:
<223> OTHER INFORMATION: Camel/llama VHH primer rev
<220> FEATURE:
<221> NAME/KEY: misc_feature
<222> LOCATION: (1)..(9)
<223> OTHER INFORMATION: n is a, c, g, or t

<400> SEQUENCE: 34
nnnnnnnnnc tggagacggt gacctgggt    29

<210> SEQ ID NO 35
<211> LENGTH: 15
<212> TYPE: DNA
<213> ORGANISM: Artificial sequence
<220> FEATURE:
<223> OTHER INFORMATION: Alpaca VHH primer for

<400> SEQUENCE: 35
ggtggtcctg gctgc    15

<210> SEQ ID NO 36
<211> LENGTH: 30
<212> TYPE: DNA
<213> ORGANISM: Artificial sequence
<220> FEATURE:
<223> OTHER INFORMATION: Alpaca VHH primer rev

<400> SEQUENCE: 36
gatcactagt ggggtcttcg ctgtggtgcg    30

<210> SEQ ID NO 37
<211> LENGTH: 53
<212> TYPE: DNA
<213> ORGANISM: Artificial sequence
<220> FEATURE:
<223> OTHER INFORMATION: Alpaca VHH primer for
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 37
nnnnnnnnng cggccgccac catggctcag ktgcagctcg tggagtcngg ngg    53

<210> SEQ ID NO 38
<211> LENGTH: 29
<212> TYPE: DNA
<213> ORGANISM: Artificial sequence
<220> FEATURE:

```
<223> OTHER INFORMATION: Alpaca VHH primer rev
<220> FEATURE:
<221> NAME/KEY: misc_feature
<222> LOCATION: (1)..(9)
<223> OTHER INFORMATION: n is a, c, g, or t

<400> SEQUENCE: 38
nnnnnnnnnc tggagacggt gacctgggt                                           29

<210> SEQ ID NO 39
<211> LENGTH: 21
<212> TYPE: DNA
<213> ORGANISM: Artificial sequence
<220> FEATURE:
<223> OTHER INFORMATION: CAG promoter For primer

<400> SEQUENCE: 39
ctacagctcc tgggcaacgt g                                                   21

<210> SEQ ID NO 40
<211> LENGTH: 25
<212> TYPE: DNA
<213> ORGANISM: Artificial sequence
<220> FEATURE:
<223> OTHER INFORMATION: TdTomato Rev primer

<400> SEQUENCE: 40
tgatcacctc ctcgcccttg ctcac                                               25

<210> SEQ ID NO 41
<211> LENGTH: 24
<212> TYPE: DNA
<213> ORGANISM: Artificial sequence
<220> FEATURE:
<223> OTHER INFORMATION: TDH3 promoter For primer

<400> SEQUENCE: 41
acaccagaac ttagtttcga ctcg                                                24

<210> SEQ ID NO 42
<211> LENGTH: 22
<212> TYPE: DNA
<213> ORGANISM: Artificial sequence
<220> FEATURE:
<223> OTHER INFORMATION: p65 AD Rev primer

<400> SEQUENCE: 42
ggcaggtact ggaactccat cg                                                  22

<210> SEQ ID NO 43
<211> LENGTH: 19
<212> TYPE: DNA
<213> ORGANISM: Artificial sequence
<220> FEATURE:
<223> OTHER INFORMATION: T7 promoter primer

<400> SEQUENCE: 43
taatacgact cactatagg                                                      19

<210> SEQ ID NO 44
<211> LENGTH: 21
<212> TYPE: DNA
<213> ORGANISM: Artificial sequence
<220> FEATURE:
<223> OTHER INFORMATION: Reverse sequencing primer

<400> SEQUENCE: 44
```

-continued

```
gtggtggtgt tcatgccatt c                                          21

<210> SEQ ID NO 45
<211> LENGTH: 77
<212> TYPE: DNA
<213> ORGANISM: Artificial sequence
<220> FEATURE:
<223> OTHER INFORMATION: VH, 5' sense, long linker primer

<400> SEQUENCE: 45
ggtggttcct ctagatcttc ctcctctggt ggcggtggct cgggcggtgg tgggcaggtg    60
cagctggtgc agtctgg                                                   77

<210> SEQ ID NO 46
<211> LENGTH: 77
<212> TYPE: DNA
<213> ORGANISM: Artificial sequence
<220> FEATURE:
<223> OTHER INFORMATION: VH, 5' sense, long linker primer

<400> SEQUENCE: 46
ggtggttcct ctagatcttc ctcctctggt ggcggtggct cgggcggtgg tgggcagatc    60
accttgaagg agtctgg                                                   77

<210> SEQ ID NO 47
<211> LENGTH: 77
<212> TYPE: DNA
<213> ORGANISM: Artificial sequence
<220> FEATURE:
<223> OTHER INFORMATION: VH, 5' sense, long linker primer

<400> SEQUENCE: 47
ggtggttcct ctagatcttc ctcctctggt ggcggtggct cgggcggtgg tggggaggtg    60
cagctggtgs agtctgg                                                   77

<210> SEQ ID NO 48
<211> LENGTH: 76
<212> TYPE: DNA
<213> ORGANISM: Artificial sequence
<220> FEATURE:
<223> OTHER INFORMATION: VH, 5' sense, long linker primer

<400> SEQUENCE: 48
ggtggttcct ctagatcttc ctcctctggt ggcggtggct cgggcggtgg tggggaggtg    60
cagctgktgg agtctg                                                    76

<210> SEQ ID NO 49
<211> LENGTH: 77
<212> TYPE: DNA
<213> ORGANISM: Artificial sequence
<220> FEATURE:
<223> OTHER INFORMATION: VH, 5' sense, long linker primer

<400> SEQUENCE: 49
ggtggttcct ctagatcttc ctcctctggt ggcggtggct cgggcggtgg tgggcaggtg    60
cagctgcagg agtcggg                                                   77

<210> SEQ ID NO 50
<211> LENGTH: 77
<212> TYPE: DNA
<213> ORGANISM: Artificial sequence
<220> FEATURE:
```

<223> OTHER INFORMATION: VH, 3' reverse long linker primer

<400> SEQUENCE: 50
ggtggttcct ctagatcttc ctcctctggt ggcggtggct cgggcggtgg tgggcaggtg    60
cagctacagc agtgggg    77

<210> SEQ ID NO 51
<211> LENGTH: 43
<212> TYPE: DNA
<213> ORGANISM: Artificial sequence
<220> FEATURE:
<223> OTHER INFORMATION: VH, 3' reverse long linker primer

<400> SEQUENCE: 51
gccactagtg agtcgacacg accgatgggc ccttggtgga rgc    43

<210> SEQ ID NO 52
<211> LENGTH: 43
<212> TYPE: DNA
<213> ORGANISM: Artificial sequence
<220> FEATURE:
<223> OTHER INFORMATION: VH, 3' reverse long linker primer

<400> SEQUENCE: 52
gccactagtg agtcgacaca agggttgggg cggatgcact ccc    43

<210> SEQ ID NO 53
<211> LENGTH: 43
<212> TYPE: DNA
<213> ORGANISM: Artificial sequence
<220> FEATURE:
<223> OTHER INFORMATION: VH, 3' reverse long linker primer

<400> SEQUENCE: 53
gccactagtg agtcgacacg accttggggc tggtcgggga tgc    43

<210> SEQ ID NO 54
<211> LENGTH: 43
<212> TYPE: DNA
<213> ORGANISM: Artificial sequence
<220> FEATURE:
<223> OTHER INFORMATION: VH, 3' reverse long linker primer

<400> SEQUENCE: 54
gccactagtg agtcgacacc acatccggag ccttggtggg tgc    43

<210> SEQ ID NO 55
<211> LENGTH: 43
<212> TYPE: DNA
<213> ORGANISM: Artificial sequence
<220> FEATURE:
<223> OTHER INFORMATION: VH, 3' reverse long linker primer

<400> SEQUENCE: 55
gccactagtg agtcgacacg acggatgggc tctgtgtgga ggc    43

<210> SEQ ID NO 56
<211> LENGTH: 37
<212> TYPE: DNA
<213> ORGANISM: Artificial sequence
<220> FEATURE:
<223> OTHER INFORMATION: Vkappa, 5' sense long linker primer

<400> SEQUENCE: 56
aagcggccgc caccatggtg cagatgaccc agtctcc    37

<210> SEQ ID NO 57
<211> LENGTH: 37
<212> TYPE: DNA
<213> ORGANISM: Artificial sequence
<220> FEATURE:
<223> OTHER INFORMATION: Vkappa, 5' sense long linker primer

<400> SEQUENCE: 57
aagcggccgc caccatggtg gtgatgacyc agtctcc                     37

<210> SEQ ID NO 58
<211> LENGTH: 37
<212> TYPE: DNA
<213> ORGANISM: Artificial sequence
<220> FEATURE:
<223> OTHER INFORMATION: Vkappa, 5' sense long linker primer

<400> SEQUENCE: 58
aagcggccgc caccatggtg gtgwtgacrc agtctcc                     37

<210> SEQ ID NO 59
<211> LENGTH: 37
<212> TYPE: DNA
<213> ORGANISM: Artificial sequence
<220> FEATURE:
<223> OTHER INFORMATION: Vkappa, 5' sense long linker primer

<400> SEQUENCE: 59
aagcggccgc caccatggtg acactcacgc agtctcc                     37

<210> SEQ ID NO 60
<211> LENGTH: 42
<212> TYPE: DNA
<213> ORGANISM: Artificial sequence
<220> FEATURE:
<223> OTHER INFORMATION: Vkappa, 3' reverse, long linker primer

<400> SEQUENCE: 60
ggaagatcta gaggaaccac ctttgatytc caccttggtc cc               42

<210> SEQ ID NO 61
<211> LENGTH: 42
<212> TYPE: DNA
<213> ORGANISM: Artificial sequence
<220> FEATURE:
<223> OTHER INFORMATION: Vkappa, 3' reverse, long linker primer

<400> SEQUENCE: 61
ggaagatcta gaggaaccac ctttgatctc cagcttggtc cc               42

<210> SEQ ID NO 62
<211> LENGTH: 42
<212> TYPE: DNA
<213> ORGANISM: Artificial sequence
<220> FEATURE:
<223> OTHER INFORMATION: Vkappa, 3' reverse, long linker primer

<400> SEQUENCE: 62
ggaagatcta gaggaaccac ctttgatatc cactttggtc cc               42

<210> SEQ ID NO 63
<211> LENGTH: 42
<212> TYPE: DNA
<213> ORGANISM: Artificial sequence
<220> FEATURE:

<223> OTHER INFORMATION: Vkappa, 3' reverse, long linker primer

<400> SEQUENCE: 63
ggaagatcta gaggaaccac ctttaatctc cagtcgtgtc cc                    42

<210> SEQ ID NO 64
<211> LENGTH: 40
<212> TYPE: DNA
<213> ORGANISM: Artificial sequence
<220> FEATURE:
<223> OTHER INFORMATION: Vlambda, 5' sense, long linker primer

<400> SEQUENCE: 64
aagcggccgc caccatggtg gtgbtgacgc agccgccctc                       40

<210> SEQ ID NO 65
<211> LENGTH: 40
<212> TYPE: DNA
<213> ORGANISM: Artificial sequence
<220> FEATURE:
<223> OTHER INFORMATION: Vlambda, 5' sense, long linker primer

<400> SEQUENCE: 65
aagcggccgc caccatggtg gtgctgactc agccaccctc                       40

<210> SEQ ID NO 66
<211> LENGTH: 43
<212> TYPE: DNA
<213> ORGANISM: Artificial sequence
<220> FEATURE:
<223> OTHER INFORMATION: Vlambda, 5' sense, long linker primer

<400> SEQUENCE: 66
aagcggccgc caccatggtg gccctgactc agcctccctc cgt                   43

<210> SEQ ID NO 67
<211> LENGTH: 43
<212> TYPE: DNA
<213> ORGANISM: Artificial sequence
<220> FEATURE:
<223> OTHER INFORMATION: Vlambda, 5' sense, long linker primer

<400> SEQUENCE: 67
aagcggccgc caccatggtg ctgactcagc caccctcagt gtc                   43

<210> SEQ ID NO 68
<211> LENGTH: 40
<212> TYPE: DNA
<213> ORGANISM: Artificial sequence
<220> FEATURE:
<223> OTHER INFORMATION: Vlambda, 5' sense, long linker primer

<400> SEQUENCE: 68
aagcggccgc caccatggtg gtgctgactc aatcgccctc                       40

<210> SEQ ID NO 69
<211> LENGTH: 40
<212> TYPE: DNA
<213> ORGANISM: Artificial sequence
<220> FEATURE:
<223> OTHER INFORMATION: Vlambda, 5' sense, long linker primer

<400> SEQUENCE: 69
aagcggccgc caccatggtg atgctgactc agccccactc                       40

```
<210> SEQ ID NO 70
<211> LENGTH: 40
<212> TYPE: DNA
<213> ORGANISM: Artificial sequence
<220> FEATURE:
<223> OTHER INFORMATION: Vlambda, 5' sense, long linker primer

<400> SEQUENCE: 70
aagcggccgc caccatggtg gtggtgacyc aggagccmtc                              40

<210> SEQ ID NO 71
<211> LENGTH: 40
<212> TYPE: DNA
<213> ORGANISM: Artificial sequence
<220> FEATURE:
<223> OTHER INFORMATION: Vlambda, 5' sense, long linker primer

<400> SEQUENCE: 71
aagcggccgc caccatggtg gtgctgactc agccaccttc                              40

<210> SEQ ID NO 72
<211> LENGTH: 40
<212> TYPE: DNA
<213> ORGANISM: Artificial sequence
<220> FEATURE:
<223> OTHER INFORMATION: Vlambda, 5' sense, long linker primer

<400> SEQUENCE: 72
aagcggccgc caccatggtg gggcagactc agcagctctc                              40

<210> SEQ ID NO 73
<211> LENGTH: 45
<212> TYPE: DNA
<213> ORGANISM: Artificial sequence
<220> FEATURE:
<223> OTHER INFORMATION: Vlambda, 3' reverse, long linker primer

<400> SEQUENCE: 73
ggaagatcta gaggaaccac cgcctaggac ggtcascttg gtscc                        45

<210> SEQ ID NO 74
<211> LENGTH: 45
<212> TYPE: DNA
<213> ORGANISM: Artificial sequence
<220> FEATURE:
<223> OTHER INFORMATION: Vlambda, 3' reverse, long linker primer

<400> SEQUENCE: 74
ggaagatcta gaggaaccac cgcctaaaat gatcagctgg gttcc                        45

<210> SEQ ID NO 75
<211> LENGTH: 45
<212> TYPE: DNA
<213> ORGANISM: Artificial sequence
<220> FEATURE:
<223> OTHER INFORMATION: Vlambda, 3' reverse, long linker primer

<400> SEQUENCE: 75
ggaagatcta gaggaaccac cgccgaggac ggtcagctsg gtscc                        45

<210> SEQ ID NO 76
<211> LENGTH: 29
<212> TYPE: DNA
<213> ORGANISM: Artificial sequence
<220> FEATURE:
<223> OTHER INFORMATION: Overlap extension RSC-F for primer
<220> FEATURE:
```

```
<221> NAME/KEY: misc_feature
<222> LOCATION: (1)..(9)
<223> OTHER INFORMATION: n is a, c, g, or t

<400> SEQUENCE: 76
nnnnnnnnna agcggccgcc accatggtg                                     29

<210> SEQ ID NO 77
<211> LENGTH: 28
<212> TYPE: DNA
<213> ORGANISM: Artificial sequence
<220> FEATURE:
<223> OTHER INFORMATION: Overlap extension RSC-B rev primer
<220> FEATURE:
<221> NAME/KEY: misc_feature
<222> LOCATION: (1)..(9)
<223> OTHER INFORMATION: n is a, c, g, or t

<400> SEQUENCE: 77
nnnnnnnnng ccactagtga gtcgacac                                      28

<210> SEQ ID NO 78
<211> LENGTH: 26
<212> TYPE: DNA
<213> ORGANISM: Artificial sequence
<220> FEATURE:
<223> OTHER INFORMATION: VH, 1st Round For primer

<400> SEQUENCE: 78
caggtkcagc tggtgcagtc tggggc                                        26

<210> SEQ ID NO 79
<211> LENGTH: 23
<212> TYPE: DNA
<213> ORGANISM: Artificial sequence
<220> FEATURE:
<223> OTHER INFORMATION: VH, 1st Round For primer

<400> SEQUENCE: 79
caggtccagc ttgtgcagtc tgg                                           23

<210> SEQ ID NO 80
<211> LENGTH: 23
<212> TYPE: DNA
<213> ORGANISM: Artificial sequence
<220> FEATURE:
<223> OTHER INFORMATION: VH, 1st Round For primer

<400> SEQUENCE: 80
caggtccagc tggtacagtc tgg                                           23

<210> SEQ ID NO 81
<211> LENGTH: 23
<212> TYPE: DNA
<213> ORGANISM: Artificial sequence
<220> FEATURE:
<223> OTHER INFORMATION: VH, 1st Round For primer

<400> SEQUENCE: 81
caratgcagc tggtgcagtc tgg                                           23

<210> SEQ ID NO 82
<211> LENGTH: 23
<212> TYPE: DNA
<213> ORGANISM: Artificial sequence
<220> FEATURE:
<223> OTHER INFORMATION: VH, 1st Round For primer
```

```
<400> SEQUENCE: 82
gaggtccagc tggtacagtc tgg                                      23

<210> SEQ ID NO 83
<211> LENGTH: 23
<212> TYPE: DNA
<213> ORGANISM: Artificial sequence
<220> FEATURE:
<223> OTHER INFORMATION: VH, 1st Round For primer

<400> SEQUENCE: 83
cagrtcacct tgaaggagtc tgg                                      23

<210> SEQ ID NO 84
<211> LENGTH: 39
<212> TYPE: DNA
<213> ORGANISM: Artificial sequence
<220> FEATURE:
<223> OTHER INFORMATION: VH, 1st Round For primer

<400> SEQUENCE: 84
gaggtgcagc tggtggagtc tgggggaggc ttggtccag                     39

<210> SEQ ID NO 85
<211> LENGTH: 39
<212> TYPE: DNA
<213> ORGANISM: Artificial sequence
<220> FEATURE:
<223> OTHER INFORMATION: VH, 1st Round For primer

<400> SEQUENCE: 85
caggtgcagc tggtggagtc tgggggaggc ttggtcaag                     39

<210> SEQ ID NO 86
<211> LENGTH: 39
<212> TYPE: DNA
<213> ORGANISM: Artificial sequence
<220> FEATURE:
<223> OTHER INFORMATION: VH, 1st Round For primer

<400> SEQUENCE: 86
gaggtgcagc tggtggagtc tgggggaggc ttggtaaag                     39

<210> SEQ ID NO 87
<211> LENGTH: 39
<212> TYPE: DNA
<213> ORGANISM: Artificial sequence
<220> FEATURE:
<223> OTHER INFORMATION: VH, 1st Round For primer

<400> SEQUENCE: 87
gaggtgcagc tggtggagtc tgggggaggt gtggtacgg                     39

<210> SEQ ID NO 88
<211> LENGTH: 39
<212> TYPE: DNA
<213> ORGANISM: Artificial sequence
<220> FEATURE:
<223> OTHER INFORMATION: VH, 1st Round For primer

<400> SEQUENCE: 88
caggtgcagc tggtggagtc tgggggaggc gtggtccag                     39

<210> SEQ ID NO 89
```

```
<211> LENGTH: 39
<212> TYPE: DNA
<213> ORGANISM: Artificial sequence
<220> FEATURE:
<223> OTHER INFORMATION: VH, 1st Round For primer

<400> SEQUENCE: 89
gaggtgcagc tggtggagac tggaggaggc ttgatccag                         39

<210> SEQ ID NO 90
<211> LENGTH: 39
<212> TYPE: DNA
<213> ORGANISM: Artificial sequence
<220> FEATURE:
<223> OTHER INFORMATION: VH, 1st Round For primer

<400> SEQUENCE: 90
caggtgcagc tgcaggagtc gggcccagga ctggtgaag                         39

<210> SEQ ID NO 91
<211> LENGTH: 39
<212> TYPE: DNA
<213> ORGANISM: Artificial sequence
<220> FEATURE:
<223> OTHER INFORMATION: VH, 1st Round For primer

<400> SEQUENCE: 91
cagctgcagc tgcaggagtc gggcccagga ctggtgaag                         39

<210> SEQ ID NO 92
<211> LENGTH: 39
<212> TYPE: DNA
<213> ORGANISM: Artificial sequence
<220> FEATURE:
<223> OTHER INFORMATION: VH, 1st Round For primer

<400> SEQUENCE: 92
caggtgcagc tacagcagtg gggcgcagga ctgttgaag                         39

<210> SEQ ID NO 93
<211> LENGTH: 27
<212> TYPE: DNA
<213> ORGANISM: Artificial sequence
<220> FEATURE:
<223> OTHER INFORMATION: VH, 1st Round For primer

<400> SEQUENCE: 93
gaggtgcagc tggtgcagtc tggagca                                      27

<210> SEQ ID NO 94
<211> LENGTH: 27
<212> TYPE: DNA
<213> ORGANISM: Artificial sequence
<220> FEATURE:
<223> OTHER INFORMATION: VH, 1st Round For primer

<400> SEQUENCE: 94
gaagtgcagc tggtgcagtc tggagca                                      27

<210> SEQ ID NO 95
<211> LENGTH: 23
<212> TYPE: DNA
<213> ORGANISM: Artificial sequence
<220> FEATURE:
<223> OTHER INFORMATION: VH, 1st Round For primer

<400> SEQUENCE: 95
```
caggtacagc tgcagcagtc agg                                              23

<210> SEQ ID NO 96
<211> LENGTH: 47
<212> TYPE: DNA
<213> ORGANISM: Artificial sequence
<220> FEATURE:
<223> OTHER INFORMATION: VH, 2nd Round For primer
<220> FEATURE:
<221> NAME/KEY: misc_feature
<222> LOCATION: (1)..(9)
<223> OTHER INFORMATION: n is a, c, g, or t

<400> SEQUENCE: 96
nnnnnnnnna agcggccgcc accatggccc aggtkcagct ggtgcag                    47

<210> SEQ ID NO 97
<211> LENGTH: 47
<212> TYPE: DNA
<213> ORGANISM: Artificial sequence
<220> FEATURE:
<223> OTHER INFORMATION: VH, 2nd Round For primer
<220> FEATURE:
<221> NAME/KEY: misc_feature
<222> LOCATION: (1)..(9)
<223> OTHER INFORMATION: n is a, c, g, or t

<400> SEQUENCE: 97
nnnnnnnnna agcggccgcc accatggccc aggtccagct tgtgcag                    47

<210> SEQ ID NO 98
<211> LENGTH: 47
<212> TYPE: DNA
<213> ORGANISM: Artificial sequence
<220> FEATURE:
<223> OTHER INFORMATION: VH, 2nd Round For primer
<220> FEATURE:
<221> NAME/KEY: misc_feature
<222> LOCATION: (1)..(9)
<223> OTHER INFORMATION: n is a, c, g, or t

<400> SEQUENCE: 98
nnnnnnnnna agcggccgcc accatggccc aggtccagct ggtacag                    47

<210> SEQ ID NO 99
<211> LENGTH: 47
<212> TYPE: DNA
<213> ORGANISM: Artificial sequence
<220> FEATURE:
<223> OTHER INFORMATION: VH, 2nd Round For primer
<220> FEATURE:
<221> NAME/KEY: misc_feature
<222> LOCATION: (1)..(9)
<223> OTHER INFORMATION: n is a, c, g, or t

<400> SEQUENCE: 99
nnnnnnnnna agcggccgcc accatggccc aratgcagct ggtgcag                    47

<210> SEQ ID NO 100
<211> LENGTH: 47
<212> TYPE: DNA
<213> ORGANISM: Artificial sequence
<220> FEATURE:
<223> OTHER INFORMATION: VH, 2nd Round For primer
<220> FEATURE:
<221> NAME/KEY: misc_feature
<222> LOCATION: (1)..(9)
<223> OTHER INFORMATION: n is a, c, g, or t

<400> SEQUENCE: 100 nnnnnnnna agcggccgcc accatggccg aggtccagct ggtacag        47

<210> SEQ ID NO 101
<211> LENGTH: 47
<212> TYPE: DNA
<213> ORGANISM: Artificial sequence
<220> FEATURE:
<223> OTHER INFORMATION: VH, 2nd Round For primer
<220> FEATURE:
<221> NAME/KEY: misc_feature
<222> LOCATION: (1)..(9)
<223> OTHER INFORMATION: n is a, c, g, or t

<400> SEQUENCE: 101 nnnnnnnna agcggccgcc accatggccc agrtcacctt gaaggag        47

<210> SEQ ID NO 102
<211> LENGTH: 47
<212> TYPE: DNA
<213> ORGANISM: Artificial sequence
<220> FEATURE:
<223> OTHER INFORMATION: VH, 2nd Round For primer
<220> FEATURE:
<221> NAME/KEY: misc_feature
<222> LOCATION: (1)..(9)
<223> OTHER INFORMATION: n is a, c, g, or t

<400> SEQUENCE: 102 nnnnnnnna agcggccgcc accatggccg aggtgcagct ggtggag        47

<210> SEQ ID NO 103
<211> LENGTH: 47
<212> TYPE: DNA
<213> ORGANISM: Artificial sequence
<220> FEATURE:
<223> OTHER INFORMATION: VH, 2nd Round For primer
<220> FEATURE:
<221> NAME/KEY: misc_feature
<222> LOCATION: (1)..(9)
<223> OTHER INFORMATION: n is a, c, g, or t

<400> SEQUENCE: 103 nnnnnnnna agcggccgcc accatggccc aggtgcagct ggtggag        47

<210> SEQ ID NO 104
<211> LENGTH: 47
<212> TYPE: DNA
<213> ORGANISM: Artificial sequence
<220> FEATURE:
<223> OTHER INFORMATION: VH, 2nd Round For primer
<220> FEATURE:
<221> NAME/KEY: misc_feature
<222> LOCATION: (1)..(9)
<223> OTHER INFORMATION: n is a, c, g, or t

<400> SEQUENCE: 104 nnnnnnnna agcggccgcc accatggccc aggtgcagct gcaggag        47

<210> SEQ ID NO 105
<211> LENGTH: 47
<212> TYPE: DNA
<213> ORGANISM: Artificial sequence
<220> FEATURE:
<223> OTHER INFORMATION: VH, 2nd Round For primer
<220> FEATURE:
<221> NAME/KEY: misc_feature
<222> LOCATION: (1)..(9)
<223> OTHER INFORMATION: n is a, c, g, or t

<400> SEQUENCE: 105
nnnnnnnnna agcggccgcc accatggccc agctgcagct gcaggag      47

<210> SEQ ID NO 106
<211> LENGTH: 47
<212> TYPE: DNA
<213> ORGANISM: Artificial sequence
<220> FEATURE:
<223> OTHER INFORMATION: VH, 2nd Round For primer
<220> FEATURE:
<221> NAME/KEY: misc_feature
<222> LOCATION: (1)..(9)
<223> OTHER INFORMATION: n is a, c, g, or t

<400> SEQUENCE: 106
nnnnnnnnna agcggccgcc accatggccc aggtgcagct acagcag      47

<210> SEQ ID NO 107
<211> LENGTH: 47
<212> TYPE: DNA
<213> ORGANISM: Artificial sequence
<220> FEATURE:
<223> OTHER INFORMATION: VH, 2nd Round For primer
<220> FEATURE:
<221> NAME/KEY: misc_feature
<222> LOCATION: (1)..(9)
<223> OTHER INFORMATION: n is a, c, g, or t

<400> SEQUENCE: 107
nnnnnnnnna agcggccgcc accatggccg aggtgcagct ggtgcag      47

<210> SEQ ID NO 108
<211> LENGTH: 47
<212> TYPE: DNA
<213> ORGANISM: Artificial sequence
<220> FEATURE:
<223> OTHER INFORMATION: VH, 2nd Round For primer
<220> FEATURE:
<221> NAME/KEY: misc_feature
<222> LOCATION: (1)..(9)
<223> OTHER INFORMATION: n is a, c, g, or t

<400> SEQUENCE: 108
nnnnnnnnna agcggccgcc accatggccg aagtgcagct ggtgcag      47

<210> SEQ ID NO 109
<211> LENGTH: 47
<212> TYPE: DNA
<213> ORGANISM: Artificial sequence
<220> FEATURE:
<223> OTHER INFORMATION: VH, 2nd Round For primer
<220> FEATURE:
<221> NAME/KEY: misc_feature
<222> LOCATION: (1)..(9)
<223> OTHER INFORMATION: n is a, c, g, or t

<400> SEQUENCE: 109
nnnnnnnnna agcggccgcc accatggccc aggtacagct gcagcag      47

<210> SEQ ID NO 110
<211> LENGTH: 22
<212> TYPE: DNA
<213> ORGANISM: Artificial sequence
<220> FEATURE:
<223> OTHER INFORMATION: VH, 1st Round Reverse primer

<400> SEQUENCE: 110

```
tgaggagacr gtgaccaggg tg                                              22
```

<210> SEQ ID NO 111
<211> LENGTH: 21
<212> TYPE: DNA
<213> ORGANISM: Artificial sequence
<220> FEATURE:
<223> OTHER INFORMATION: VH, 1st Round Reverse primer

<400> SEQUENCE: 111

```
tgaagagacg gtgaccattg t                                               21
```

<210> SEQ ID NO 112
<211> LENGTH: 22
<212> TYPE: DNA
<213> ORGANISM: Artificial sequence
<220> FEATURE:
<223> OTHER INFORMATION: VH, 1st Round Reverse primer

<400> SEQUENCE: 112

```
tgaggagacg gtgaccaggg tt                                              22
```

<210> SEQ ID NO 113
<211> LENGTH: 23
<212> TYPE: DNA
<213> ORGANISM: Artificial sequence
<220> FEATURE:
<223> OTHER INFORMATION: VH, 1st Round Reverse primer

<400> SEQUENCE: 113

```
tgaggagacg gtgaccgtgg tcc                                             23
```

<210> SEQ ID NO 114
<211> LENGTH: 37
<212> TYPE: DNA
<213> ORGANISM: Artificial sequence
<220> FEATURE:
<223> OTHER INFORMATION: VH, 2nd Round Reverse primer

<400> SEQUENCE: 114

```
gccactagtg agtcgacact gaggagacrg tgaccag                              37
```

<210> SEQ ID NO 115
<211> LENGTH: 37
<212> TYPE: DNA
<213> ORGANISM: Artificial sequence
<220> FEATURE:
<223> OTHER INFORMATION: VH, 2nd Round Reverse primer

<400> SEQUENCE: 115

```
gccactagtg agtcgacact gaagagacgg tgaccat                              37
```

<210> SEQ ID NO 116
<211> LENGTH: 37
<212> TYPE: DNA
<213> ORGANISM: Artificial sequence
<220> FEATURE:
<223> OTHER INFORMATION: VH, 2nd Round Reverse primer

<400> SEQUENCE: 116

```
gccactagtg agtcgacact gaggagacgg tgaccag                              37
```

<210> SEQ ID NO 117
<211> LENGTH: 37
<212> TYPE: DNA
<213> ORGANISM: Artificial sequence

```
<220> FEATURE:
<223> OTHER INFORMATION: VH, 2nd Round Reverse primer

<400> SEQUENCE: 117
gccactagtg agtcgacact gaggagacgg tgaccgt                                37
```